(12) United States Patent
Raz et al.

(10) Patent No.: US 11,628,156 B2
(45) Date of Patent: Apr. 18, 2023

(54) TERPENE-ENRICHED CANNABINOID COMPOSITION AND METHOD OF TREATMENT

(71) Applicant: BUZZELET DEVELOPMENT AND TECHNOLOGIES LTD, Or-Akiva (IL)

(72) Inventors: Noa Raz, Gizo (IL); Aharon M. Eyal, Jerusalem (IL)

(73) Assignee: BUZZELET DEVELOPMENT AND TECHNOLOGIES LTD, Or-Akiva (IL)

(*) Notice: Subject to any disclaimer, the term of this patent is extended or adjusted under 35 U.S.C. 154(b) by 261 days.

(21) Appl. No.: 16/747,569

(22) Filed: Jan. 21, 2020

(65) Prior Publication Data

US 2020/0261404 A1 Aug. 20, 2020

Related U.S. Application Data

(63) Continuation-in-part of application No. PCT/IB2018/001062, filed on Aug. 13, 2018.

(60) Provisional application No. 62/639,233, filed on Mar. 6, 2018, provisional application No. 62/587,494, filed on Nov. 17, 2017, provisional application No. 62/544,847, filed on Aug. 13, 2017.

(51) Int. Cl.
*A61K 31/352* (2006.01)
*A61K 31/015* (2006.01)
*A61K 31/045* (2006.01)
*A61K 31/05* (2006.01)
*A61K 47/46* (2006.01)

(52) U.S. Cl.
CPC .......... *A61K 31/352* (2013.01); *A61K 31/015* (2013.01); *A61K 31/045* (2013.01); *A61K 31/05* (2013.01); *A61K 47/46* (2013.01)

(58) Field of Classification Search
CPC ................ A61K 31/352; A61K 31/015; A61K 31/045; A61K 31/05; A61K 31/46
See application file for complete search history.

(56) References Cited

U.S. PATENT DOCUMENTS

| 2006/0140881 A1 | 6/2006 | Xu et al. |
| 2013/0203711 A1 | 8/2013 | Gupta |
| 2013/0289300 A1 | 10/2013 | Yu et al. |
| 2015/0297556 A1* | 10/2015 | Smith ............. A61K 47/08 424/449 |
| 2021/0023045 A1* | 1/2021 | Raz ............. A61K 45/06 |

FOREIGN PATENT DOCUMENTS

| AU | 2016100802 A4 | 7/2016 | |
| CN | 103690537 A | 2/2014 | |
| EP | 1177790 B1 | 5/2005 | |
| WO | 2003020371 A2 | 3/2003 | |
| WO | WO-2015068052 A2 * | 10/2013 | ............. A23L 2/00 |
| WO | 2015068052 A2 | 5/2015 | |
| WO | WO-2015068052 A2 * | 5/2015 | ............. A23L 2/00 |

OTHER PUBLICATIONS

Protective effect of linalool, myrcene, and eucalyptol against t-butyl hydroperoxide induced genotoxicity in bacteria and cultured human cells, Food and Chemical Toxicology, Published Nov. 2008 (Year: 2008).*
International Preliminary Report on Patentability for PCT/IB2018/001062 dated Feb. 18, 2020.
International Search Report for PCT/IB2018/001062 dated Apr. 3, 2019.
Extended European Search Report for corresponding European patent application No. EP18845952.3 dated Apr. 12, 2021.
International Search Report and Written Opinion for parent application PCT/IB2018/001062 dated Apr. 3, 2019.
International Preliminary Report on Patentability for parent application PCT/IB2018/001062 dated Feb. 18, 2020.

* cited by examiner

*Primary Examiner* — John S Kenyon
*Assistant Examiner* — Gillian A Hutter
(74) *Attorney, Agent, or Firm* — Alphapatent Associates, Ltd; Daniel J. Swirsky

(57) ABSTRACT

Provided is a therapeutic product comprising at least one cannabinoid; at least one primary terpene; and at least 5% by weight of a non-cannabinoid, non-terpene carrier, wherein said non-cannabinoid, non-terpene carrier comprises cellulose and the terpenes to cannabinoids weight/weight ratio in said product is about 0.1 to about 1.0. Also provided is a method of treating certain conditions and/or symptoms in a subject in need thereof, comprising administering to said subject a therapeutically effective amount of a product comprising at least one primary terpene. Further provided is a therapeutic product comprising a primary terpene blend, wherein said primary terpene blend comprises five or less terpenes, and wherein each one of those terpenes, where present, independently comprises at least 10% of the total terpene content.

2 Claims, No Drawings

TERPENE-ENRICHED CANNABINOID COMPOSITION AND METHOD OF TREATMENT

CROSS-REFERENCE TO RELATED APPLICATIONS

The present application is a continuation-in-part of International Application No. PCT/IB2018/001062, filed on Jun. 27, 2018, which claims the benefit of priority of U.S. Provisional Application No. 62/544,847 filed Aug. 13, 2017, of U.S. Provisional Application No. 62/587,494 filed Nov. 17, 2017, and of U.S. Provisional Application No. 62/639,233 filed Mar. 6, 2018, and which are incorporated by reference herein in their entireties.

FIELD OF THE INVENTION

The field of art to which this invention generally pertains is terpenes-enriched products, and specifically terpenes-enriched products for therapeutic use.

BACKGROUND OF THE INVENTION

*Cannabis* is a complex plant comprising over 400 chemical entities of which more than 60 are cannabinoid compounds, some of which have opposing pharmacological effects. In the naturally occurring *Cannabis* plant, cannabinoids are synthesized and accumulated as cannabinoid acids (e.g. tetrahydrocannabinolic acid (THCa) and cannabidioolic acid (CBDA). When the herbal product is dried, stored and heated, the acids decarboxylize into their active forms, such as tetrahydrocannabinol (THC) and Cannabidiol (CBD) [De Meijer et al. 2003; The inheritance of chemical phenotype in *Cannabis sativa* L. Genetics 63: 335-346].

There are major differences in functional pharmaceutical effects between the acid and decarboxylized forms (for instance THC is psychoactive, while THCa is not psychoactive), in physical properties (such as solubility and boiling point) and in chemical properties (e.g. THCa may undergo esterification and dimerization, while THC cannot, THCa solubility is pH dependent, while that of THC is not, etc.) (e.g. De Zeeuw, Journal of Pharmacy and Pharmacology, 1972; Mechoulam, Naturwissenschaften, 1978; Grotenhermen, Clinical Pharmacokinetics, 2003).

Terpenes are the major components of the essential oils present in various *Cannabis* varieties. These compounds are responsible for the distinctive aromas and flavors. Terpene yield and distribution in the plant vary according to numerous parameters, such as environmental conditions or maturity of the plant. (Meier and Mediavilla, 1998; Brenneisen, 2007). Terpene yield is less than 1% in most *cannabis* assays (Potter, 2009). Monoterpenes usually predominate in the natural plant (limonene, myrcene, pinene), but these headspace volatiles (Hood et al., 1973) suffer diminished yields with drying and storage (Turner et al., 1980; Ross and ElSohly, 1996), resulting in a higher relative proportion of sesquiterpenoids in processed *cannabis*. Being volatile agents, terpenes further evaporate during heating and decarboxylation.

Terpenes play important roles in cannabinoids-comprising products, affecting the functionality and bioavailability of the cannabinoids and the aroma of the product. Processing *cannabis* plant material typically leads to terpenes loss so that most of *cannabis* products are of relatively low terpene content. That is particularly true for *cannabis* extracts and products thereof, such as *cannabis* tablets, *cannabis* gel capsules, *cannabis* patches, *cannabis* suppositories, etc. Most *cannabis* terpenes boiling points are in the range between about 150° C. and about 220° C. and they evaporate, at least partially, during *cannabis* buds drying, during solvent separation from extracts and during decarboxylation. Monoterpenes are lost at a rate greater than that of terpenes with a higher molecular weight and terpenes carrying no hydroxyl groups are lost at a rate greater than that of terpenes that do carry hydroxyl groups.

Primary terpenes found in *cannabis* include pinene, linalool, myrcene, limonene, ocimene, terpinolene, terpineol, caryophyllene, valencene, geraniol and humulene. Secondary terpenes include Phellandrene, terpinene, carene, fenchol, bisabolol, borneol, phytol, camphene, sabinene, camphor.

SUMMARY OF THE INVENTION

According to an aspect of some embodiments of the present invention, provided is a therapeutic product comprising, (i) at least one cannabinoid, (ii) at least one primary terpene, (iii) at least 5% by weight of a non-cannabinoid, non-terpene carrier; (a) wherein said non-cannabinoid, non-terpene carrier comprises cellulose and the terpenes to cannabinoids weight/weight ratio in said product is about 0.1 to about 1.0, or; (b) wherein said non-cannabinoid, non-terpene carrier comprises less than 5% by weight cellulose and the terpenes to cannabinoids weight/weight ratio in said product is about 0.05 to about 1.0; forming a terpene-enriched cannabinoid product with an enhanced therapeutic effect compared with that of a product comprising the same cannabinoids amounts and one half the amount of said primary terpene.

According to a further aspect of some embodiments of the present invention, provided is a method of treating a condition and/or symptom in a subject in need thereof, comprising administering to said subject a therapeutically effective amount of a product comprising at least one primary terpene, said method providing an enhanced therapeutic effect compared with that obtained by administrating a product comprising one half the amount of said primary terpene, wherein said condition and/or symptom is selected from the group consisting of arthritis, osteoarthritis, arthralgia, joint pain, joint stiffness, diabetes, lack of appetite, anorexia, vomiting, nausea, an inflammatory bowel disease including Crohn's disease and ulcerative colitis, dementia, memory loss, osteoporosis, fatigue, weakness, decreased mental energy, decreased physical energy, dizziness, deficits in balance, itchy skin, pruritus and/or chronic pruritus, wrinkles, stretch marks, skin burn, headache, migraine, weight gain, digestive problem, intestinal disorder, gastrointestinal pain, abdominal pain, pelvic pain, constipation, diarrhea, hot flashes, sweating, difficulty in concentration, weakened immune system, cardiovascular disease, palpitation and tachycardia, psoriasis, dermatophytes, *Candida*, leishmaniasis, Methycillin-resistant *Staphylococcus aureus* (MRSA), malaria, allergy, fibromyalgia, nociceptive pain, neuropathic pain, pain, arm or leg pain, acne, insomnia and/or sleep disorders, muscle pain, myalgia, spasticity, muscle tension, cramps, spasms, anxiety, irritability, nervousness, restless, stress, depression, mood problem, affect disorders, anger, autism and/or autism spectrum disorder, neurodegenerative diseases, Alzheimer disease, Parkinson disease, Huntington's disease, Dystonia, Amyotrophic Lateral Sclerosis (ALS), multiple sclerosis, Tourette syndrome, Myasthenia Gravis, epilepsy, cancer, inflammatory airway diseases including asthma and/or chronic obstructive pulmonary disease (COPD), addiction, stroke, traumatic brain injury, motor spasm and/or tic, vocal tic, obsessive compulsive disorder (OCD), attention deficit hyperactivity disorder (ADHD), attention deficit disorder (ADD), cerebral palsy (CP), inflammation, oxidative stress, paresthesia, glaucoma and combinations thereof.

According to a further aspect of some embodiments of the present invention, provided is a therapeutic product comprising a primary terpene blend, wherein said primary terpene blend comprises five or less terpenes, and wherein each one of those terpenes, where present, independently comprises at least 10% of the total terpene content, forming a therapeutic product with an enhanced therapeutic effect compared with that of a product comprising one half the amount of the primary terpene blend.

DETAILED DESCRIPTION OF THE INVENTION

Unless indicated otherwise the term aging as used herein refers to getting older, e.g. reaching an age greater than 50, greater than 60, greater than 70 or greater than 80.

Unless indicated otherwise the term child as used herein, refers to a person under the age of 18.

Unless indicated otherwise the term "therapeutic effect applies to a child" as used herein, refers to therapeutic effect observed when the treated patient is a child. Unless indicated otherwise the term "treat" and/or "treating" as used herein, refers to treating, healing, relieving, decreasing, preventing and/or reducing the risk associated with, and/or improving the quality of life associated with.

Unless indicated otherwise, percent is weight percent and ratio is weight/weight ratio. Unless indicated otherwise, weight ratio means the ratio between weight content, e.g. in an aqueous solution containing 20% solute and 80% water, the solute to water weight ratio is 20:80 or 1:4.

Unless indicated otherwise, the term cannabinoid as used herein refers to a compound that affects the endocannabinoid system. Cannabinoids are agonists or antagonists to receptors in the endocannabinoid system.

As used herein, the term THC refers to THCa (tetrahydrocannabiniolic acid) and/or to THC (tetrahydrocannabiniol) unless indicated otherwise. As used herein, the term CBD refers to CBDa (cannabidiolic acid) and/or to CBD (cannabidiol) unless indicated otherwise. As used herein, the term CBG refers to CBGa (cannabigerolic acid) and/or to CBG (cannabigerol) unless indicated otherwise. As used herein, the term CBN refers to CBNa (Cannabinolic acid) and/or to CBN (cannabinol) unless indicated otherwise. As used herein, the term CBC refers to CBCa (cannabichromenic acid) and/or to CBC (Cannabichromene) unless indicated otherwise. As used herein, the term CBL refers to CBLa (Cannabicycol acid) and/or to CBL (Cannabicyclol) unless indicated otherwise. As used herein, the term THCV refers to THCVa (tetrahydrocannabivarin acid) and/or to THCV (tetrahydrocannabivarin) unless indicated otherwise. As used herein, the term CBDV refers to CBDVa (cannabigerovarin acid) and/or to CBDV (cannabidivarin) unless indicated otherwise.

As used herein, the term cellulose refers to cellulose, hemicellulose and their combinations. As used herein, the term glycol refers to any glycol, including ethylene glycol, polyethylene glycol, propylene glycol and polypropylene glycol. As used herein, the term chlorophyll refers to chlorophyll and degradation products thereof.

As used herein, "terpene" refers to both terpenes and terpenoids.

As used herein and unless indicated otherwise, the term "terpenes/cannabinoids (or terpenes to cannabinoids) weight/weight ratio" means the weight ratio between the combined amount of terpenes and the combined amount of cannabinoids.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

According to an embodiment, provided is a therapeutic product comprising (i) at least one cannabinoid in a specific amount, (ii) a primary terpene in a specific amount, (iii) at least 5% by weight of a non-cannabinoid, non-terpene, carrier, (iv) optionally at least three secondary terpenes; and (a) wherein the non-cannabinoid, non-terpene carrier comprises cellulose and the terpenes to cannabinoids weight/weight ratio in the product is about 0.1 to about 1.0, or (b) wherein the non-cannabinoid, non-terpene carrier comprises less than 5% by weight cellulose and the terpenes to cannabinoids weight/weight ratio in the product is 0.05 to about 1.0, forming a terpene-enriched cannabinoid product with an enhanced therapeutic effect compared with that of a product comprising the same cannabinoids amounts and one half the amount of said primary terpene. According to an embodiment, said product is a composition or the terms "product" and "composition are used interchangeably. According to an embodiment, said product comprises a composition comprising (i) at least one cannabinoid in a specific amount, (ii) a primary terpene in a specific amount, (iii) at least 5% by weight of a non-cannabinoid, non-terpene, carrier, (iv) optionally at least three secondary terpenes; and (a) wherein the non-cannabinoid, non-terpene carrier comprises cellulose and the terpenes to cannabinoids weight/weight ratio in the composition is about 0.1 to about 1.0, or (b) wherein the non-cannabinoid, non-terpene carrier comprises less than 5% by weight cellulose and the terpenes to cannabinoids weight/weight ratio in the composition is 0.05 to about 1.0. According to an embodiment, said product comprises a composition resulting from processing a plant material.

According to an embodiment, the product has an enhanced therapeutic effect in treating and/or healing and/or relieving and/or decreasing, preventing and/or reducing the risk associated with, and/or improving the quality of life associated with conditions and/or symptoms associated with at least one of arthritis, osteoarthritis, arthralgia, joint pain, joint stiffness, diabetes, lack of appetite, anorexia, vomiting, nausea, an inflammatory bowel disease including Crohn's disease and ulcerative colitis, dementia, memory loss, osteoporosis, fatigue, weakness, decreased mental energy, decreased physical energy, dizziness, deficits in balance, itchy skin, pruritus and/or chronic pruritus, wrinkles, stretch marks, skin burn, headache, migraine, weight gain, digestive problem, intestinal disorder, gastrointestinal pain, abdominal pain, pelvic pain, constipation, diarrhea, hot flashes, sweating, difficulty in concentration, weakened immune system, cardiovascular disease, palpitation and tachycardia, psoriasis, dermatophytes, *Candida*, leishmaniasis, Methycillin-resistant *Staphylococcus aureus* (MRSA), malaria, allergy, fibromyalgia, nociceptive pain, neuropathic pain, pain, arm or leg pain, acne, insomnia and/or sleep disorders, muscle pain, myalgia, spasticity, muscle tension, cramps, spasms, anxiety, irritability, nervousness, restless, stress, depression, mood problem, affect disorders, anger, autism and/or autism spectrum disorder, neurodegenerative diseases, Alzheimer disease, Parkinson disease, Huntington's disease, Dystonia, Amyotrophic Lateral Sclerosis (ALS), multiple sclerosis, Tourette syndrome, Myasthenia Gravis, epilepsy, cancer, inflammatory airway diseases including asthma and/or chronic obstructive pulmonary disease (COPD), addiction, stroke, traumatic brain injury, motor spasm and/or tic, vocal tic, obsessive compulsive disorder (OCD), attention deficit hyperactivity disorder (ADHD), attention deficit disorder (ADD), cerebral palsy (CP), inflammation, oxidative stress, paresthesia, glaucoma and combinations thereof. According to an embodiment, the conditions and/or symptoms are associated with aging.

According to an embodiment, the product has an enhanced therapeutic effect in treating conditions and/or symptoms associated with aging. According to a related embodiment, the primary terpene is selected from the group consisting of caryophyllene, linalool, pinene, eucalyptol, sabinene, terpineol and combinations thereof. According to an embodiment, the composition comprises at least 2 of the terpenes, at least 3, at least 4 or at least 5 of the terpenes. According to an embodiment, the primary terpene is selected from the group consisting of caryophyllene, linalool, pinene, terpineol and combinations thereof. According to an embodiment, the primary terpene is selected from the group consisting of caryophyllene, linalool, sabinene and combinations thereof.

According to an embodiment, the enhanced therapeutic effect applies to a child. As used herein the term "therapeutic effect applies to a child" refers to therapeutic effect observed when the treated patient is a child.

According to an embodiment, the product has an enhanced therapeutic effect in treating a child. According to a related embodiment, the primary terpene is selected from the group consisting of caryophyllene, limonene, pinene, terpineol and combinations thereof. According to an embodiment, the composition comprises at least 2 of the terpenes, at least 3, or all 4 of the terpenes. According to an embodiment, the primary terpene is selected from the group consisting of caryophyllene, limonene and combination thereof.

According to an embodiment, the conditions and/or symptoms are observed in a child.

According to an embodiment, the product is selected from the group consisting of tablets, gel capsules, medical patches, topicals, creams, varnishes, sublingual oils, sprays, edibles, beverages, suppositories, tampons, rectal candles, cigarettes, vaporizer liquids, nasal preparation, preparations containing micro and/or nano-emulsions, preparations containing micro and/or nano-particles and combinations thereof.

According to an embodiment, the product comprises at least two cannabinoids, at least three, at least four or at least five. According to an embodiment, the content of each cannabinoid in the product is at least 10 parts per million (ppm). As known in the art, cannabinoids have an acid form and a non-acid form (which is also referred to as decarboxylated form, since it can be generated by decarboxylating the acid form). The acid form is indicated herein by the letter (a) at the end of the cannabinoid acronym, e.g. tetrahydrocannabiniolic acid is indicated as THCa, while the decarboxylated form is THC. According to an embodiment, the cannabinoids are selected from the group consisting of tetrahydrocannabiniol in acid or decarboxylated form (THCa or THC, respectively), cannabidiol in acid or decarboxylated form (CBDa or CBD, respectively), cannabigerol in acid or decarboxylated form (CBGa or CBG, respectively), cannabichromene in acid or decarboxylated form (CBCa or CBC, respectively) tetrahydrocannabivarin in acid or decarboxylated form (THCVa or THCV, respectively), Cannabidivarin in acid or decarboxylated form (CBDVa or CBDV respectively), Cannabinol in acid or decarboxylated form (CBNa or CBN, respectively), Cannabicyclol in acid or decarboxylated form (CBLa or CBL, respectively). As used herein, the term THC refers to THCa (tetrahydrocannabiniolic acid) and/or to THC (tetrahydrocannabiniol) unless indicated otherwise. As used herein, the term CBD refers to CBDa (cannabidiolic acid) and/or to CBD (cannabidiol) unless indicated otherwise. As used herein, the term CBG refers to CBGa (cannabigerolic acid) and/or to CBG (cannabigerol) unless indicated otherwise. As used herein, the term CBN refers to CBNa (Cannabinolic acid) and/or to CBN (cannabinol) unless indicated otherwise. As used herein, the term CBC refers to CBCa (cannabichromenic acid) and/or to CBC (Cannabichromene) unless indicated otherwise. As used herein, the term CBL refers to CBLa (Cannabicycol acid) and/or to CBL (Cannabicyclol) unless indicated otherwise. As used herein, the term THCV refers to THCVa (tetrahydrocannabivarin acid) and/or to THCV (tetrahydrocannabivarin) unless indicated otherwise. As used herein, the term CBDV refers to CBDVa (cannabigerovarin acid) and/or to CBDV (cannabidivarin) unless indicated otherwise. Thus, the term "CBD to THC ratio" may mean "CBD to THC ratio", "CBDa to THC ratio", "CBD to THCa ratio", "CBDa to THCa ratio", "CBD to THC+THCa ratio", "CBDa to THC+THCa ratio", "CBD+CBDa to THC ratio", "CBD+CBDa to THCa ratio" or "CBD+CBDa to THC+THCa ratio".

According to an embodiment, at least one of the cannabinoids is in acid form. According to an embodiment, at least one of the cannabinoid is at least partially in decarboxylated form. According to an embodiment, at least 50% of the cannabinoid is in decarboxylated form, at least 60%, at least 70%, at least 80% or at least 90%.

According to an embodiment, the product comprises THC and/or THCa. According to an embodiment, the product comprises CBD and/or CBDa. According to an embodiment, the product comprises THC and/or THCa at a content of less than 1%, less than 0.8%, less than 0.6%, less than 0.4% or less than 0.2%. According to an embodiment, the product comprises both CBD and/or CBDa and THC and/or THCa and the weight/weight ratio between CBD and/or CBDa and THC and/or THCa ((CBD+CBDa)/(THC+THCa)) is at least 10, at least 15, at least 20, at least 25 or at least 30. According to an embodiment, the product comprises CBG and/or CBGa. According to an embodiment, the product comprises CBN and/or CBNa. According to an embodiment, the product comprises CBC and/or CBCa. According to an embodiment, the product comprises CBL and/or CBLa. According to an embodiment, the product comprises THCV and/or THCVa. According to an embodiment, the product comprises CBDV and/or CBDVa.

According to an embodiment, the product comprises at least 2% by weight carrier, at least 3%, at least 5%, at least 7%, at least 10%, at least 12%, at least 15%, at least 20%, at least 25%, at least 30%, at least 35% or at least 40% by weight. Any compound other than cannabinoids and terpenes is a suitable carrier. According to an embodiment, the carrier is selected from the group consisting of vegetable oils, e.g. coconut oil, olive oil or sesame oil, pharmaceutical excipients, honey, bees wax, cellulose and combinations thereof. As used herein, the term cellulose refers to cellulose, hemicellulose and their combinations.

According to an embodiment, the product comprises a primary terpene and optionally at least one secondary terpenes, at least two, at least three, at least four, or at least five secondary terpenes. The term "terpene", as used herein, refers to both terpenes and terpenoids. As used here, the term "primary terpene" refers to a terpene that forms at least 20% by weight of the total amount of terpenes in the product, at least 25%, at least 30%, at least 35%, at least 40%, at least 50%, at least 60%, at least 70% or at least 80%. As used here, the term "primary terpene" refers to a terpene having the greatest amount in the composition. As used here, the term "primary terpene" refers to a terpene that forms the highest terpene concentration in the composition. According to an embodiment, the product comprises multiple (e.g. two, three, or four) terpenes, each one of which forms at least 20% by weight of the total amount of terpenes in the product and each one of these terpenes is considered a primary terpene. According to an embodiment, the product comprises multiple (e.g. two, three, or four) terpenes, each one of which forms at least 15% by weight of the total amount of terpenes in the product, at least 18%, at least 22%, at least 25%, at least 30%, at least 35%, or at least 40%, and each one of these terpenes is considered a primary terpene. As used here, the term "secondary terpene" refers to a terpene that forms at least 10 parts per million (ppm) of the product. According to an embodiment, the content of the primary terpene in the product is at least 1.3 times greater than that of any secondary terpene, at least 1.5, at least 2, at least 2.2, at least 2.5, at least 3, at least 3.5, at least 4, at least 6, at least 8, at least 10, at least 15, at least 20, at least 25, or at least 30 times greater.

As used herein, "terpenes/cannabinoids (or terpenes to cannabinoids) weight/weight ratio" means the weight ratio between the combined amount of terpenes and the combined amount of cannabinoids. According to an embodiment, the non-cannabinoid, non-terpene carrier comprises cellulose and the terpenes to cannabinoids weight/weight ratio in the product is about 0.1 to about 1.0. According to an embodiment said non-cannabinoid, non-terpene, carrier comprises at least 5% by weight cellulose, at least 6%, at least 8%, at least 10%, at least 15%, or at least 20%. According to an embodiment, the ratio is greater than 0.1, greater than 0.12, greater than 0.13, greater than 0.15, greater than 0.2, greater than 0.25, greater than 0.3, greater than 0.35, greater than 0.4, greater than 0.45, greater than 0.5, greater than 0.55, greater than 0.6, greater than 0.65, greater than 0.7, greater than 0.75, greater than 0.8, greater than 0.85, greater than 0.9, greater than 0.95, greater than 1, greater than 1.2, greater than 1.5, greater than 2.0, greater than 3 or greater than 5. According to an embodiment, the ratio is less than 1, less than 0.9, less than 0.8, less than 0.7, less than 0.6, less than 0.5, less than 0.4, less than 0.3, less than 0.2 or less than 0.15. According to an embodiment, the product comprising more than 5% cellulose is selected from the group consisting of *cannabis* plant material, e.g. *cannabis* buds (also referred to as *cannabis* inflorescence) or *cannabis* trim, ground forms thereof, plant material preparation for vaporizers and *cannabis* cigarette. According to an embodiment, the product comprises a dried *cannabis* plant material.

According to another embodiment, the non-cannabinoid, non-terpene carrier comprises less than 5% by weight cellulose and terpenes to cannabinoids weight/weight ratio in the product is in the range between about 0.05 and about 1.0. According to an embodiment said non-cannabinoid, non-terpene, carrier comprises less than 5% by weight cellulose, less than 4%, less than 3%, less than 2%, or less than 1% cellulose. According to an embodiment, the ratio is greater than 0.05, greater than 0.06, greater than 0.07, greater than 0.08, greater than 0.09, greater than 0.1, greater than 0.12, greater than 0.15, greater than 0.2, greater than 0.25, greater than 0.3, greater than 0.35, greater than 0.4, greater than 0.45, greater than 0.5, greater than 0.55, greater than 0.6, greater than 0.65, greater than 0.7, greater than 0.75, greater than 0.8, greater than 0.85, greater than 0.9, greater than 0.95, greater than 1, greater than 1.2, greater than 1.5, greater than 2.0, greater than 3 or greater than 5. According to an embodiment, the ratio is less than 1, less than 0.9, less than 0.8, less than 0.7, less than 0.6, less than 0.5, less than 0.4, less than 0.3, less than 0.2, less than 0.15, less than 0.1, less than 0.09, less than 0.08, less than 0.07, less than 0.06, or less than 0.05. According to an embodiment, the product comprising less than 5% cellulose is selected from the group consisting of *cannabis* trichomes, *cannabis* extracts and products thereof, such as tablets, gel capsules, medical patches, topicals, creams, varnishes, sublingual oils, sprays, edibles, beverages, suppositories, tampons, rectal candles, cigarettes, vaporizer liquids, nasal preparation, preparations containing micro and nano-emulsions, preparations containing micro and nano-particles and combinations thereof. According to an embodiment, said product comprises a liquid.

According to an embodiment, the primary terpene, the secondary terpenes or both are selected from the group consisting of pinene, limonene, linalool, caryophyllene, caryophyllene oxide, myrcene, humulene, borneol, eucalyptol, terpineol, nerolidol, phytol, geraniol, bisabolol, camphene, amyrin, thujone, citronellol, pulegone, cycloartenol, cymene, sabinene, carene, terpinene, fenchol, isopulegol, guaiol, phellandrene, eudesmol, ocimene, cardinol, elemene, friedelin, carvacrol, eugenol, camphor, menthol, iso-menthone, neral, gerial, viridiflorol, germacrene, thymol, Menth-2-en-1-ol, farensol, carotol, myrtenol, isomers thereof and combinations thereof. According to an embodiment, the primary terpene, the secondary terpenes or both, are selected from the group consisting of pinene, limonene, linalool, caryophyllene, myrcene, terpineol, eucalyptol, geraniol and combinations thereof. According to an embodiment, the primary terpene the secondary terpenes or both, are selected from the group consisting of pinene, limonene, linalool, caryophyllene, myrcene, terpineol, eucalyptol and combinations thereof. According to an embodiment, the primary terpene is selected from the group consisting of pinene, limonene, linalool, caryophyllene, myrcene, terpineol, eucalyptol, geraniol, humulene and combinations thereof. According to an embodiment, at least one of the terpenes is a-cyclic. According to an embodiment, at least one of the terpenes is cyclic. According to an embodiment, at least one of the terpenes is not found in cannabis buds or is present there at less than 0.2%, less than 0.1%, less than 0.05% or less than 0.02%. Such terpene is referred to as "non-cannabis terpene". According to an embodiment, the terpene-enriched cannabinoid product comprises the non-cannabis terpene at a concentration of at least 0.2%, at least 0.5%, least 0.8%, at least 1%, at least 1.5%, at least 2%, at least 3%, least 4%, at least 5%, at least 8% or at least 12%.

According to an embodiment, the terpenes comprise at least one monoterpene selected from the group consisting of limonene, myrcene, pinene, linalool, geraniol, terpinene camphene and isomers thereof. According to an embodiment, the terpenes comprise at least one sesquiterpene selected from the group consisting of nerolidol, caryophyllene, farnesene, zingiberene, vetivazulene, guaiazulene, longifolene, copaene, patchoulol humulene and isomers thereof. According to an embodiment, the terpenes comprise at least one diterpene selected from the group consisting of phytol, retinal, retinol, phytane, cembrene, sclarene, labdane, abietane, texadiene, stemarene, stemoden and isomers thereof. According to an embodiment, the terpenes comprise at least one hydroxy-terpene selected from the group consisting of nerolidol, geraniol, linalool, phytol and isomers thereof. As used herein "hydroxy-terpene" refers to a terpene carrying a hydroxyl function.

According to an embodiment, at least one of the terpenes is a monoterpene, at least one of the terpenes is a sesquiterpene and the monoterpenes to sesquiterpenes weight/weight ratio (i.e. the weight ratio between the total amount of monoterpenes and the total amount of the sesquiterpenes) is greater than 1.5 greater than 2, greater than 2.5, greater than 3, greater than 3.5, greater than 4, greater than 4.5, greater than 5, greater than 6, greater than 7, greater than 8, greater than 9, greater than 10, greater than 15, or greater than 20.

According to an embodiment, at least one of the terpenes is a monoterpene, at least one of the terpenes is a diterpene and the monoterpenes to diterpenes weight/weight ratio (i.e. the weight ratio between the total amount of monoterpenes and the total amount of the diterpenes) is greater than 5, greater than 6, greater than 7, greater than 8, greater than 9, greater than 10, greater than 12, greater than 14, greater than 16, greater than 18, greater than 20, greater than 25, or greater than 30.

According to an embodiment, at least one of the terpenes carries no hydroxyl group, at least one of the terpenes carries hydroxyl group and the non-hydroxy-terpenes to hydroxyl-terpenes weight/weight ratio (i.e. the weight ratio between the total amount of non-hydroxy-terpenes and the total amount of the hydroxy-terpenes) is greater than 1.5, greater than 2, greater than 2.5, greater than 3, greater than 3.5, greater than 4, greater than 4.5, greater than 5, greater than 6, greater than 7, greater than 8, greater than 9, greater than 10, greater than 15, or greater than 20.

According to an embodiment, terpenes form at least 0.5% by weight of the product, at least 0.6%, at least 0.8%, at least 1%, at least 2%, at least 3%, at least 5%, at least 10%, at least 20%, at least 30%, at least 40%, at least 50%, at least 60% or at least 70%.

According to an embodiment, the product comprises a composition, which is liquid at 30° C. According to an embodiment, the product comprises a composition, which is a suspension at 30° C. According to an embodiment, the product comprises a composition, which is essentially clear of haze or suspended solids at 30° C.

According to an embodiment, the product comprises cannabis plant material. According to an embodiment, the product comprises cannabis bud. According to an embodiment, the cannabis bud forms at least 20% of the product, at least 30%, at least 40%, at least 50%, at least 60%, at least 70% or at least 80%.

According to an embodiment the product comprises tetrahydrocannabinol (THC) and/or tetrahydrocannabinolic acid (THCa), wherein THC and/or THCa is in a total concentration of at least 1% by weight, at least 2%, at least 3%, at least 4%, at least 5%, at least 6%, at least 8%, at least 10%, at least 12%, at least 14%, at least 16%, at least 18%, or at least 20%, at least 30%, at least 40%, at least 50%, at least 60%, at least 70%, at least 80%, or at least 90% by weight.

According to an embodiment, the product comprises cannabidiol (CBD) and/or cannabidiolic acid (CBDa), wherein CBD and/or CBDa is in a total concentration of at least 1% by weight, at least 2%, at least 3%, at least 4%, at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight.

According to an embodiment, the product comprises tetrahydrocannabinol (THC) and/or tetrahydrocannabinolic acid (THCa) and cannabidiol (CBD) and/or cannabidiolic acid (CBDa), wherein, THC and/or THCa is in a total concentration of at least 2.5% by weight, and CBD and/or CBDa is in a total concentration of at least 2.5% by weight; THC and/or THCa in a total concentration of at least 3% by weight, and CBD and/or CBDa in a total concentration of at least 3% by weight; THC and/or THCa in a total concentration of at least 4% by weight, and CBD and/or CBDa in a total concentration of at least 4% by weight; THC and/or THCa in a total concentration of at least 5% by weight, and CBD and/or CBDa in a total concentration of at least 5% by weight; THC and/or THCa in a total concentration of at least 8% by weight, and CBD and/or CBDa in a total concentration of at least 8% by weight; THC and/or THCa in a total concentration of at least 10% by weight, and c CBD and/or CBDa in a total concentration of at least 10% by weight.

According to a related embodiment, said product comprises cannabigerol (CBG) and/or cannabigerol acid (CBGa) in a total concentration of at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises cannabinol (CBN) and/or cannabinol acid (CBNa) in a total concentration of at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises cannabichromene (CBC) and/or cannabichromenic acid (CBCa) in a total concentration of at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises cannabicyclol (CBL) and/or cannabicyclol acid (CBLa) in a total concentration at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises tetrahydrocannabivarin (THCV), and/or tetrahydrocannabivarin acid (THCVA) in a total concentration at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises cannabidivarin (CBDV) and/or cannabigerovarin acid (CBGVA) in a total concentration at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight.

According to an embodiment, the product comprises less than 5% by weight glycol, less than 4%, less than 3%, less than 2%, or less than 1%, by weight glycol. As used herein, the term glycol refers to any glycol, including ethylene glycol, polyethylene glycol, propylene glycol and polypropylene glycol.

According to an embodiment, the product comprises water and water content is less than 30% by weight, less than 25%, less than 20%, less than 15%, less than 12%, less than 10%, or less than 8%. According to an embodiment, water content is at least 1% by weight, at least 2%, at least 3%, at least 4% or at least 5% by weight. According to an embodiment, the product comprises water and water content is more than 50%, more than 60%, more than 70%, more than 80%, more than 90%, or more than 95%.

According to an embodiment, the product comprises chlorophyll. According to an embodiment, the product comprises at least 0.5% chlorophyll, at least 1, % at least 5%, at least 10%, at least 15%, at least 20% chlorophyll. As used herein, the term chlorophyll refers to chlorophyll and degradation products thereof. According to an embodiment, the product comprises at least one flavonoid. According to an embodiment, the product comprises at least two, at least three, at least four, or at least five flavonoids. According to an embodiment, the product comprises at least one of bergamottin, apigenin, amentoflavone, quercetin and piperine. According to an embodiment, the product comprises at least two, at least three, or at least four of bergamottin, apigenin, amentoflavone, quercetin and piperine. According to an embodiment, the product comprises bergamottin. According to an embodiment, the product comprises apigenin. According to an embodiment, the product comprises amentoflavone. According to an embodiment, the product comprises quercetin. According to an embodiment, the product comprises piperine According to an embodiment, the product results in an increased and/or enhanced therapeutic effect compared with that of a product comprising the same amounts of cannabinoids and optionally secondary terpenes and a smaller amount of the primary terpene, e.g. one half of that amount. According to various embodiment, the increased therapeutic effect has various forms, e.g. a shorter onset time, increased magnitude, extended duration, reduced dosages, reduced secondary adverse symptoms, reduced frequency of conditions and/or symptoms, reduced severity of conditions and/or symptoms, reduced consumption of other drugs and combinations thereof. According to an embodiment, the increased therapeutic effect comprises a shorter onset time, or differently put an earlier effect, which is important particularly in cases of sublingual and topical delivery and in cases where a rapid effect is desired, as in treating pain. According to an embodiment, the increased therapeutic effect comprises extended duration of the therapeutic effect, for example an extended time of pain relief. According to an embodiment, the increased therapeutic effect comprises increased magnitude of the therapeutic effect, enabling achieving a desired therapeutic effect on administering smaller doses of cannabinoids, saving thereby on cost. According to an embodiment, the increased therapeutic effect comprises using smaller doses of cannabinoids and still achieving at least the same beneficial result. According to an embodiment, the increased therapeutic effect comprises reduction of secondary adverse symptoms, e.g. adverse symptoms of the main illness, of ones of another illness and/or ones related to administered the product or other drugs. According to an embodiment, the increased therapeutic effect comprises reduced frequency of the conditions and/or symptoms. According to an embodiment, the increased therapeutic effect comprises reduced severity of the conditions and/or symptoms.

According to an embodiment, said enhanced therapeutic effect comprises shorter onset time of the therapeutic effect. According to an embodiment, the primary terpene, the cannabinoids and optionally secondary terpenes are present in specific amounts, and the onset time of the therapeutic effect, as measured by methods known in the art, is at least 20% shorter than that of a product comprising the same amounts of cannabinoids and secondary terpenes and one half the amount of the primary terpene, at least 30%, at least 40%, at least 50%, at least 60%, or at least 70% shorter. Shorter onset time, or differently put an earlier effect, is important particularly in cases of sublingual, edible and topical delivery and in cases where a rapid effect is desired, as in treating pain.

According to an embodiment, said enhanced therapeutic effect comprises longer onset time of the therapeutic effect. According to an embodiment, the primary terpene, the cannabinoids and optionally secondary terpenes are present in specific amounts, and the onset time of the therapeutic effect, as measured by methods known in the art, is at least 20% longer than that of a product comprising the same amounts of cannabinoids and secondary terpenes and one half the amount of the primary terpene, at least 30%, at least 40%, at least 50%, at least 60%, or at least 70% longer. According to an embodiment, products of delayed onset time are used in combination with shorter onset time to reach a sustained release effect.

According to an embodiment, said enhanced therapeutic effect comprises greater and/or increased magnitude of the therapeutic effect. According to an embodiment, the primary terpene, the cannabinoids and optionally secondary terpenes are present in specific amounts, and the magnitude of the therapeutic effect, as measured by methods known in the art, is at least 20% greater compared with that of a product comprising the same amounts of cannabinoids and secondary terpenes and one half the amount of the primary terpene, at least 30%, at least 40%, at least 50%, at least 60%, or at least 70% greater. Without wishing to be limited by any particular theory, such increased magnitude of the therapeutic effect may indicate increased bioavailability. Such increased magnitude enables achieving a desired therapeutic effect on administering smaller doses of cannabinoids, saving thereby on cost.

According to an embodiment, said enhanced therapeutic effect comprises longer and/or extended duration of the therapeutic effect. According to an embodiment, the primary terpene, the cannabinoids and optionally secondary terpenes are present in specific amounts, and the duration of the therapeutic effect, as measured by methods known in the art, is at least 20% longer compared with that of a product comprising the same amounts of cannabinoids and secondary terpenes and one half the amount of the primary terpene, at least 30%, at least 40%, at least 50%, at least 60%, at least 70%, at least 80%, at least 90% or at least 100% longer.

According to an embodiment, said enhanced therapeutic effect comprises smaller therapeutically effective amount of a product and/or reduced dosages of the product. According to an embodiment, the primary terpene, the cannabinoids and optionally secondary terpenes are present in specific amounts, and the therapeutically effective amount of the product, as measured by methods known in the art, is at least 20% smaller compared with that of a product comprising the same amounts of cannabinoids and secondary terpenes and one half the amount of the primary terpene, at least 30%, at least 40%, at least 50%, at least 60%, at least 70%, at least 80%, at least 90% or at least 100% smaller.

According to an embodiment, said enhanced therapeutic effect comprises reduced secondary adverse symptoms. According to an embodiment, the primary terpene, the cannabinoids and optionally secondary terpenes are present in specific amounts, and the secondary adverse symptoms, as measured by methods known in the art, are reduced by at least 20% compared with that of a product comprising the same amounts of cannabinoids and secondary terpenes and one half the amount of the primary terpene, by at least 30%, at least 40%, at least 50%, at least 60%, at least 70%, at least 80%, at least 90% or at least 100%.

According to an embodiment, said enhanced therapeutic effect comprises smaller and/or reduced frequency of conditions and/or symptoms. According to an embodiment, the primary terpene, the cannabinoids and optionally secondary terpenes are present in specific amounts, and the frequency of the conditions and/or symptoms, as measured by methods known in the art, is at least 20% smaller compared with that of a product comprising the same amounts of cannabinoids and secondary terpenes and one half the amount of the primary terpene, at least 30%, at least 40%, at least 50% at least 60%, at least 70%, at least 80%, or at least 90% smaller. According to an embodiment, said enhanced therapeutic effect comprises smaller and/or reduced severity of conditions and/or symptoms. According to an embodiment, the primary terpene, the cannabinoids and optionally secondary terpenes are present in specific amounts, and the severity of the conditions and/or symptoms, as measured by methods known in the art, is at least 20% smaller compared with that of a product comprising the same amounts of cannabinoids and secondary terpenes and one half the amount of the primary terpene, at least 30%, at least 40%, at least 50% at least 60%, at least 70%, at least 80%, or at least 90% smaller.

According to an embodiment, said enhanced therapeutic effect comprises smaller and/or reduced consumption of other drugs. According to an embodiment, the primary terpene, the cannabinoids and optionally secondary terpenes are present in specific amounts, and the consumption of other drugs is reduced by at least 20% compared with that of a product comprising the same amounts of cannabinoids and secondary terpenes and one half the amount of said primary terpene, reduced by at least 30%, by at least 40%, by at least 50%, by at least 60%, by at least 70%, by at least 80%, or by at least 90%.

According to an embodiment, the product comprises tetrahydrocannabinol (THC) at a concentration of less than 5% by weight, and at least 0.5% by weight primary terpene. According to an embodiment, the product is applied to a child. According to an embodiment, the primary terpene is selected from the group consisting of limonene, linalool, eucalyptol, myrcene, caryophyllene, terpineol and combinations thereof. According to an embodiment, the composition comprises tetrahydrocannabinol (THC) in a concentration of less than 5%, less than 4%, less than 3%, less than 2%, or less than 1%. According to an embodiment, the primary terpene is in a concentration of at least 0.5%, at least 0.6%, at least 0.7%, at least 0.8%, at least 0.9%, or at least 1%. According to an embodiment, the composition comprises at least 2 of said primary terpenes, at least 3, at least 4, or at least 5. According to an embodiment, the primary terpene is selected from the group consisting of limonene, linalool, myrcene and combination thereof.

According to an embodiment, the product comprises CBD and optionally THC at CBD to THC weight/weight ratio greater than 1, wherein CBD concentration is less than 20% by weight and wherein primary terpene concentration is at least 0.5% by weight. According to an embodiment, the product is applied to a child. According to an embodiment, the primary terpene is selected from the group consisting of linalool, terpineol, ocimene, humulene, caryophyllene, eucalyptol, pinene, limonene and combinations thereof. According to an embodiment, the product comprises CBD and optionally THC at CBD to THC weight/weight ratio greater 2, greater than 3, greater than 4 or greater than 5. According to an embodiment, the composition comprises cannabidiol (CBD) and/or cannabidiolic acid (CBDa) in a concentration of less than 18%, less than 16%, less than 14%, less than 12%, or less than 10%. According to an embodiment, the composition comprises cannabidiol (CBD) and/or cannabidiolic acid (CBDa), wherein CBD and/or CBDa concentration is of 10 to 20%, 10 to 15%, 15 to 20%, 12-18%. According to an embodiment, the primary terpene is in a concentration of at least 0.5%, at least 0.6%, at least 0.7%, at least 0.8%, at least 0.9%, or at least 1%. According to an embodiment, the composition comprises at least 2 of said primary terpenes, at least 3, at least 4, or at least 5. According to an embodiment, the primary terpene is selected from the group consisting of linalool, terpineol, caryophyllene and combination thereof. According to an embodiment, the primary terpene is selected from the group consisting of linalool, terpineol, ocimene and combination thereof. According to an embodiment, the primary terpene is selected from the group consisting of eucalyptol, pinene, limonene and combination thereof. According to an embodiment, the primary terpene comprises caryophyllene and/or humulene.

According to an embodiment, the therapeutic effect is generated while administering the product in a vaporizer. According to an embodiment, the therapeutic effect is generated while administering the product by inhaling. According to an embodiment, the therapeutic effect is generated while administering the product by smoking. According to an embodiment, the therapeutic effect is generated while administering the product sublingually. According to an embodiment, the therapeutic effect is generated while applying the product, topically. According to an embodiment, the therapeutic effect is generated while administering the product in suppositories, including tampons and/or rectal candles. According to an embodiment, the therapeutic effect is generated while administering the product in a spray. According to an embodiment, the therapeutic effect is generated while administering the product as an edible, as a candy, as baked good, as a drink. According to an embodiment, the therapeutic effect is generated while administering the product as vaporizer liquid nasal preparation. According to an embodiment, the therapeutic effect is generated while administering the product as micro and nano-emulsions. According to an embodiment, the therapeutic effect is generated while administering the product as micro and nano-emulsions.

According to an embodiment said therapeutic effect treats diabetes and said product comprises at least one of CBD, THC, CBC, CBG, CBN, CBL, THCV and CBDV. According to an embodiment said therapeutic effect treats diabetes and said product comprises CBD and optionally THC at CBD to THC weight/weight ratio greater than 1, greater than 2, greater than 3, greater than 4 or greater than 5. According to an embodiment said therapeutic effect treats diabetes and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats diabetes and said primary terpene is selected from the group consisting of limonene, pinene, linalool, humulene, myrcene, phytol, geraniol, bisabolol, borneol, guaiol, ocimene, fenchol, terpineol, terpinene, eucalyptol and combinations thereof. According to an embodiment, the product comprises at least 2 of these terpenes, at least 3, at least 4, or at least 5 of the terpenes. According to an embodiment, the primary terpene is selected from the group consisting of limonene, linalool, geraniol and combinations thereof. According to an embodiment, the primary terpene is selected from the group consisting of limonene, linalool, geraniol, pinene, humulene, phytol and combinations thereof. According to various embodiments said primary terpene comprises limonene, pinene, linalool, humulene, myrcene, phytol, geraniol, bisabolol, borneol, guaiol, ocimene, fenchol, terpineol, terpinene and/or eucalyptol.

According to an embodiment said therapeutic effect treats including Crohn's disease and ulcerative colitis and said product comprises at least one of CBD, THC, CBC, CBG, CBN, CBL, THCV and CBDV. According to an embodiment said therapeutic effect treats including Crohn's disease and ulcerative colitis and said product comprises CBD and optionally THC at CBD to THC weight/weight ratio greater than 1, greater than 2, greater than 3, greater than 4 or greater than 5. According to an embodiment said therapeutic effect treats including Crohn's disease and ulcerative colitis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats including Crohn's disease and ulcerative colitis and said primary terpene is selected from the group consisting of limonene, caryophyllene, borneol, myrcene, pinene, terpinene, isopulegol, phellandrene, carene, carvacol, terpineol, humulene and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, myrcene and combinations thereof. According to an embodiment, the primary terpene is selected from the group consisting of limonene, caryophyllene, myrcene, pinene, carene, carvacol and combinations thereof. According to various embodiments said primary terpene comprises limonene, caryophyllene, borneol, myrcene, pinene, terpinene, isopulegol, phellandrene, carene, carvacol, terpineol and/or humulene. According to an embodiment, said therapeutic effect treats Crohn's disease and ulcerative colitis and the product further comprises a compound selected from the group consisting of linalyl acetate, geranyl acetate, eugenol, eugenyl acetate, piperine and combinations thereof. According to an embodiment, the product includes fenchol and fenchol forms less than 5% by weight of the total terpene content.

According to an embodiment said therapeutic effect stimulates the immune system and/or treats weakened immune system and said product comprises at least one of CBD, THC, CBC, CBG, CBN, CBL, THCV and CBDV. According to an embodiment said therapeutic effect stimulates the immune system and/or treats weakened immune system and said product comprises CBD and optionally THC at CBD to THC weight/weight ratio greater than 1, greater than 2, greater than 3, greater than 4 or greater than 5. According to an embodiment said therapeutic effect stimulates the immune system and/or treats weakened immune system and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect stimulates the immune system and/or treats weakened immune system and said primary terpene is selected from the group consisting linalool, pinene, borneol, caryophyllene, geraniol, amyrin, terpinene, myrcene, eucalyptol, humulene and combinations thereof. According to an embodiment, the product comprises at least 2 of these terpenes, at least 3, at least 4, or at least 5 of the terpenes. According to an embodiment, the primary terpene is selected from the group consisting of linalool, caryophyllene, amyrin, and combinations thereof. According to an embodiment, the primary terpene is selected from the group consisting of linalool, caryophyllene, amyrin, pinene, terpinene, myrcene and combinations thereof. According to various embodiments said primary terpene comprises linalool, pinene, borneol, caryophyllene, geraniol, amyrin, terpinene, myrcene, eucalyptol and/or humulene.

According to an embodiment said therapeutic effect treats Fibromyalgia and said product comprises at least one of CBD, THC, CBC, CBG, CBN, CBL, THCV and CBDV. According to an embodiment said therapeutic effect treats Fibromyalgia and said product comprises CBD and optionally THC at CBD to THC weight/weight ratio greater than 1, greater than 2, greater than 3, greater than 4 or greater than 5. According to an embodiment said therapeutic effect treats Fibromyalgia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Fibromyalgia and said primary terpene is selected from the group consisting of linalool, caryophyllene, limonene, humulene, eucalyptol, amyrin, cycloartenol, pinene, sabinene, myrcene, terpinene, borneol, bisabolol and combinations thereof. According to an embodiment, the product comprises at least 2 of these terpenes, at least 3, at least 4, or at least 5 of the terpenes. According to an embodiment, the primary terpene is selected from the group consisting of linalool, caryophyllene, eucalyptol and combinations thereof. According to an embodiment, the primary terpene is selected from the group consisting of linalool, caryophyllene, eucalyptol, limonene, pinene, sabinene, myrcene and combinations thereof. According to various embodiments said primary terpene comprises linalool, caryophyllene, limonene, humulene, eucalyptol, amyrin, cycloartenol, pinene, sabinene, myrcene, terpinene, borneol and/or bisabolol. According to an embodiment, the product includes myrcene, humulene, bisabolol, borneol, limonene and/or linalool and myrcene, humulene, bisabolol, borneol, limonene and/or linalool forms less than 5% by weight of the total terpene content.

According to an embodiment said therapeutic effect treats nociceptive pain and said product comprises at least one of CBD, THC, CBC, CBG, CBN, CBL, THCV and CBDV. According to an embodiment said therapeutic effect treats nociceptive pain and said product comprises CBD and optionally THC at CBD to THC weight/weight ratio greater than 1, greater than 2, greater than 3, greater than 4 or greater than 5. According to an embodiment said therapeutic effect treats nociceptive pain and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats nociceptive pain and said primary terpene is selected from the group consisting of myrcene, linalool, caryophyllene, eucalyptol, cycloartenol, borneol, sabinene, camphene, terpineol, citronellol, geraniol, humulene, bisabolol, limonene and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, eucalyptol, terpineol, citronellol and combinations thereof. According to various embodiments said primary terpene comprises myrcene, linalool, caryophyllene, eucalyptol, cycloartenol, borneol, sabinene, camphene, terpineol, citronellol, geraniol, humulene, bisabolol and/or limonene.

According to an embodiment said therapeutic effect treats neuropathic pain and said product comprises at least one of CBD, THC, CBC, CBG, CBN, CBL, THCV and CBDV. According to an embodiment said therapeutic effect treats neuropathic pain and said product comprises CBD and optionally THC at CBD to THC weight/weight ratio greater than 1, greater than 2, greater than 3, greater than 4 or greater than 5. According to an embodiment said therapeutic effect treats neuropathic pain and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats neuropathic pain and said primary terpene is selected from the group consisting of caryophyllene, linalool, eucalyptol, amyrin, borneol, pinene, terpineol, limonene, nerolidol, geraniol, myrcene and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, eucalyptol and combinations thereof. According to an embodiment, the primary terpene is selected from the group consisting of caryophyllene, linalool, eucalyptol, borneol, limonene, myrcene and combinations thereof. According to an embodiment, the primary terpene is selected from the group consisting of pinene, terpineol, nerolidol and combinations thereof. According to various embodiments said primary terpene comprises caryophyllene, linalool, eucalyptol, amyrin, borneol, pinene, terpineol, limonene, nerolidol, geraniol and/or myrcene. According to an embodiment, the product includes humulene, bisabolol, borneol, limonene and/or linalool, and humulene, bisabolol, borneol, limonene and/or linalool forms less than 5% by weight of the total terpene content.

According to an embodiment said therapeutic effect treats pain and said product comprises at least one of CBD, THC, CBC, CBG, CBN, CBL, THCV and CBDV. According to an embodiment said therapeutic effect treats pain and said product comprises CBD and optionally THC at CBD to THC weight/weight ratio greater than 1, greater than 2, greater than 3, greater than 4 or greater than 5. According to an embodiment said therapeutic effect treats pain and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats pain and said primary terpene is selected from the group consisting of myrcene, linalool, humulene, eucalyptol, caryophyllene, caryophyllene oxide, amyrin, cycloartenol, borneol, sabinene, camphene, nerolidol, terpineol, geraniol, citronellol, camphor, bisabolol, limonene and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, eucalyptol, borneol, terpineol and combinations thereof. According to various embodiments said primary terpene comprises myrcene, linalool, humulene, eucalyptol, caryophyllene, caryophyllene oxide, amyrin, cycloartenol, borneol, sabinene, camphene, nerolidol, terpineol, geraniol, citronellol, camphor, bisabolol and/or limonene. According to an embodiment, said therapeutic effect treats pain and the product comprises a compound selected from the group consisting of linalyl acetate, geranyl acetate, eugenol, eugenyl acetate, piperine, methylis-oeugenol, Methyleugenol, menthol and combination thereof. According to an embodiment, the product includes humulene, bisabolol, borneol, limonene and/or linalool, wherein humulene, bisabolol, borneol, limonene and/or linalool forms less than 5% by weight of the total terpene content.

According to an embodiment said therapeutic effect treats arm or leg pain and said product comprises at least one of CBD, THC, CBC, CBG, CBN, CBL, THCV and CBDV. According to an embodiment said therapeutic effect treats arm or leg pain and said product comprises CBD and optionally THC at CBD to THC weight/weight ratio greater than 1, greater than 2, greater than 3, greater than 4 or greater than 5. According to an embodiment said therapeutic effect treats arm or leg pain and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats arm or leg pain and said primary terpene is selected from the group consisting of linalool, terpinene, pinene, limonene, terpineol, myrcene, nerolidol and combinations thereof. According to an embodiment, the product comprises at least 2 of these terpenes, at least 3, at least 4, or at least 5 of the terpenes. According to an embodiment, the primary terpene is selected from the group consisting of linalool, pinene, myrcene and combinations thereof. According to an embodiment, the primary terpene is selected from the group consisting of linalool, pinene, myrcene, limonene, terpineol, nerolidol and combinations thereof. According to various embodiments said primary terpene comprises linalool, terpinene, pinene, limonene, terpineol, myrcene and/or nerolidol.

According to an embodiment said therapeutic effect treats neurodegenerative diseases including Alzheimer disease, Parkinson disease, Huntington's disease, dystonia and/or Amyotrophic lateral sclerosis (ALS) and said product comprises at least one of CBD, THC, CBC, CBG, CBN, CBL, THCV and CBDV. According to an embodiment said therapeutic effect treats neurodegenerative diseases including Alzheimer disease, Parkinson disease, Huntington's disease, dystonia and/or Amyotrophic lateral sclerosis (ALS) and said product comprises CBD and optionally THC at CBD to THC weight/weight ratio greater than 1, greater than 2, greater than 3, greater than 4 or greater than 5. According to an embodiment said therapeutic effect treats neurodegenerative diseases including Alzheimer disease, Parkinson disease, Huntington's disease, dystonia and/or Amyotrophic lateral sclerosis (ALS) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats neurodegenerative diseases including Alzheimer disease, Parkinson disease, Huntington's disease, dystonia and/or Amyotrophic lateral sclerosis (ALS) and said primary terpene is selected from the group consisting of terpineol, carvophyllene, myrcene, terpineol, linalool, humulene, eucalyptol, pinene, pulegone, cumene, ocimene, limonene, nerolidol, sabinene, carene, citronellol, geraniol, menthol, borneol, terpinene, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, pinene, terpineol and combinations thereof. According to an embodiment, the primary terpene is selected from the group consisting of caryophyllene, linalool, pinene, terpineol, myrcene, terpineol, limonene, nerolidol, sabinene and combinations thereof. According to various embodiments said primary terpene comprises terpineol, caryophyllene, myrcene, terpineol, linalool, humulene, eucalyptol, pinene, pulegone, cymene, ocimene, limonene, nerolidol, sabinene, carene, citronellol, geraniol, menthol, borneol, terpinene, bisabolol and/or fenchol. According to an embodiment said therapeutic effect treats Alzheimer disease and said the primary terpene is selected from the group consisting of pinene, eucalyptol, linalool, terpineol, myrcene, caryophyllene and combinations thereof. According to an embodiment said therapeutic effect treats Alzheimer disease and said primary terpene is selected from the group consisting of pinene, eucalyptol, linalool and combinations thereof. According to an embodiment said therapeutic effect treats Parkinson disease, Huntington's disease, dystonia and/or Amyotrophic lateral sclerosis (ALS) and said primary terpene is selected from the group consisting caryophyllene, myrcene, linalool, pinene, limonene, nerolidol, sabinene, terpineol and combinations thereof. According to an embodiment said therapeutic effect treats Parkinson disease, Huntington's disease, dystonia and/or Amyotrophic lateral sclerosis (ALS) and said primary terpene is selected from the group consisting myrcene, linalool, pinene, nerolidol and combinations thereof. According to an embodiment, said therapeutic effect treats neurodegenerative diseases including Alzheimer, Parkinson disease, Huntington's disease, dystonia and/or Amyotrophic lateral sclerosis (ALS) and the product comprises a compound selected from the group consisting of linalyl acetate, geranyl acetate, menthol, piperine, eugenol, citronellyl formate, jasmone, benzy acetate, benzyl alcohol and combination thereof. According to an embodiment, the product includes pinene, myrcene and/or terpineol, and pinene, myrcene and/or terpineol forms less than 5% by weight of the total terpene content.

According to an embodiment said therapeutic effect treats multiple sclerosis and said product comprises at least one of CBD, THC, CBC, CBG, CBN, CBL, THCV and CBDV. According to an embodiment said therapeutic effect treats multiple sclerosis and said product comprises CBD and optionally THC at CBD to THC weight/weight ratio greater than 1, greater than 2, greater than 3, greater than 4 or greater than 5. According to an embodiment said therapeutic effect treats multiple sclerosis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats multiple sclerosis and said primary terpene is selected from the group consisting of caryophyllene, pinene, myrcene, limonene, humulene, citronellol, eucalyptol, caryophyllene oxide, linalool, amyrin, cycloartenol, cymene, terpinene, borneol, pulegol, nerolidol, terpineol, sabinene, geraniol and combinations thereof. According to an embodiment, the product comprises at least 2 of these terpenes, at least 3, at least 4, or at least 5 of the terpenes. According to an embodiment, the primary terpene is selected from the group consisting of caryophyllene, myrcene, linalool and combinations thereof. According to an embodiment, the primary terpene is selected from the group consisting of caryophyllene, myrcene, linalool, pinene, limonene, eucalyptol and combinations thereof. According to various embodiments said primary terpene comprises caryophyllene, pinene, myrcene, limonene, humulene, citronellol, eucalyptol, caryophyllene oxide, linalool, amyrin, cycloartenol, cymene, terpinene, borneol, pulegol, nerolidol, terpineol, sabinene and/or geraniol.

According to an embodiment said therapeutic effect treats Myasthenia gravis and said product comprises at least one of CBD, THC, CBC, CBG, CBN, CBL, THCV and CBDV. According to an embodiment said therapeutic effect treats Myasthenia gravis and said product comprises CBD and optionally THC at CBD to THC weight/weight ratio greater than 1, greater than 2, greater than 3, greater than 4 or greater than 5. According to an embodiment said therapeutic effect treats Myasthenia gravis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Myasthenia gravis and said primary terpene is selected from the group consisting of pinene, terpineol, eucalyptol, pulegone, cymene, ocimene, nerolidol, limonene, linalool, citronellol, geraniol, menthol, caryophyllene, borneol and combinations thereof. According to an embodiment, the product comprises at least 2 of these terpenes, at least 3, at least 4, or at least 5 of the terpenes. According to an embodiment, the primary terpene is selected from the group consisting of terpineol, eucalyptol, linalool and combinations thereof. According to an embodiment, the primary terpene is selected from the group consisting of terpineol, eucalyptol, linalool, pinene, nerolidol, limonene and combinations thereof. According to various embodiments said primary terpene comprises pinene, terpineol, eucalyptol, pulegone, cymene, ocimene, nerolidol, limonene, linalool, citronellol, geraniol, menthol, caryophyllene, and/or borneol. According to an embodiment, the product includes myrcene and/or pinene, and myrcene and/or pinene forms less than 5% by weight of the total terpene content.

According to an embodiment said therapeutic effect treats epilepsy and said product comprises at least one of CBD, THC, CBC, CBG, CBN, CBL, THCV and CBDV. According to an embodiment said therapeutic effect treats epilepsy and said product comprises CBD and optionally THC at CBD to THC weight/weight ratio greater than 1, greater than 2, greater than 3, greater than 4 or greater than 5. According to an embodiment said therapeutic effect treats epilepsy and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats epilepsy and said primary terpene is selected from the group consisting of linalool, terpineol, ocimene, myrcene, limonene, caryophyllene and combinations thereof. According to an embodiment, the product comprises at least 2 of these terpenes, at least 3, at least 4, or at least 5 of the terpenes. According to an embodiment, the primary terpene is selected from the group consisting of linalool, terpineol, ocimene and combinations thereof. According to various embodiments said primary terpene comprises linalool, terpineol, ocimene, myrcene, limonene and/or caryophyllene.

According to an embodiment said therapeutic effect treats cancer and/or cancer related symptom and said product comprises at least one of CBD, THC, CBC, CBG, CBN, CBL, THCV and CBDV. According to an embodiment said therapeutic effect treats cancer and/or cancer related symptom and said product comprises CBD and optionally THC at CBD to THC weight/weight ratio greater than 1, greater than 2, greater than 3, greater than 4 or greater than 5. According to an embodiment said therapeutic effect treats cancer and/or cancer related symptom and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats cancer and/or cancer related symptom and said primary terpene is selected from the group consisting of myrcene, limonene, caryophyllene, caryophyllene oxide, terpinene, citronellol, linalool, geraniol. Menthol. humulene, amyrin, cycloartenol, pinene, camphene, eucalyptol, terpineol, borneol and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, linalool and combinations thereof. According to an embodiment, the primary terpene is selected from the group consisting of limonene, caryophyllene, linalool, citronellol, myrcene, eucalyptol, pinene and combinations thereof. According to various embodiments said primary terpene comprises myrcene, limonene, caryophyllene, caryophyllene oxide, terpinene, citronellol, linalool, geraniol, menthol, humulene, amyrin, cycloartenol, pinene, camphene, eucalyptol, terpineol and/or borneol. According to an embodiment, said therapeutic effect treats cancer and/or cancer related symptom and the product comprises a compound selected from the group consisting of linalyl acetate, geranyl acetate, eugenol, eugenyl acetate, piperine, methylis-oeugenol, Methyleugenol, menthol and combination thereof.

According to an embodiment said therapeutic effect treats stroke and/or traumatic brain injury and said product comprises at least one of CBD, THC, CBC, CBG, CBN, CBL, THCV and CBDV. According to an embodiment said therapeutic effect treats stroke and/or traumatic brain injury and said product comprises CBD and optionally THC at CBD to THC weight/weight ratio greater than 1, greater than 2, greater than 3, greater than 4 or greater than 5. According to an embodiment said therapeutic effect treats stroke and/or traumatic brain injury and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats stroke and/or traumatic brain injury and said primary terpene is selected from the group consisting of myrcene, terpinene, caryophyllene, caryophyllene oxide, pinene, limonene, humulene, citronellol, eucalyptol, linalool, amyrin, cycloartenol, terpineol, thymol, eucalyptol, geraniol, carvacrol, thymol, cardinol, menth-2-en-1-ol, carotol and combinations thereof. According to an embodiment, the product comprises at least 2 of these terpenes, at least 3, at least 4, or at least 5 of the terpenes. According to an embodiment, the primary terpene is selected from the group consisting of myrcene, caryophyllene, limonene and combinations thereof. According to an embodiment, the primary terpene is selected from the group consisting of myrcene, caryophyllene, limonene, pinene, humulene, terpineol, thymol, eucalyptol and combinations thereof. According to various embodiments said primary terpene comprises myrcene, terpinene, caryophyllene, caryophyllene oxide, pinene, limonene, humulene, citronellol, eucalyptol, linalool, amyrin, cycloartenol, terpineol, thymol, eucalyptol, geraniol, carvacrol, thymol, cardinol, menth-2-en-1-ol and/or carotol. According to an embodiment, the product includes fenchol and/or borneol, and fenchol and/or borneol forms less than 5% by weight of the total terpene content.

According to an embodiment said therapeutic effect treats addiction, including addiction to drugs, smoking, drinks, food, gambling, sex, and sports and said product comprises at least one of CBD, THC, CBC, CBG, CBN, CBL, THCV and CBDV. According to an embodiment said therapeutic effect treats addiction, including addiction to drugs, smoking, drinks, food, gambling, sex, and sports and said product comprises CBD and optionally THC at CBD to THC weight/weight ratio greater than 1, greater than 2, greater than 3, greater than 4 or greater than 5. According to an embodiment said therapeutic effect treats addiction, including addiction to drugs, smoking, drinks, food, gambling, sex, and sports and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats addiction, including addiction to drugs, smoking, drinks, food, gambling, sex, and sports and said primary terpene is selected from the group consisting of caryophyllene, pinene, myrcene, limonene, linalool, terpineol and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, terpineol and combinations thereof. According to various embodiments said primary terpene comprises caryophyllene, pinene, myrcene, limonene, linalool and/or terpineol.

According to an embodiment said therapeutic effect treats inflammatory airway diseases including asthma and/or chronic obstructive pulmonary disease (COPD) and said product comprises at least one of CBD, THC, CBC, CBG, CBN, CBL, THCV and CBDV. According to an embodiment said therapeutic effect treats inflammatory airway diseases including asthma and/or chronic obstructive pulmonary disease (COPD) and said product comprises CBD and optionally THC at CBD to THC weight/weight ratio greater than 1, greater than 2, greater than 3, greater than 4 or greater than 5. According to an embodiment said therapeutic effect treats inflammatory airway diseases including asthma and/or chronic obstructive pulmonary disease (COPD) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats inflammatory airway diseases including asthma and/or chronic obstructive pulmonary disease (COPD) and said primary terpene is selected from the group consisting of pinene, eucalyptol, limonene, humulene, camphene, caryophyllene and combinations thereof. According to an embodiment, the product comprises at least 2 of these terpenes, at least 3, at least 4, or at least 5 of the terpenes. According to an embodiment, the primary terpene is selected from the group consisting of pinene, eucalyptol, humulene, and combinations thereof. According to various embodiments said primary terpene comprises pinene, eucalyptol, limonene, humulene, camphene and/or caryophyllene.

According to an embodiment said therapeutic effect treats cerebral palsy (CP) and said product comprises at least one of CBD, THC, CBC, CBG, CBN, CBL, THCV and CBDV. According to an embodiment said therapeutic effect treats cerebral palsy (CP) and said product comprises CBD and optionally THC at CBD to THC weight/weight ratio greater than 1, greater than 2, greater than 3, greater than 4 or greater than 5. According to an embodiment said therapeutic effect treats cerebral palsy (CP) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats cerebral palsy (CP) and said primary terpene is selected from the group consisting of myrcene, pinene, linalool, humulene, nerolidol, limonene, terpineol, sabinene and combinations thereof. According to an embodiment, the product comprises at least 2 of these terpenes, at least 3, at least 4, or at least 5 of the terpenes. According to an embodiment, the primary terpene is selected from the group consisting of myrcene, pinene, nerolidol and combinations thereof. According to an embodiment, the primary terpene is selected from the group consisting of linalool, limonene, sabinene and combinations thereof. According to various embodiments said primary terpene comprises myrcene, pinene, linalool, humulene, nerolidol, limonene, terpineol and/or sabinene.

According to an embodiment said therapeutic effect treats autism and/or autism spectrum disorder and said product comprises at least one of CBD, THC, CBC, CBG, CBN, CBL, THCV and CBDV. According to an embodiment said therapeutic effect treats autism and/or autism spectrum disorder and said product comprises CBD and optionally THC at CBD to THC weight/weight ratio greater than 1, greater than 2, greater than 3, greater than 4 or greater than 5. According to an embodiment said therapeutic effect treats autism and/or autism spectrum disorder and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats autism and/or autism spectrum disorder and said primary terpene is selected from the group consisting of limonene, caryophyllene, pinene, myrcene, humulene, citronellol, eucalyptol, linalool, terpineol, ocimene, geraniol, menthol, borneol, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of pinene, eucalyptol, linalool and combinations thereof. According to an embodiment, the primary terpene is selected from the group consisting of pinene, eucalyptol, linalool, caryophyllene, myrcene, terpineol and combinations thereof. According to various embodiments said primary terpene comprises limonene, caryophyllene, pinene, myrcene, humulene, citronellol, eucalyptol, linalool, terpinenol, ocimene, geraniol, menthol, borneol, bisabolol and/or fenchol.

According to an embodiment said therapeutic effect treats hyperactivity disorder (ADHD), attention deficit disorder (ADD) and/or obsessive-compulsive disorder (OCD) and said product comprises at least one of CBD, THC, CBC, CBG, CBN, CBL, THCV and CBDV. According to an embodiment said therapeutic effect treats hyperactivity disorder (ADHD), attention deficit disorder (ADD) and/or obsessive-compulsive disorder (OCD) and said product comprises CBD and optionally THC at CBD to THC weight/weight ratio greater than 1, greater than 2, greater than 3, greater than 4 or greater than 5. According to an embodiment said therapeutic effect treats hyperactivity disorder (ADHD), attention deficit disorder (ADD) and/or obsessive-compulsive disorder (OCD) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats hyperactivity disorder (ADHD), attention deficit disorder (ADD) and/or obsessive-compulsive disorder (OCD) and said primary terpene is selected from the group consisting of linalool, eucalyptol, terpineol, myrcene, pinene, pulegone, caryophyllene, geraniol, citronellol, menthol, caryophyllene, pinene, borneol, bisabolol, fenchol and combinations thereof. According to an embodiment, the product comprises at least 2 of these terpenes, at least 3, at least 4, or at least 5 of the terpenes. According to an embodiment said therapeutic effect treats hyperactivity disorder (ADHD) and/or attention deficit disorder (ADD) and said primary terpene is selected from the group consisting of linalool, eucalyptol, myrcene, and combinations thereof. According to an embodiment, the primary terpene is selected from the group consisting of linalool, eucalyptol, myrcene, caryophyllene, pinene, borneol and combinations thereof. According to an embodiment said therapeutic effect treats obsessive-compulsive disorder (OCD) and said primary terpene is selected from the group consisting of limonene, eucalyptol, pinene and combination thereof. According to an embodiment, the primary terpene is selected from the group consisting of linalool, caryophyllene, borneol and combination thereof. According to various embodiments said primary terpene comprises linalool, eucalyptol, terpineol, myrcene, pinene, pulegone, caryophyllene, geraniol, citronellol, menthol, caryophyllene, pinene, borneol, bisabolol and/or fenchol.

According to an embodiment said therapeutic effect treats Tourette syndrome, motor spasms, motor tics and/or vocal tics and said product comprises at least one of CBD, THC, CBC, CBG, CBN, CBL, THCV and CBDV. According to an embodiment said therapeutic effect treats Tourette syndrome, motor spasms, motor tics and/or vocal tics and said product comprises CBD and optionally THC at CBD to THC weight/weight ratio greater than 1, greater than 2, greater than 3, greater than 4 or greater than 5. According to an embodiment said therapeutic effect treats Tourette syndrome, motor spasms, motor tics and/or vocal tics and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Tourette syndrome, motor spasms, motor tics and/or vocal tics and said primary terpene is selected from the group consisting of myrcene, linalool, limonene, pinene, nerolidol, caryophyllene, eucalyptol, geraniol, menthol, borneol, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of myrcene, limonene, nerolidol and combinations thereof. According to an embodiment, the primary terpene is selected from the group consisting of linalool, pinene, eucalyptol and combinations thereof. According to various embodiments said primary terpene comprises myrcene, linalool, limonene, pinene, nerolidol, caryophyllene, eucalyptol, geraniol, menthol, borneol, bisabolol and/or fenchol.

According to an embodiment said therapeutic effect treats psoriasis and said product comprises at least one of CBD, THC, CBC, CBG, CBN, CBL, THCV and CBDV. According to an embodiment said therapeutic effect treats psoriasis and said product comprises CBD and optionally THC at CBD to THC weight/weight ratio greater than 1, greater than 2, greater than 3, greater than 4 or greater than 5. According to an embodiment said therapeutic effect treats psoriasis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats psoriasis and said primary terpene is selected from the group consisting of linalool, caryophyllene, limonene and combinations thereof. According to an embodiment, the product comprises at least 2 of these terpenes or all 3 of the terpenes. According to an embodiment, the primary terpene is selected from the group consisting of linalool, caryophyllene, limonene and combinations thereof. According to various embodiments said primary terpene comprises linalool, caryophyllene and/or limonene.

According to an embodiment said therapeutic effect treats dermatophytes and said product comprises at least one of CBD, THC, CBC, CBG, CBN, CBL, THCV and CBDV. According to an embodiment said therapeutic effect treats dermatophytes and said product comprises CBD and optionally THC at CBD to THC weight/weight ratio greater than 1, greater than 2, greater than 3, greater than 4 or greater than 5. According to an embodiment said therapeutic effect treats dermatophytes and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats dermatophytes and said primary terpene is selected from the group consisting of limonene, caryophyllene, caryophyllene oxide, nerolidol, eucalyptol, terpinene, cycloartenol, amyrin, campene and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, caryophyllene oxide and combinations thereof. According to an embodiment, the primary terpene is selected from the group consisting of limonene, caryophyllene, caryophyllene oxide, nerolidol, eucalyptol, terpinene and combinations thereof. According to various embodiments said primary terpene comprises limonene, caryophyllene, caryophyllene oxide, nerolidol, eucalyptol, terpinene, cycloartenol, amyrin and/or campene.

According to an embodiment said therapeutic effect treats *candida* infection and said product comprises at least one of CBD, THC, CBC, CBG, CBN, CBL, THCV and CBDV. According to an embodiment said therapeutic effect treats *candida* infection and said product comprises CBD and optionally THC at CBD to THC weight/weight ratio greater than 1, greater than 2, greater than 3, greater than 4 or greater than 5. According to an embodiment said therapeutic effect treats *candida* infection and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats *candida* infection and said primary terpene is selected from the group consisting of pinene, limonene, caryophyllene, caryophyllene oxide, nerolidol, eucalyptol, terpinene, terpineol, myrcene, cycloartenol, citronellol, amyrin, camphene, cymene, Ocimene, humulene, farnesene, guaiol, eudesmol, friedelin, linalool, camphor, menthol, thymol, carvacrol, eugenol, farnesol, citronellol, geraniol, citral, ionone and combinations thereof. According to an embodiment, the product comprises at least 2 of these terpenes, at least 3, at least 4, or at least 5 of the terpenes. According to an embodiment, the primary terpene is selected from the group consisting of thymol, carvacrol, eugenol and combinations thereof. According to an embodiment, the primary terpene is selected from the group consisting of thymol, carvacrol, eugenol, nerolidol, linalool, farnesol, citronellol, geraniol, citral and combinations thereof. According to various embodiments said primary terpene comprises pinene, limonene, caryophyllene, caryophyllene oxide, nerolidol, eucalyptol, terpinene, terpineol, myrcene, cycloartenol, citronellol, amyrin, camphene, cymene, Ocimene, humulene, farnesene, guaiol, eudesmol, friedelin, linalool, camphor, menthol, thymol, carvacrol, eugenol, farnesol, citronellol, geraniol, citral and/or ionone.

According to an embodiment said therapeutic effect treats leishmaniasis and said product comprises at least one of CBD, THC, CBC, CBG, CBN, CBL, THCV and CBDV. According to an embodiment said therapeutic effect treats leishmaniasis and said product comprises CBD and optionally THC at CBD to THC weight/weight ratio greater than 1, greater than 2, greater than 3, greater than 4 or greater than 5. According to an embodiment said therapeutic effect treats leishmaniasis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats leishmaniasis and said primary terpene is selected from the group consisting of linalool, nerolidol, pinene, caryophyllene and/or eucalyptol. According to an embodiment said primary terpene is linalool and/or nerolidol.

According to an embodiment said therapeutic effect treats Methycillin-resistant *Staphylococcus aureus* (MRSA) and said product comprises at least one of CBD, THC, CBC, CBG, CBN, CBL, THCV and CBDV. According to an embodiment said therapeutic effect treats Methycillin-resistant *Staphylococcus aureus* (MRSA) and said product comprises CBD and optionally THC at CBD to THC weight/weight ratio greater than 1, greater than 2, greater than 3, greater than 4 or greater than 5. According to an embodiment said therapeutic effect treats Methycillin-resistant *Staphylococcus aureus* (MRSA) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Methycillin-resistant *Staphylococcus aureus* (MRSA) and said primary terpene is selected from the group consisting of pinene, caryophyllene, caryophyllene oxide, limonene, nerolidol, cycloartenol, amyrin and combinations thereof. According to an embodiment, the product comprises at least 2 of these terpenes, at least 3, at least 4, or at least 5 of the terpenes. According to an embodiment, the primary terpene is selected from the group consisting of pinene, caryophyllene, limonene, amyrin and combinations thereof. According to various embodiments said primary terpene comprises pinene, caryophyllene, caryophyllene oxide, limonene, nerolidol, cycloartenol and/or amyrin.

According to an embodiment said therapeutic effect treats malaria and said product comprises at least one of CBD, THC, CBC, CBG, CBN, CBL, THCV and CBDV. According to an embodiment said therapeutic effect treats malaria and said product comprises CBD and optionally THC at CBD to THC weight/weight ratio greater than 1, greater than 2, greater than 3, greater than 4 or greater than 5. According to an embodiment said therapeutic effect treats malaria and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats malaria and said primary terpene is selected from the group consisting of caryophyllene, nerolidol, pinene, eucalyptol, limonene and combinations thereof. According to an embodiment, the product comprises at least 2 of these terpenes, at least 3, at least 4, or at least 5 of the terpenes. According to an embodiment, the primary terpene is selected from the group consisting of caryophyllene, nerolidol, pinene and combinations thereof. According to various embodiments said primary terpene comprises caryophyllene, nerolidol, pinene, eucalyptol and/or limonene.

According to an embodiment said therapeutic effect treats acne and said product comprises at least one of CBD, THC, CBC, CBG, CBN, CBL, THCV and CBDV. According to an embodiment said therapeutic effect treats acne and said product comprises CBD and optionally THC at CBD to THC weight/weight ratio greater than 1, greater than 2, greater than 3, greater than 4 or greater than 5. According to an embodiment said therapeutic effect treats acne) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats acne and said primary terpene is selected from the group consisting of limonene, linalool, nerolidol, pinene, terpineol and combinations thereof. According to an embodiment, the product comprises at least 2 of these terpenes, at least 3, at least 4, or all 5 of the terpenes. According to an embodiment, the primary terpene is selected from the group consisting of limonene, pinene, terpineol and combinations thereof. According to various embodiments said primary terpene comprises limonene, linalool, nerolidol, pinene and/or terpineol.

According to an embodiment said therapeutic effect treats allergy and said product comprises at least one of CBD, THC, CBC, CBG, CBN, CBL, THCV and CBDV. According to an embodiment said therapeutic effect treats allergy and said product comprises CBD and optionally THC at CBD to THC weight/weight ratio greater than 1, greater than 2, greater than 3, greater than 4 or greater than 5. According to an embodiment said therapeutic effect treats allergy and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats allergy and said primary terpene is selected from the group consisting of camphene, pinene, borneol, caryophyllene, geraniol and combinations thereof. According to an embodiment, the product comprises at least 2 of these terpenes, at least 3, at least 4, or all 5 of the terpenes. According to an embodiment, the primary terpene is selected from the group consisting of camphene, pinene, caryophyllene and combinations thereof. According to various embodiments said primary terpene comprises camphene, pinene, borneol, caryophyllene and/or geraniol.

According to an embodiment said therapeutic effect treats osteoporosis and said product comprises at least one of CBD, THC, CBC, CBG, CBN, CBL, THCV and CBDV. According to an embodiment said therapeutic effect treats osteoporosis and said product comprises CBD and optionally THC at CBD to THC weight/weight ratio greater than 1, greater than 2, greater than 3, greater than 4 or greater than 5. According to an embodiment said therapeutic effect treats osteoporosis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats osteoporosis and said the primary terpene is selected from the group consisting of caryophyllene, caryophyllene oxide, carene, eucalyptol, sabinene, pinene, limonene, borneol, thymol, camphor and combinations thereof. According to an embodiment, the product comprises at least 2 of these terpenes, at least 3, at least 4, or at least 5 of the terpenes. According to an embodiment, the primary terpene is selected from the group consisting of caryophyllene, carene, camphor and combinations thereof. According to an embodiment, the primary terpene is selected from the group consisting of caryophyllene, carene, camphor, pinene, limonene, borneol and combinations thereof. According to various embodiments said primary terpene comprises caryophyllene oxide, eucalyptol, sabinene, pinene, limonene, thymol and/or camphor. According to an embodiment, said therapeutic effect treats osteoporosis and the product further comprises a compound selected from the group consisting of biochanin A, formononetin, genistein, daidzein, glycitein, prenylnaringenin, diosgenin, acetin, cimicifugoside and combinations thereof.

According to an embodiment said therapeutic effect treats sleep disorder and/or insomnia and said product comprises at least one of CBD, THC, CBC, CBG, CBN, CBL, THCV and CBDV. According to an embodiment said therapeutic effect treats sleep disorder and/or insomnia and said product comprises CBD and optionally THC at CBD to THC weight/weight ratio greater than 1, greater than 2, greater than 3, greater than 4 or greater than 5. According to an embodiment said therapeutic effect treats sleep disorder and/or insomnia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats sleep disorder and/or insomnia and said the primary terpene is selected from the group consisting of linalool, caryophyllene, myrcene, terpineol, terpinene, citronellol, eucalyptol, nerolidol, sabinene, pinene, limonene, borneol, fenchol, bisabolol humulene, phytol, citral and combinations thereof. According to an embodiment, the product comprises at least 2 of these terpenes, at least 3, at least 4, or at least 5 of the terpenes. According to an embodiment, the primary terpene is selected from the group consisting of linalool, terpineol, myrcene and combinations thereof. According to an embodiment, the primary terpene is selected from the group consisting of linalool, terpineol, myrcene, caryophyllene, terpinene, borneol and combinations thereof. According to an embodiment, the primary terpene comprises terpineol, citronellol and/or linalool. According to various embodiments said primary terpene comprises terpineol, terpinene, citronellol, eucalyptol, nerolidol, sabinene, pinene, limonene, borneol, fenchol, bisabolol, phytol and/or humulene. According to an embodiment, said therapeutic effect treats sleep disorder and/or insomnia and the product further comprises a compound selected from the group consisting of linalyl acetate and/or chamazulene. According to an embodiment, the product includes caryophyllene, and caryophyllene forms less than 5% by weight of the total terpene content.

According to an embodiment said therapeutic effect treats anxiety, irritability, nervousness, restless, stress, depression, general discomfort, mood problems and/or affect disorder and said product comprises at least one of CBD, THC, CBC, CBG, CBN, CBL, THCV and CBDV. According to an embodiment said therapeutic effect treats anxiety, irritability, nervousness, restless, stress, depression, general discomfort, mood problems and/or affect disorder and said product comprises CBD and optionally THC at CBD to THC weight/weight ratio greater than 1, greater than 2, greater than 3, greater than 4 or greater than 5. According to an embodiment said therapeutic effect treats anxiety, irritability, nervousness, restless, stress, depression, general discomfort, mood problems and/or affect disorder and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats anxiety, irritability, nervousness, restless, stress, depression, general discomfort, mood problems and/or affect disorder and said the primary terpene is selected from the group consisting of limonene, linalool, terpineol, citronellol, eucalyptol, caryophyllene, geraniol, menthol, iso-menthone, germacrene, pinene, citronellol, cardinol, neral, geranial, myrcene, terpinene, menth-2-en-1-ol, humulene, bisabolol, borneol, fenchol, nerolidol, phellandrene and combinations thereof. According to an embodiment, the product comprises at least 2 of these terpenes, at least 3, at least 4, or at least 5 of the terpenes. According to an embodiment, the primary terpene is selected from the group consisting of limonene, linalool, eucalyptol and combinations thereof. According to an embodiment, the primary terpene is selected from the group consisting of limonene, linalool, eucalyptol, terpineol, caryophyllene, pinene, myrcene and combinations thereof. According to an embodiment, the primary terpene is selected from the group consisting of limonene, linalool, caryophyllene, bisabolol and combinations thereof. According to an embodiment, the primary terpene is selected from the group consisting of limonene, linalool, pinene, humulene and combinations thereof. According to various embodiments said primary terpene comprises terpineol, citronellol, caryophyllene, geraniol, menthol, iso-menthone, germacrene, pinene, citronellol, cardinol, neral, geranial, myrcene, terpinene, menth-2-en-1-ol, humulene, bisabolol, borneol, nerolidol phellandrene and/or fenchol. According to an embodiment, said therapeutic effect treats anxiety, irritability, nervousness, restless, stress, depression, general discomfort, mood problems and/or affect disorder and the product further comprises a compound selected from the group consisting of linalyl acetate, geranyl acetate, menthol, piperine, eugenol, citronellyl formate, jasmone, benzy acetate, benzyl alcohol and combinations thereof. According to an embodiment, the product includes bisabolol, nerolidol, terpinene, myrcene and/or pinene bisabolol, nerolidol, terpinene, myrcene and/or pinene, and bisabolol, nerolidol, terpinene and/or pinene forms less than 5% by weight of the total terpene content.

According to an embodiment said therapeutic effect treats difficulty in concentration, memory loss, and/or dementia and said product comprises at least one of CBD, THC, CBC, CBG, CBN, CBL, THCV and CBDV. According to an embodiment said therapeutic effect treats difficulty in concentration, memory loss, and/or dementia and said product comprises CBD and optionally THC at CBD to THC weight/weight ratio greater than 1, greater than 2, greater than 3, greater than 4 or greater than 5. According to an embodiment said therapeutic effect treats difficulty in concentration, memory loss, and/or dementia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats difficulty in concentration, memory loss, and/or dementia and said the primary terpene is selected from the group consisting of pinene, pulegone, eucalyptol, terpineol, cymene, ocimene, limonene, linalool, caryophyllene, humulene, carene and combinations thereof. According to an embodiment, the product comprises at least 2 of these terpenes, at least 3, at least 4, or at least 5 of the terpenes. According to an embodiment, the primary terpene is selected from the group consisting of eucalyptol, pinene, limonene and combinations thereof. According to an embodiment, the primary terpene is selected from the group consisting of eucalyptol, pinene, limonene, terpineol, humulene, carene and combinations thereof. According to various embodiments said primary terpene comprises pinene, pulegone, eucalyptol, terpineol, cymene, ocimene, limonene, linalool, caryophyllene, humulene and/or carene.

According to an embodiment said therapeutic effect treats muscle pain, myalgia, spasticity, muscle tension, cramps and/or spasms and said product comprises at least one of CBD, THC, CBC, CBG, CBN, CBL, THCV and CBDV. According to an embodiment said therapeutic effect treats muscle pain, myalgia, spasticity, muscle tension, cramps and/or spasms and said product comprises CBD and optionally THC at CBD to THC weight/weight ratio greater than 1, greater than 2, greater than 3, greater than 4 or greater than 5. According to an embodiment said therapeutic effect treats muscle pain, myalgia, spasticity, muscle tension, cramps and/or spasms and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats muscle pain, myalgia, spasticity, muscle tension, cramps and/or spasms and said primary terpene is selected from the group consisting of myrcene, pinene, nerolidol, linalool, humulene, caryophyllene, limonene, bisabolol, sabinene, citral, eucalyptol, terpineol, geraniol and combinations thereof. According to an embodiment, the product comprises at least 2 of these terpenes, at least 3, at least 4, or at least 5 of the terpenes. According to an embodiment, the primary terpene is selected from the group consisting of myrcene, pinene, limonene and combinations thereof. According to an embodiment, the primary terpene is selected from the group consisting of myrcene, pinene, limonene, nerolidol, linalool, caryophyllene, sabinene and combinations thereof. According to an embodiment, the primary terpene is selected from the group consisting of myrcene, pinene, nerolidol, linalool, humulene and combinations thereof. According to various embodiments said primary terpene comprises myrcene, pinene, nerolidol, linalool, humulene, caryophyllene, limonene, bisabolol, sabinene, citral, eucalyptol, geraniol and/or terpineol. According to an embodiment said therapeutic effect treats cramps and/or spasms and said primary terpene is selected from the group consisting of myrcene, pinene, nerolidol, sabinene, eucalyptol and combinations thereof. According to an embodiment said primary terpene is selected from the group consisting of myrcene, linalool, eucalyptol and combinations thereof According to an embodiment said therapeutic effect treats fatigue, weakness, decreased mental energy, decreased physical energy, dizziness and/or deficits in balance and said product comprises at least one of CBD, THC, CBC, CBG, CBN, CBL, THCV and CBDV. According to an embodiment said therapeutic effect treats fatigue, weakness, decreased mental energy, decreased physical energy, dizziness and/or deficits in balance and said product comprises CBD and optionally THC at CBD to THC weight/weight ratio greater than 1, greater than 2, greater than 3, greater than 4 or greater than 5. According to an embodiment said therapeutic effect treats fatigue, weakness, decreased mental energy, decreased physical energy, dizziness and/or deficits in balance and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats fatigue, weakness, decreased mental energy, decreased physical energy, dizziness and/or deficits in balance and said the primary terpene is selected from the group consisting of pinene, limonene, terpinene, eucalyptol, myrcene, terpineol, linalool, caryophyllene, borneol and combinations thereof. According to an embodiment, the product comprises at least 2 of these terpenes, at least 3, at least 4, or at least 5 of the terpenes. According to an embodiment, the primary terpene is selected from the group consisting of pinene, terpinene, eucalyptol and combinations thereof. According to an embodiment, the primary terpene is selected from the group consisting of limonene, myrcene, borneol and combinations thereof. According to various embodiments said primary terpene comprises terpinene, myrcene, borneol and/or caryophyllene.

According to an embodiment said therapeutic effect treats itchy skin, pruritus and/or chronic pruritus, wrinkles, stretch marks and/or skin burns and said product comprises at least one of CBD, THC, CBC, CBG, CBN, CBL, THCV and CBDV. According to an embodiment said therapeutic effect treats itchy skin, pruritus and/or chronic pruritus, wrinkles, stretch marks and/or skin burns and said product comprises CBD and optionally THC at CBD to THC weight/weight ratio greater than 1, greater than 2, greater than 3, greater than 4 or greater than 5. According to an embodiment said therapeutic effect treats itchy skin, pruritus and/or chronic pruritus, wrinkles, stretch marks and/or skin burns and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats itchy skin, pruritus and/or chronic pruritus, wrinkles, stretch marks and/or skin burns and said the primary terpene is selected from the group consisting of linalool limonene, nerolidol, pinene terpineol, myrcene, geraniol, nerol, citronellol, farnesol, carotol, sabinene and combinations thereof. According to an embodiment, the product comprises at least 2 of these terpenes, at least 3, at least 4, or at least 5 of the terpenes. According to an embodiment, the primary terpene is selected from the group consisting of linalool, terpineol, geraniol and combinations thereof. According to an embodiment said therapeutic effect treats skin burns and said the primary terpene is linalool and/or sabinene. According to an embodiment said therapeutic effect treats wrinkles, stretch marks and said the primary terpene is selected from the group consisting of geraniol, linalool, citronellol and combinations thereof. According to various embodiments said primary terpene comprises limonene, nerolidol, pinene myrcene, nerol, citronellol, farnesol, linalool, terpineol, geraniol and/or carotol. According to an embodiment, said therapeutic effect treats itchy skin, pruritus and/or chronic pruritus, wrinkles, stretch marks and/or skin burns and the product comprises a compound selected from the group consisting of linalyl acetate, citronellyl formate, eugenol, benzy acetate, benzyl alcohol, and combinations thereof.

According to an embodiment said therapeutic effect treats headache and/or migraine and said product comprises at least one of CBD, THC, CBC, CBG, CBN, CBL, THCV and CBDV. According to an embodiment said therapeutic effect treats headache and/or migraine and said product comprises CBD and optionally THC at CBD to THC weight/weight ratio greater than 1, greater than 2, greater than 3, greater than 4 or greater than 5. According to an embodiment said therapeutic effect treats headache and/or migraine and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats headache and/or migraine and said the primary terpene is selected from the group consisting of myrcene, linalool, caryophyllene, eucalyptol, limonene, nerolidol, fenchol, humulene, guaiol, borneol, pinene, bisabolol, terpinene, terpineol and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, limonene, nerolidol, fenchol and combinations thereof. According to various embodiments said primary terpene comprises of myrcene, linalool, caryophyllene, eucalyptol, limonene, nerolidol, fenchol, humulene, guaiol, borneol, pinene, terpinene, terpineol and/or bisabolol. According to an embodiment, the product includes linalool, bisabolol and/or humulene wherein linalool, bisabolol and/or humulene forms less than 5% by weight of the total terpene content.

According to an embodiment said therapeutic effect treats weight gain and/or reduces appetite and said product comprises at least one of CBD, THC, CBC, CBG, CBN, CBL, THCV and CBDV. According to an embodiment said therapeutic effect treats weight gain and/or reduces appetite and said product comprises CBD and optionally THC at CBD to THC weight/weight ratio greater than 1, greater than 2, greater than 3, greater than 4 or greater than 5. According to an embodiment said therapeutic effect treats weight gain and/or reduces appetite and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats weight gain and/or reduces appetite and said the primary terpene is selected from the group consisting of eucalyptol, caryophyllene, limonene, humulene, phytol and combinations thereof. According to an embodiment, the product comprises at least 2 of these terpenes, at least 3, at least 4, or at least 5 of the terpenes. According to an embodiment, the primary terpene is selected from the group consisting of eucalyptol, limonene, humulene and combinations thereof. According to various embodiments said primary terpene comprises caryophyllene, eucalyptol, limonene, humulene and/or phytol.

According to an embodiment said therapeutic effect treats digestive problems, intestinal disorders, gastrointestinal pain, abdominal pain (colic), pelvic pain, constipation and/or diarrhea and said product comprises at least one of CBD, THC, CBC, CBG, CBN, CBL, THCV and CBDV. According to an embodiment said therapeutic effect treats digestive problem, intestinal disorder, gastrointestinal pain, abdominal pain (colic), pelvic pain, constipation and/or diarrhea and said product comprises CBD and optionally THC at CBD to THC weight/weight ratio greater than 1, greater than 2, greater than 3, greater than 4 or greater than 5. According to an embodiment said therapeutic effect treats digestive problem, intestinal disorder, gastrointestinal pain, abdominal pain (colic), pelvic pain, constipation and/or diarrhea and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats digestive problem, intestinal disorder, gastrointestinal pain, abdominal pain (colic), pelvic pain, constipation and/or diarrhea and said the primary terpene is selected from the group consisting of limonene, cymene, ocimene, terpinene, caryophyllene, citronellol, sabinene, linalool, pinene, myrcene, germacrene, geraniol, nerolidol, menthol, humulene, fenchol, borneol and combinations thereof. According to an embodiment, the product comprises at least 2 of these terpenes, at least 3, at least 4, or at least 5 of the terpenes. According to an embodiment, the primary terpene is selected from the group consisting of limonene, sabinene, caryophyllene and combinations thereof. According to an embodiment, the primary terpene is selected from the group consisting of limonene, sabinene, caryophyllene, citronellol, linalool, myrcene, nerolidol and combinations thereof According to various embodiments said primary terpene comprises limonene, cymene, ocimene, terpinene, caryophyllene, citronellol, sabinene, linalool, pinene, myrcene, germacrene, geraniol, nerolidol, menthol, humulene, fenchol and/or borneol. According to an embodiment, said therapeutic effect treats digestive problem, intestinal disorder, gastrointestinal pain, abdominal pain (colic), pelvic pain, constipation and/or diarrhea and the product further comprises piperine. According to an embodiment, the product includes pinene, bisabolol and/or limonene, and pinene, bisabolol and/or limonene forms less than 5% by weight of the total terpene content.

According to an embodiment said therapeutic effect treats lack of appetite, nausea, vomiting and/or anorexia and said product comprises at least one of CBD, THC, CBC, CBG, CBN, CBL, THCV and CBDV. According to an embodiment said therapeutic effect treats lack of appetite, nausea, vomiting and/or anorexia and said product comprises CBD and optionally THC at CBD to THC weight/weight ratio greater than 1, greater than 2, greater than 3, greater than 4 or greater than 5. According to an embodiment said therapeutic effect treats lack of appetite, nausea, vomiting and/or anorexia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats lack of appetite, nausea, vomiting and/or anorexia and said the primary terpene is selected from the group consisting of linalool, citronellol, geraniol, menthol, humulene, bisabolol, borneol, fenchol, linalool, limonene, terpineol, pinene, caryophyllene, myrcene, cymene, terpinene and combinations thereof. According to an embodiment, the product comprises at least 2 of these terpenes, at least 3, at least 4, or at least 5 of the terpenes. According to an embodiment, the primary terpene is selected from the group consisting of citronellol, linalool caryophyllene and combinations thereof. According to an embodiment, the primary terpene is selected from the group consisting of citronellol, linalool caryophyllene, limonene, myrcene, nerolidol and combinations thereof According to various embodiments said primary terpene comprises linalool, citronellol, geraniol, menthol, humulene, bisabolol, borneol, fenchol, linalool, limonene, terpineol, pinene, caryophyllene, myrcene, cymene and/or terpinene. According to an embodiment, the product includes pinene. borneol, fenchol, terpinene and/or terpineol, and pinene, bisabolol and/or limonene forms less than 5% by weight of the total terpene content.

According to an embodiment said therapeutic effect treats joint pain, joint stiffness, arthralgia, arthritis and/or osteoarthritis and said product comprises at least one of CBD, THC, CBC, CBG, CBN, CBL, THCV and CBDV. According to an embodiment said therapeutic effect treats joint pain, joint stiffness, arthralgia, arthritis and/or osteoarthritis and said product comprises CBD and optionally THC at CBD to THC weight/weight ratio greater than 1, greater than 2, greater than 3, greater than 4 or greater than 5. According to an embodiment said therapeutic effect treats joint pain, joint stiffness, arthralgia, arthritis and/or osteoarthritis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats a joint pain, joint stiffness, arthralgia, arthritis and/or osteoarthritis and said the primary terpene is selected from the group consisting of myrcene, linalool, caryophyllene, eucalyptol, pinene, nerolidol, sabinene, limonene, terpinene, menth-2-en-1-ol, terpineol, geraniol, guaiol, humulene, bisabolol, borneol, fenchol and combinations thereof. According to an embodiment, the product comprises at least 2 of these terpenes, at least 3, at least 4, or at least 5 of the terpenes. According to an embodiment, the primary terpene is selected from the group consisting of myrcene, pinene, sabinene and combinations thereof. According to an embodiment, the primary terpene is selected from the group consisting of myrcene, pinene, sabinene linalool, caryophyllene, limonene and combinations thereof. According to various embodiments said primary terpene comprises myrcene, linalool, caryophyllene, eucalyptol, pinene, nerolidol, sabinene, limonene, terpinene, menth-2-en-1-ol, geraniol, guaiol, humulene, bisabolol, borneol, fenchol 1 and/or terpineol. According to an embodiment, said therapeutic effect treats joint pain, joint stiffness, arthralgia, arthritis and/or osteoarthritis and the product comprises a compound selected from the group consisting of linalyl acetate, geranyl acetate, eugenol, methylis-oeugenol, menthol, eugenyl acetate, piperine and combinations thereof. According to an embodiment, the product optionally includes humulene, pinene, bisabolol, borneol, fenchol, guaiol, linalool, ocimene, terpineol, terpinene and/or caryophyllene, and humulene, pinene, bisabolol, borneol, fenchol, guaiol, linalool, ocimene, terpineol, terpinene and/or caryophyllene forms less than 5% by weight of the total terpene content.

According to an embodiment said therapeutic effect treats hot flashes, night sweat, palpitation, irritability and/or restlessness and said product comprises at least one of CBD, THC, CBC, CBG, CBN, CBL, THCV and CBDV. According to an embodiment said therapeutic effect treats hot flashes, night sweat, palpitation, irritability and/or restlessness and said product comprises CBD and optionally THC at CBD to THC weight/weight ratio greater than 1, greater than 2, greater than 3, greater than 4 or greater than 5. According to an embodiment said therapeutic effect treats hot flashes, night sweat, palpitation, irritability and/or restlessness and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats hot flashes, night sweat, palpitation, irritability and/or restlessness and said the primary terpene is selected from the group consisting of caryophyllene, myrcene, humulene, pinene, linalool, limonene, nerolidol, terpinene, terpineol, geraniol, carene, citronellol, eucalyptol, sabinene, myrtenol, bisabolol, borneol, fenchol and combinations thereof. According to an embodiment, the product comprises at least 2 of these terpenes, at least 3, at least 4, or at least 5 of the terpenes. According to an embodiment, the primary terpene is selected from the group consisting of linalool, limonene, eucalyptol and combinations thereof. According to an embodiment, the primary terpene is selected from the group consisting of linalool, limonene, terpineol, geraniol, citronellol, eucalyptol and combinations thereof. According to various embodiments said primary terpene comprises caryophyllene, myrcene, humulene, pinene, linalool, limonene, nerolidol, terpinene, terpineol, geraniol, carene, citronellol, eucalyptol, sabinene, myrtenol, bisabolol, borneol and/or fenchol. According to an embodiment, said therapeutic effect treats hot flashes, night sweat, palpitation, irritability and/or restlessness and the product further comprises a compound selected from the group consisting of linalyl acetate, geranyl acetate, citronellyl formate and combinations thereof. According to an embodiment, the product optionally includes pinene, bisabolol and/or terpineol, and pinene, bisabolol and/or terpineol forms less than 5% by weight of the total terpene content.

According to an embodiment said therapeutic effect treats inflammation, oxidative stress and/or paresthesia and said product comprises at least one of CBD, THC, CBC, CBG, CBN, CBL, THCV and CBDV. According to an embodiment said therapeutic effect treats inflammation, oxidative stress and/or paresthesia and said product comprises CBD and optionally THC at CBD to THC weight/weight ratio greater than 1, greater than 2, greater than 3, greater than 4 or greater than 5. According to an embodiment said therapeutic effect treats inflammation, oxidative stress and/or paresthesia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats inflammation, oxidative stress and/or paresthesia and said the primary terpene is selected from the group consisting of caryophyllene, pinene, myrcene, limonene, humulene, citronellol, eucalyptol, linalool, beta amyrin, cycloartenol, terpinene, terpineol, geraniol, carvacrol, thymol, cardinol, terpinene, menth-2-en-1-ol, carotol, humulene, nerolidol and combinations thereof. According to an embodiment, the product comprises at least 2 of these terpenes, at least 3, at least 4, or at least 5 of the terpenes. According to an embodiment, the primary terpene is selected from the group consisting of myrcene, limonene, thymol and combinations thereof. According to an embodiment, the primary terpene is selected from the group consisting of caryophyllene, pinene, linalool, humulene, myrcene, limonene, thymol and combinations thereof. According to various embodiments said primary terpene comprises caryophyllene, pinene, myrcene, limonene, humulene, citronellol, eucalyptol, linalool, beta amyrin, cycloartenol, terpinene, terpineol, geraniol, carvacrol, thymol, cardinol, terpinene, menth-2-en-1-ol, carotol, humulene, n and/or nerolidol. According to an embodiment, said therapeutic effect treats inflammation, oxidative stress and/or paresthesia and the product further comprises a compound selected from the group consisting of linalyl acetate, geranyl acetate, eugenol, eugenyl acetate, piperine and combinations thereof. According to an embodiment, the product optionally includes fenchol and/or borneol, and fenchol and/or borneol forms less than 5% by weight of the total terpene content.

According to an embodiment said therapeutic effect treats cardiovascular disease, palpitation and tachycardia and said product comprises at least one of CBD, THC, CBC, CBG, CBN, CBL, THCV and CBDV. According to an embodiment said therapeutic effect treats cardiovascular disease, palpitation and tachycardia and said product comprises CBD and optionally THC at CBD to THC weight/weight ratio greater than 1, greater than 2, greater than 3, greater than 4 or greater than 5. According to an embodiment said therapeutic effect treats cardiovascular disease, palpitation and tachycardia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats cardiovascular disease, palpitation and tachycardia and said the primary terpene is selected from the group consisting of linalool, camphene, limonene, pinene, borneol and combinations thereof. According to an embodiment, the product comprises at least 2 of these terpenes, at least 3, at least 4, or all 5 of the terpenes. According to an embodiment, the primary terpene is selected from the group consisting of camphene, limonene, pinene and combinations thereof. According to various embodiments said primary terpene comprises linalool, camphene, limonene, pinene and/or borneol.

According to an embodiment, the enhanced therapeutic effect comprises reducing side effects associated with *cannabis* consumption. According to an embodiment, the primary terpene comprises geraniol, and the side effect comprises hypoglycemia and/or reduction of glucose level. According to an embodiment, the primary terpene is selected from the group consisting of pinene, terpinene, linalool, eucalyptol, myrcene, terpineol, limonene, caryophyllene, borneol and combinations thereof, and the side effect comprises fatigue, weakness, dizziness and/or deficits in balance. According to an embodiment, the primary terpene is selected from the group consisting of camphene, limonene, pinene, borneol and combinations thereof, and the side effect comprises palpitation and/or tachycardia. According to an embodiment, the primary terpene is selected from the group consisting of linalool, citronellol, geraniol, menthol, humulene, bisabolol, borneol, fenchol, linalool, limonene, terpineol, pinene, caryophyllene, myrcene, cymene, terpinene and combinations thereof, and the side effect comprises digestive disorders including vomiting and/or diarrhea. According to an embodiment, the primary terpene is selected from the group consisting myrcene, linalool, caryophyllene, eucalyptol, limonene, nerolidol, fenchol, humulene, guaiol, borneol, bisabolol and combinations thereof, and the side effect comprises headache. According to an embodiment, the primary terpene is selected from the group consisting of pinene, eucalyptol, limonene and combinations thereof, and the side effect comprises coughing. According to an embodiment, the primary terpene is selected from the group consisting of linalool, terpineol, geraniol, thujone, camphor, viridiflorol, borneol, champhene, pinene, eucalyptol, caryophyllene, germacrene, pinene, carene, cirtonellol, nerol, farnesol, limonene, myrcene, terpinene, menth-2-en-1-ol, carotol, sabinene, neral, geranial and combinations thereof, and the side effect comprises impaired fertility. According to an embodiment, the primary terpene is selected from the group consisting of eucalyptol, caryophyllene, limonene, humulene, phytol and combinations thereof, and the side effect comprises increased appetite. According to an embodiment, the primary terpene is selected from the group consisting of pinene, pulegone, eucalyptol, terpineol, cymene, ocimene, limonene, linalool, caryophyllene, humulene, carene and combinations thereof, and the side effect comprises impaired memory, impaired concentration and/or impaired perception. According to an embodiment, the primary terpene is selected from the group consisting of limonene, linalool, caryophyllene, eucalyptol, pinene, myrcene, terpinene, nerolidol, terpineol, geraniol, menthol, citronellol, neral, geraniol, menthol, borneol, phellandrene, bisabolol, fenchol, humulene and combinations thereof, and the side effect comprises anxiety and/or psychotic-like effects.

According to an embodiment, the product comprises an additive selected from the group consisting of antioxidants, emulsifiers and texturizers vegetable oils, plant extracts, honey, pharmaceutical excipients, sucrose, glucose and fructose, pharmaceutical excipients and combinations thereof. According to an embodiment, the product comprises a surfactant selected from the group consisting of phospholipids, glycerides, glycolipids and combinations thereof. According to an embodiment, the product further comprises a food-approved texturizer. According to an embodiment, the product further comprises at least 10 ppm ethanol. According to an embodiment, the product further comprises at least one of vitamin C, vitamin E, polyunsaturated fatty acids, beeswax and coconut oil. According to an embodiment, the product further comprises a sweetener. According to an embodiment, the product further comprises omega 3 fatty acid. According to an embodiment, the product further comprises omega 6 fatty acid. According to an embodiment, the product further comprises curcumin.

According to an embodiment, the terpene-enriched cannabinoid product of improved therapeutic effect is a human medication. According to an embodiment, the terpene-enriched cannabinoid product of improved therapeutic effect is a veterinary medication.

According to an embodiment, the shelf life of the product is at least 6 months or at least a year. According to an embodiment, primary terpene degradation in the product is less than 20% per year.

According to an embodiment, further provided is a product selected from the group consisting of tablets, gel capsules, medical patches, topicals, creams, varnishes, sublingual oils, sprays, edibles, beverages, suppositories, tampons, rectal candle, cigarette, vaporizer liquid nasal preparation, preparations containing micro and nano-emulsions, preparations containing micro and nano-particles and combinations thereof, containing the product.

According to an embodiment, further provided is a commercial product comprising two products according to the present invention, which two products differ in the content of the primary terpene. According to an embodiment, further provided is a commercial product comprising two products according to the present invention, which two products comprise different primary terpenes.

According to an embodiment, further provided is a method for producing the product comprising providing at least one cannabinoid and blending it with a primary terpene.

According to an embodiment, the method includes extracting *cannabis* plant material to form an extract. According to an embodiment the extracting comprises steam distillation. According to an embodiment, the method further comprises removing terpenes from the extract prior to the blending. According to an embodiment, the extracting comprises contacting with an extractant to form an extract, which extract comprises at least one cannabinoid and the extractant; and optionally removing at least a fraction of the extractant from the extract. According to an embodiment, the extractant comprises at least one of ethanol, a liquefied gas, such as butane, butene or dimethyl-ether, liquefied $CO_2$, near-critical $CO_2$ supercritical $CO_2$ and combinations thereof. According to an embodiment, extracting comprises contacting the *cannabis* plant material with an extractant to form an extract, and the extractant comprises at least one terpene. According to an embodiment, the extractant comprises the primary terpene.

According to an embodiment, the method further comprises at least partially decarboxylating the cannabinoid. According to an embodiment the decarboxylating is conducted at a temperature greater than 100° C. According to an embodiment the decarboxylating is conducted prior to extracting. According to an embodiment the decarboxylating is conducted on the extract prior to the blending with the primary terpene. According to an embodiment, a fraction of the extract is decarboxylated, and the decarboxylated fraction is blended with another fraction, which was not decarboxylated.

According to an embodiment, the method further comprises extracting a plant material, whereby the primary terpene is produced. According to an embodiment, the plant material is selected from the group including *cannabis*, lemons, oranges, hops, lavender, pine needles, *Echinacea*, tea, clover, *Capsicum, eucalyptus*, geranium and mint.

According to an embodiment, the method comprises synthesizing at least one cannabinoid and blending the synthesized cannabinoid with the primary terpene.

According to an embodiment, the method further comprises blending *cannabis* plant material with the primary terpene. According to an embodiment, the *cannabis* plant material comprises a *cannabis* bud. According to an embodiment, the blending *cannabis* plant material with the primary terpene comprises spraying the *cannabis* plant material with the primary terpene, optionally in a solvent. According to an embodiment, the blending *cannabis* plant material with the primary terpene comprises combining the *cannabis* plant material with a substrate comprising the primary terpene. According to an embodiment, the substrate is a plant material sprayed with the primary terpene. According to an embodiment, the substrate is a cigarette paper sprayed with the primary terpene.

According to an embodiment, further provided is a method for producing the product comprising extracting *cannabis* plant material to form an extract, wherein the extracting forms at least two extract fractions, a cannabinoid-enriched extract and a terpene-enriched extract. As used herein, the term "cannabinoid-enriched extract" refers to an extract wherein cannabinoid to terpenes weight/weight ratio is greater than that in the plant material. As used herein, the term "terpene-enriched extract" refers to an extract wherein cannabinoid to terpenes weight/weight ratio is smaller than that in the plant material. According to an embodiment, the method comprises dividing the cannabinoid-enriched extract into at least two fractions and mixing at least one fraction with at least part of the terpene-enriched extract to form a terpene-enriched product, wherein terpenes to cannabinoid weight/weight ratio is greater than that ratio in the *cannabis* plant material. According to an embodiment the ratio is 1.5 times greater than that in the *cannabis* plant material, 2 times greater, 2.5 times greater, 3 times greater, 4 times greater, 5 times greater, 6 times greater, 7 times greater, 8 times greater, or 10 times greater. According to an embodiment, the terpene-enriched product is further mixed with at least one terpene.

According to an embodiment, further provided is a treatment method comprising administering to a subject in need a therapeutically effective amount of a product comprising (i) at least one cannabinoid in a specific amount, (ii) a primary terpene in a specific amount, (iii) at least 5% by weight of a non-cannabinoid, non-terpene, carrier; (iv) optionally at least three secondary terpenes, optionally combined with at least one herbal extract, having an enhanced therapeutic effect compared with administrating a product comprising the same cannabinoids amounts and one half the amount of said primary terpene. According to an embodiment, the non-cannabinoid, non-terpene carrier comprises cellulose and the terpenes to cannabinoids weight/weight ratio in said product is about 0.1 to about 1.0. According to an embodiment, the non-cannabinoid, non-terpene carrier comprises less than 5% by weight cellulose and the terpenes to cannabinoids weight/weight ratio in said product is about 0.05 to about 1.0.

According to an embodiment, the administered product has an enhanced therapeutic effect in treating and/or healing and/or relieving and/or decreasing, preventing and/or reducing the risk associated with, and/or improving the quality of life associated with conditions and/or symptoms associated with at least one of arthritis, osteoarthritis, arthralgia, joint pain, joint stiffness, diabetes, lack of appetite, anorexia, vomiting, nausea, an inflammatory bowel disease including Crohn's disease and ulcerative colitis, dementia, memory loss, osteoporosis, fatigue, weakness, decreased mental energy, decreased physical energy, dizziness, deficits in balance, itchy skin, pruritus and/or chronic pruritus, wrinkles, stretch marks, skin burn, headache, migraine, weight gain, digestive problem, intestinal disorder, gastrointestinal pain, abdominal pain, pelvic pain, constipation, diarrhea, hot flashes, sweating, difficulty in concentration, weakened immune system, cardiovascular disease, palpitation and tachycardia, psoriasis, dermatophytes, *Candida*, leishmaniasis, Methycillin-resistant *Staphylococcus aureus* (MRSA), malaria, allergy, fibromyalgia, nociceptive pain, neuropathic pain, pain, arm or leg pain, acne, insomnia and/or sleep disorders, muscle pain, myalgia, spasticity, muscle tension, cramps, spasms, anxiety, irritability, nervousness, restless, stress, depression, mood problem, affect disorders, anger, autism and/or autism spectrum disorder, neurodegenerative diseases, Alzheimer disease, Parkinson disease, Huntington's disease, Dystonia, Amyotrophic Lateral Sclerosis (ALS), multiple sclerosis, Tourette syndrome, Myasthenia Gravis, epilepsy, cancer, inflammatory airway diseases including asthma and/or chronic obstructive pulmonary disease (COPD), addiction, stroke, traumatic brain injury, motor spasm and/or tic, vocal tic, obsessive compulsive disorder (OCD), attention deficit hyperactivity disorder (ADHD), attention deficit disorder (ADD), cerebral palsy (CP), inflammation, oxidative stress, paresthesia, glaucoma and combinations thereof. According to an embodiment, the conditions and/or symptoms are associated with aging.

According to an embodiment, the administered product has an enhanced therapeutic effect in treating conditions and/or symptoms associated with aging. According to a related embodiment, the primary terpene is selected from the group consisting of caryophyllene, linalool, pinene, eucalyptol, sabinene, terpineol and combinations thereof. According to an embodiment, the composition comprises at least 2 of the terpenes, at least 3, at least 4 or at least 5 of the terpenes. According to an embodiment, the primary terpene is selected from the group consisting of caryophyllene, linalool, pinene, terpineol and combinations thereof. According to an embodiment, the primary terpene is selected from the group consisting of caryophyllene, linalool, sabinene and combinations thereof.

According to an embodiment, the enhanced therapeutic effect applies to a child. As used herein the term "therapeutic effect applies to a child" refers to therapeutic effect observed when the treated patient is a child.

According to an embodiment, the administered product has an enhanced therapeutic effect in treating a child. According to a related embodiment, the primary terpene is selected from the group consisting of caryophyllene, limonene, pinene, terpineol and combinations thereof. According to an embodiment, the composition comprises at least 2 of the terpenes, at least 3, or all 4 of the terpenes. According to an embodiment, the primary terpene is selected from the group consisting of caryophyllene, limonene and combination thereof.

According to an embodiment, the conditions and/or symptoms are observed in a child.

According to an embodiment, the product is selected from the group consisting of cigarettes, vaporizer plant material, vaporizer liquid, extract, tablets, gel capsules, suppositories, tampons, rectal candle, cigarette, vaporizer liquid, nasal preparation, preparations containing micro and nano-emulsions, preparations containing micro and nano-particles and combinations thereof. According to an embodiment, the daily dose of the product comprises about 1 milligram cannabinoid to about 300 milligram, about 2 milligram cannabinoid to about 200 milligram or about 3 milligram cannabinoid to about 100 milligram. According to another embodiment, the daily dose of the product comprises about 0.5 milligram cannabinoid per kilogram body weight to about 30 milligram cannabinoid per kilogram body weight.

According to an embodiment, the administered product comprises at least two cannabinoids, at least three, at least four or at least five. According to an embodiment, the content of each cannabinoid in the product is at least 10 parts per million (ppm). According to an embodiment, the cannabinoids are selected from the group consisting THC, CBD, CBG, CBC, CBN, CBL, THCV, CBDV and their non-decarboxylated form thereof.

According to an embodiment, the administered product comprises at least 2% by weight carrier, at least 3%, at least 5%, at least 7%, at least 10%, at least 12%, at least 15%, at least 20%, at least 25%, at least 30%, at least 35% or at least 40% by weight. Any compound other than cannabinoids and terpenes is a suitable carrier. According to an embodiment, the carrier is selected from the group consisting of vegetable oils, e.g. coconut oil, olive oil or sesame oil, pharmaceutical excipients, honey, bees wax, cellulose and combinations thereof.

According to an embodiment, the administered product comprises a primary terpene and optionally at least one secondary terpenes, at least two, at least three secondary terpenes, at least four, or at least five secondary terpenes. As used herein, the term "primary terpene" refers to a terpene that forms at least 20% by weight of the total amount of terpenes in the product, at least 25%, at least 30%, at least 35%, at least 40%, at least 50%, at least 60%, at least 70% or at least 80%. As used herein, the term "primary terpene" refers to a terpene having the greatest amount in the composition. As used herein, the term "primary terpene" refers to a terpene that forms the highest terpene concentration in the composition. According to an embodiment, the product comprises multiple (e.g. two, three, or four) According to an embodiment, the primary terpene forms at least 20% by weight of the total terpene content, at least 30%, at least 40%, at least 50%, at least 60%, at least 70% or at least 80%, at least 90% by weight of the total terpene content. According to an embodiment, the product comprises multiple (e.g. two or three) terpenes, each one of which forms at least 20% by weight of the total amount of terpenes in the product and each one of these terpenes is considered a primary terpene. According to an embodiment, the product comprises multiple (e.g. two, three, or four) terpenes, each one of which forms at least 15% by weight of the total amount of terpenes in the product, at least 18%, at least 22%, at least 25%, at least 30%, at least 35%, or at least 40%, and each one of these terpenes is considered a primary terpene. As used here, in the term "secondary terpene" refers to a terpene that forms at least 10 parts per million (ppm) of the product. According to an embodiment, the content of the primary terpene in the product is at least 1.3 times greater than that of any secondary terpene, at least 1.5, at least 2, at least 2.2, at least 2.5, at least 3, at least 3.5, at least 4, at least 6, at least 8, at least 10, at least 15, at least 20, at least 25, or at least 30 times greater.

According to an embodiment, the non-cannabinoid, non-terpene carrier comprises cellulose and the terpenes to cannabinoids weight/weight ratio in the product is about 0.1 to about 1.0. According to an embodiment said non-cannabinoid, non-terpene, carrier comprises at least 5% by weight cellulose, at least 6%, at least 8%, at least 10%, at least 15%, or at least 20%. According to an embodiment, the ratio is greater than 0.1, greater than 0.12, greater than 0.13, greater than 0.15, greater than 0.2, greater than 0.25, greater than 0.3, greater than 0.35, greater than 0.4, greater than 0.45, greater than 0.5, greater than 0.55, greater than 0.6, greater than 0.65, greater than 0.7, greater than 0.75, greater than 0.8, greater than 0.85, greater than 0.9, greater than 0.95, greater than 1, greater than 1.2, greater than 1.5, greater than 2.0, greater than 3 or greater than 5. According to an embodiment, the ratio is less than 1, less than 0.9, less than 0.8, less than 0.7, less than 0.6, less than 0.5, less than 0.4, less than 0.3, less than 0.2 or less than 0.15. According to an embodiment, the product comprising more than 5% cellulose is selected from the group consisting of *cannabis* plant material, e.g. *cannabis* buds (also referred to as *cannabis* inflorescence) or *cannabis* trim, ground forms thereof, plant material preparation for vaporizers and *cannabis* cigarette. According to an embodiment, the product comprises a dried *cannabis* plant material.

According to an embodiment, the non-cannabinoid, non-terpene carrier comprises less than 5% by weight cellulose and the terpenes to cannabinoids weight/weight ratio in the product is about 0.05 to about 1.0. According to an embodiment said non-cannabinoid, non-terpene, carrier comprises less than 5% by weight cellulose, less than 4%, less than 3%, less than 2%, or less than 1% cellulose. According to an embodiment, the ratio is greater than 0.05, greater than 0.06, greater than 0.07, greater than 0.08, greater than 0.09, greater than 0.1, greater than 0.12, greater than 0.15, greater than 0.2, greater than 0.25, greater than 0.3, greater than 0.35, greater than 0.4, greater than 0.45, greater than 0.5, greater than 0.55, greater than 0.6, greater than 0.65, greater than 0.7, greater than 0.75, greater than 0.8, greater than 0.85, greater than 0.9, greater than 0.95, greater than 1, greater than 1.2, greater than 1.5, greater than 2.0, greater than 3 or greater than 5. According to an embodiment, the ratio is less than 1, less than 0.9, less than 0.8, less than 0.7, less than 0.6, less than 0.5, less than 0.4, less than 0.3, less than 0.2, less than 0.15, less than 0.1, less than 0.09, less than 0.08, less than 0.07, less than 0.06, or less than 0.05. According to an embodiment, the product comprising less than 5% cellulose is selected from the group consisting of *cannabis* trichomes, *cannabis* extracts and products thereof, such as tablets, gel capsules, medical patches, topicals, creams, varnishes, sublingual oils, sprays, edibles, beverages, suppositories, tampons, rectal candles, cigarettes, vaporizer liquids, nasal preparation, preparations containing micro and nano-emulsions, preparations containing micro and nano-particles and combinations thereof. According to an embodiment, said product comprises a liquid.

According to an embodiment, the primary terpene, the secondary terpenes or both are selected from the group consisting of pinene, limonene, linalool, caryophyllene, caryophyllene oxide, myrcene, humulene, borneol, eucalyptol, terpineol, nerolidol, phytol, geraniol, bisabolol, camphene, amyrin, thujone, citronellol, pulegone, cycloartenol, cymene, sabinene, carene, terpinene, fenchol, isopulegol, guaiol, phellandrene, eudesmol, ocimene, cardinol, elemene, friedelin, carvacrol, eugenol, camphor, menthol, iso-menthone, neral, gerial, viridiflorol, germacrene, thymol, Menth-2-en-1-ol, farensol, carotol, myrtenol, isomers thereof and combinations thereof. According to an embodiment, the primary terpene, the secondary terpenes or both, are selected from the group consisting of pinene, limonene, linalool, caryophyllene, myrcene, terpineol, eucalyptol, geraniol and combinations thereof. According to an embodiment, the primary terpene the secondary terpenes or both, are selected from the group consisting of pinene, limonene, linalool, caryophyllene, myrcene, terpineol, eucalyptol and combinations thereof. According to an embodiment, the primary terpene is selected from the group consisting of pinene, limonene, linalool, caryophyllene, myrcene, terpineol, eucalyptol, geraniol, humulene and combinations thereof. According to an embodiment, at least one of the terpenes is a-cyclic. According to an embodiment, at least one of the terpenes is cyclic. According to an embodiment, at least one of the terpenes is not found in cannabis buds or is present there at less than 0.2%, less than 0.1%, less than 0.05% or less than 0.02%. Such terpene is referred to as "non-cannabis terpene". According to an embodiment, the terpene-enriched cannabinoid product comprises the non-cannabis terpene at a concentration of at least 0.2%, at least 0.5%, least 0.8%, at least 1%, least 1.5%, at least 2%, at least 3%, least 4%, at least 5%, at least 8% or at least 12%.

According to an embodiment, terpenes form at least 0.5% by weight of the product, at least 0.6%, at least 0.8%, at least 1%, at least 2%, at least 3%, at least 5%, at least 10%, at least 20%, at least 30%, at least 40%, at least 50%, at least 60% or at least 70%.

According to an embodiment, the product comprises a composition, which is liquid at 30° C. According to an embodiment, the product comprises a composition, which is a suspension at 30° C. According to an embodiment, the product comprises a composition, which is essentially clear of haze or suspended solids at 30° C.

According to an embodiment, the product comprises cannabis plant material. According to an embodiment, the product comprises cannabis bud. According to an embodiment, the cannabis bud forms at least 20% of the product, at least 30%, at least 40%, at least 50%, at least 60%, at least 70% or at least 80%.

According to an embodiment, the administered product is combines with at least one herbal extract, at least two, at least three, at least four, or at least five herbal extracts.

According to an embodiment, the administered product comprises less than 5% by weight glycol, less than 4%, less than 3%, less than 2%, or less than 1% by weight.

According to an embodiment, the administered product comprises less than 20% by weight water, less than 15% by weight, less than 14%, less than 13%, less than 12%, less than 11% or less than 10% by weight.

According to a related embodiment, the administered product comprises chlorophyll. According to an embodiment, the product comprises at least 0.5% by weight chlorophyll, at least 1%, at least 5%, at least 10%, at least 15%, at least 20% chlorophyll. According to an embodiment, the administered product comprises at least one flavonoid. According to an embodiment, the product comprises at least two, at least three, at least four, or at least five flavonoids. According to an embodiment, the product comprises at least one of bergamottin, apigenin, amentoflavone, quercetin and piperine. According to an embodiment, the product comprises at least two, at least three, or at least four of bergamottin, apigenin, amentoflavone, quercetin and piperine. According to an embodiment, the product comprises bergamottin. According to an embodiment, the product comprises apigenin. According to an embodiment, the product comprises amentoflavone. According to an embodiment, the product comprises quercetin. According to an embodiment, the product comprises piperine.

According to an embodiment, the administered product additionally contains an additive selected from the group consisting of antioxidants, emulsifiers and texturizers vegetable oils, plant extracts, honey, sucrose, glucose and fructose, pharmaceutical excipients and combinations thereof.

According to an embodiment the product comprises tetrahydrocannabinol (THC) and/or tetrahydrocannabinolic acid (THCa), wherein THC and/or THCa is in a total concentration of at least 1% by weight, at least 2%, at least 3%, at least 4%, at least 5%, at least 6%, at least 8%, at least 10%, at least 12%, at least 14%, at least 16%, at least 18%, or at least 20%, at least 30%, at least 40%, at least 50%, at least 60%, at least 70%, at least 80%, or at least 90% by weight.

According to an embodiment, the product comprises cannabidiol (CBD) and/or cannabidiolic acid (CBDa), wherein CBD and/or CBDa is in a total concentration of at least 1% by weight, at least 2%, at least 3%, at least 4%, at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight.

According to an embodiment, the product comprises tetrahydrocannabinol (THC) and/or tetrahydrocannabinolic acid (THCa) and cannabidiol (CBD) and/or cannabidiolic acid (CBDa), wherein, THC and/or THCa is in a total concentration of at least 2.5% by weight, and CBD and/or CBDa is in a total concentration of at least 2.5% by weight; THC and/or THCa in a total concentration of at least 3% by weight, and CBD and/or CBDa in a total concentration of at least 3% by weight; THC and/or THCa in a total concentration of at least 4% by weight, and CBD and/or CBDa in a total concentration of at least 4% by weight; THC and/or THCa in a total concentration of at least 5% by weight, and CBD and/or CBDa in a total concentration of at least 5% by weight; THC and/or THCa in a total concentration of at least 8% by weight, and CBD and/or CBDa in a total concentration of at least 8% by weight; THC and/or THCa in a total concentration of at least 10% by weight, and c CBD and/or CBDa in a total concentration of at least 10% by weight.

According to a related embodiment, said product comprises cannabigerol (CBG) and/or cannabigerol acid (CBGa) in a total concentration of at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises cannabinol (CBN) and/or cannabinol acid (CBNa) in a total concentration of at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 600%, at least 70%, at least 800%, or at least 90% by weight. According to a related embodiment, said product comprises cannabichromene (CBC) and/or cannabichromenic acid (CBCa) in a total concentration of at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises cannabicyclol (CBL) and/or cannabicyclol acid (CBLa) in a total concentration at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises tetrahydrocannabivarin (THCV), and/or tetrahydrocannabivarin acid (THCVA) in a total concentration at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight. According to a related embodiment, said product comprises cannabidivarin (CBDV) and/or cannabigerovarin acid (CBGVA) in a total concentration at least 0.1% by weight, at least 0.5%, at least 1%, at least 2%, at least 3%, at least 4%, or at least 5%, at least 6%, at least 8%, at least 10%, at least 12%, at least 14%, at least 16%, at least 18% or at least 20%, at least 30%, at least 40%, at least 50%, at least 60%, at least 70%, at least 80%, or at least 90% by weight.

According to an embodiment, the product results in an increased and/or enhanced therapeutic effect compared with that of a product comprising the same amounts of cannabinoids and optionally secondary terpenes and a smaller amount of the primary terpene, e.g. one half of that amount. According to various embodiment, the increased therapeutic effect has various forms, e.g. a shorter onset time, increased magnitude, extended duration, reduced dosages, reduced secondary adverse symptoms, reduced frequency of conditions and/or symptoms, reduced severity of conditions and/or symptoms, reduced consumption of other drugs and combinations thereof. According to an embodiment, the increased therapeutic effect comprises a shorter onset time, or differently put an earlier effect, which is important particularly in cases of sublingual and topical delivery and in cases where a rapid effect is desired, as in treating pain. According to an embodiment, the increased therapeutic effect comprises extended duration of the therapeutic effect, for example an extended time of pain relief. According to an embodiment, the increased therapeutic effect comprises increased magnitude of the therapeutic effect, enabling achieving a desired therapeutic effect on administering smaller doses of cannabinoids, saving thereby on cost. According to an embodiment, the increased therapeutic effect comprises using smaller doses of cannabinoids and still achieving at least the same beneficial result. According to an embodiment, the increased therapeutic effect comprises reduction of secondary adverse symptoms, e.g. adverse symptoms of the main illness, of ones of another illness and/or ones related to administered the product or other drugs. According to an embodiment, the increased therapeutic effect comprises reduced frequency of the conditions and/or symptoms. According to an embodiment, the increased therapeutic effect comprises reduced severity of the conditions and/or symptoms.

According to an embodiment, said enhanced therapeutic effect comprises shorter onset time of the therapeutic effect. According to an embodiment, the primary terpene, the cannabinoids and optionally secondary terpenes are present in specific amounts, and the onset time of the therapeutic effect, as measured by methods known in the art, is at least 20% shorter than that of a product comprising the same amounts of cannabinoids and secondary terpenes and one half the amount of the primary terpene, at least 30%, at least 40%, at least 50%, at least 60%, or at least 70% shorter. Shorter onset time, or differently put an earlier effect, is important particularly in cases of sublingual, edible and topical delivery and in cases where a rapid effect is desired, as in treating pain.

According to an embodiment, said enhanced therapeutic effect comprises longer onset time of the therapeutic effect. According to an embodiment, the primary terpene, the cannabinoids and optionally secondary terpenes are present in specific amounts, and the onset time of the therapeutic effect, as measured by methods known in the art, is at least 20% longer than that of a product comprising the same amounts of cannabinoids and secondary terpenes and one half the amount of the primary terpene, at least 30%, at least 40%, at least 50%, at least 60%, or at least 70% longer. According to an embodiment, products of delayed onset time are used in combination with shorter onset time to reach a sustained release effect.

According to an embodiment, said enhanced therapeutic effect comprises greater and/or increased magnitude of the therapeutic effect. According to an embodiment, the primary terpene, the cannabinoids and optionally secondary terpenes are present in specific amounts, and the magnitude of the therapeutic effect, as measured by methods known in the art, is at least 20% greater compared with that of a product comprising the same amounts of cannabinoids and secondary terpenes and one half the amount of the primary terpene, at least 30%, at least 40%, at least 500%, at least 60%, or at least 70% greater. Without wishing to be limited by any particular theory, such increased magnitude of the therapeutic effect may indicate increased bioavailability. Such increased magnitude enables achieving a desired therapeutic effect on administering smaller doses of cannabinoids, saving thereby on cost.

According to an embodiment, said enhanced therapeutic effect comprises longer and/or extended duration of the therapeutic effect. According to an embodiment, the primary terpene, the cannabinoids and optionally secondary terpenes are present in specific amounts, and the duration of the therapeutic effect, as measured by methods known in the art, is at least 20% longer compared with that of a product comprising the same amounts of cannabinoids and secondary terpenes and one half the amount of the primary terpene, at least 30%, at least 40%, at least 50%, at least 60%, at least 70%, at least 80%, at least 90% or at least 100% longer.

According to an embodiment, said enhanced therapeutic effect comprises smaller therapeutically effective amount of a product and/or reduced dosages of the product. According to an embodiment, the primary terpene, the cannabinoids and optionally secondary terpenes are present in specific amounts, and the therapeutically effective amount of the product, as measured by methods known in the art, is at least 20% smaller compared with that of a product comprising the same amounts of cannabinoids and secondary terpenes and one half the amount of the primary terpene, at least 30%, at least 40%, at least 50%, at least 60%, at least 70%, at least 80%, at least 90% or at least 100% smaller.

According to an embodiment, said enhanced therapeutic effect comprises reduced secondary adverse symptoms. According to an embodiment, the primary terpene, the cannabinoids and optionally secondary terpenes are present in specific amounts, and the secondary adverse symptoms, as measured by methods known in the art, are reduced by at least 20% compared with that of a product comprising the same amounts of cannabinoids and secondary terpenes and one half the amount of the primary terpene, by at least 30%, at least 40%, at least 50%, at least 60%, at least 70%, at least 80%, at least 90% or at least 100%.

According to an embodiment, said enhanced therapeutic effect comprises smaller and/or reduced frequency of conditions and/or symptoms. According to an embodiment, the primary terpene, the cannabinoids and optionally secondary terpenes are present in specific amounts, and the frequency of the conditions and/or symptoms, as measured by methods known in the art, is at least 20% smaller compared with that of a product comprising the same amounts of cannabinoids and secondary terpenes and one half the amount of the primary terpene, at least 30%, at least 40%, at least 50% at least 60%, at least 70%, at least 80%, or at least 90% smaller.

According to an embodiment, said enhanced therapeutic effect comprises smaller and/or reduced severity of conditions and/or symptoms. According to an embodiment, the primary terpene, the cannabinoids and optionally secondary terpenes are present in specific amounts, and the severity of the conditions and/or symptoms, as measured by methods known in the art, is at least 20% smaller compared with that of a product comprising the same amounts of cannabinoids and secondary terpenes and one half the amount of the primary terpene, at least 30%, at least 40%, at least 50% at least 60%, at least 70%, at least 80%, or at least 90% smaller.

According to an embodiment, said enhanced therapeutic effect comprises smaller and/or reduced consumption of other drugs. According to an embodiment, the primary terpene, the cannabinoids and optionally secondary terpenes are present in specific amounts, and the consumption of other drugs is reduced by at least 20% compared with that of a product comprising the same amounts of cannabinoids and secondary terpenes and one half the amount of said primary terpene, reduced by at least 30%, by at least 40%, by at least 50%, by at least 60%, by at least 70%, by at least 80%, or by at least 90%.

According to an embodiment, the administered product comprises tetrahydrocannabinol (THC) at a concentration of less than 5% by weight, and at least 0.5% by weight primary terpene. According to an embodiment, the product is applied to a child. According to an embodiment, the primary terpene is selected from the group consisting of limonene, linalool, eucalyptol, myrcene, caryophyllene, terpineol and combinations thereof. According to an embodiment, the composition comprises tetrahydrocannabinol (THC) in a concentration of less than 5%, less than 4%, less than 3%, less than 2%, or less than 1%. According to an embodiment, the primary terpene is in a concentration of at least 0.5%, at least 0.6%, at least 0.7%, at least 0.8%, at least 0.9%, or at least 1%. According to an embodiment, the composition comprises at least 2 of said primary terpenes, at least 3, at least 4, or at least 5. According to an embodiment, the primary terpene is selected from the group consisting of limonene, linalool, myrcene and combination thereof.

According to an embodiment, the administered product comprises CBD and optionally THC at CBD to THC weight/weight ratio greater than 1, wherein CBD concentration is less than 20% by weight and wherein primary terpene concentration is at least 0.5% by weight. According to an embodiment, the product is applied to a child. According to an embodiment, the primary terpene is selected from the group consisting of linalool, terpineol, ocimene, humulene, caryophyllene, eucalyptol, pinene, limonene and combinations thereof. According to an embodiment, the product comprises CBD and optionally THC at CBD to THC weight/weight ratio greater 2, greater than 3, greater than 4 or greater than 5. According to an embodiment, the composition comprises cannabidiol (CBD) and/or cannabidiolic acid (CBDa) in a concentration of less than 18%, less than 16%, less than 14%, less than 12%, or less than 10%. According to an embodiment, the composition comprises cannabidiol (CBD) and/or cannabidiolic acid (CBDa), wherein CBD and/or CBDa concentration is of 10 to 20%, 10 to 15%, 15 to 20%, 12-18%. According to an embodiment, the primary terpene is in a concentration of at least 0.5%, at least 0.6%, at least 0.7%, at least 0.8%, at least 0.9%, or at least 1%. According to an embodiment, the composition comprises at least 2 of said primary terpenes, at least 3, at least 4, or at least 5. According to an embodiment, the primary terpene is selected from the group consisting of linalool, terpineol, caryophyllene and combination thereof. According to an embodiment, the primary terpene is selected from the group consisting of linalool, terpineol, ocimene and combination thereof. According to an embodiment, the primary terpene is selected from the group consisting of eucalyptol, pinene, limonene and combination thereof. According to an embodiment, the primary terpene comprises caryophyllene and/or humulene.

According to an embodiment, the therapeutic effect is generated while administering the product in a vaporizer. According to an embodiment, the therapeutic effect is generated while administering the product by inhaling. According to an embodiment, the therapeutic effect is generated while administering the product by smoking. According to an embodiment, the therapeutic effect is generated while administering the product sublingually. According to an embodiment, the therapeutic effect is generated while applying the product, topically. According to an embodiment, the therapeutic effect is generated while administering the product in suppositories, including tampons and/or rectal candles. According to an embodiment, the therapeutic effect is generated while administering the product in a spray. According to an embodiment, the therapeutic effect is generated while administering the product as an edible, as a candy, as baked good, as a drink. According to an embodiment, the therapeutic effect is generated while administering the product as vaporizer liquid nasal preparation. According to an embodiment, the therapeutic effect is generated while administering the product as micro and nano-emulsions. According to an embodiment, the therapeutic effect is generated while administering the product as micro and nano-emulsions.

According to an embodiment said therapeutic effect treats diabetes and said administered product comprises at least one of CBD, THC, CBC, CBG, CBN, CBL, THCV and CBDV. According to an embodiment said therapeutic effect treats diabetes and said product comprises CBD and optionally THC at CBD to THC weight/weight ratio greater than 1, greater than 2, greater than 3, greater than 4 or greater than 5. According to an embodiment said therapeutic effect treats diabetes and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats diabetes and said primary terpene is selected from the group consisting of limonene, pinene, linalool, humulene, myrcene, phytol, geraniol, bisabolol, borneol, guaiol, ocimene, fenchol, terpineol, terpinene, eucalyptol and combinations thereof. According to an embodiment, the product comprises at least 2 of these terpenes, at least 3, at least 4, or at least 5 of the terpenes. According to an embodiment, the primary terpene is selected from the group consisting of limonene, linalool, geraniol and combinations thereof. According to an embodiment, the primary terpene is selected from the group consisting of limonene, linalool, geraniol, pinene, humulene, phytol and combinations thereof. According to various embodiments said primary terpene comprises limonene, pinene, linalool, humulene, myrcene, phytol, geraniol, bisabolol, borneol, guaiol, ocimene, fenchol, terpineol, terpinene and/or eucalyptol.

According to an embodiment said therapeutic effect treats including Crohn's disease and ulcerative colitis and said administered product comprises at least one of CBD, THC, CBC, CBG, CBN, CBL, THCV and CBDV. According to an embodiment said therapeutic effect treats including Crohn's disease and ulcerative colitis and said product comprises CBD and optionally THC at CBD to THC weight/weight ratio greater than 1, greater than 2, greater than 3, greater than 4 or greater than 5. According to an embodiment said therapeutic effect treats including Crohn's disease and ulcerative colitis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats including Crohn's disease and ulcerative colitis and said primary terpene is selected from the group consisting of limonene, caryophyllene, borneol, myrcene, pinene, terpinene, isopulegol, phellandrene, carene, carvacol, terpineol, humulene and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, myrcene and combinations thereof. According to an embodiment, the primary terpene is selected from the group consisting of limonene, caryophyllene, myrcene, pinene, carene, carvacol and combinations thereof. According to various embodiments said primary terpene comprises limonene, caryophyllene, borneol, myrcene, pinene, terpinene, isopulegol, phellandrene, carene, carvacol, terpineol and/or humulene. According to an embodiment, said therapeutic effect treats Crohn's disease and ulcerative colitis and the product further comprises a compound selected from the group consisting of linalyl acetate, geranyl acetate, eugenol, eugenyl acetate, piperine and combinations thereof. According to an embodiment, the product includes fenchol and fenchol forms less than 5% by weight of the total terpene content.

According to an embodiment said therapeutic effect stimulates the immune system and/or treats weakened immune system and said administered product comprises at least one of CBD, THC, CBC, CBG, CBN, CBL, THCV and CBDV. According to an embodiment said therapeutic effect stimulates the immune system and/or treats weakened immune system and said product comprises CBD and optionally THC at CBD to THC weight/weight ratio greater than 1, greater than 2, greater than 3, greater than 4 or greater than 5. According to an embodiment said therapeutic effect stimulates the immune system and/or treats weakened immune system and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect stimulates the immune system and/or treats weakened immune system and said primary terpene is selected from the group consisting of linalool, pinene, borneol, caryophyllene, geraniol, amyrin, terpinene, myrcene, eucalyptol, humulene and combinations thereof. According to an embodiment, the product comprises at least 2 of these terpenes, at least 3, at least 4, or at least 5 of the terpenes. According to an embodiment, the primary terpene is selected from the group consisting of linalool, caryophyllene, amyrin, and combinations thereof. According to an embodiment, the primary terpene is selected from the group consisting of linalool, caryophyllene, amyrin, pinene, terpinene, myrcene and combinations thereof. According to various embodiments said primary terpene comprises linalool, pinene, borneol, caryophyllene, geraniol, amyrin, terpinene, myrcene, eucalyptol and/or humulene.

According to an embodiment said therapeutic effect treats Fibromyalgia and said administered product comprises at least one of CBD, THC, CBC, CBG, CBN, CBL, THCV and CBDV. According to an embodiment said therapeutic effect treats Fibromyalgia and said product comprises CBD and optionally THC at CBD to THC weight/weight ratio greater than 1, greater than 2, greater than 3, greater than 4 or greater than 5. According to an embodiment said therapeutic effect treats Fibromyalgia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Fibromyalgia and said primary terpene is selected from the group consisting of linalool, caryophyllene, limonene, humulene, eucalyptol, amyrin, cycloartenol, pinene, sabinene, myrcene, terpinene, borneol, bisabolol and combinations thereof. According to an embodiment, the product comprises at least 2 of these terpenes, at least 3, at least 4, or at least 5 of the terpenes. According to an embodiment, the primary terpene is selected from the group consisting of linalool, caryophyllene, eucalyptol and combinations thereof. According to an embodiment, the primary terpene is selected from the group consisting of linalool, caryophyllene, eucalyptol, limonene, pinene, sabinene, myrcene and combinations thereof. According to various embodiments said primary terpene comprises linalool, caryophyllene, limonene, humulene, eucalyptol, amyrin, cycloartenol, pinene, sabinene, myrcene, terpinene, borneol and/or bisabolol. According to an embodiment, the product includes myrcene, humulene, bisabolol, borneol, limonene and/or linalool and myrcene, humulene, bisabolol, borneol, limonene and/or linalool forms less than 5% by weight of the total terpene content.

According to an embodiment said therapeutic effect treats nociceptive pain and said administered product comprises at least one of CBD, THC, CBC, CBG, CBN, CBL, THCV and CBDV. According to an embodiment said therapeutic effect treats nociceptive pain and said product comprises CBD and optionally THC at CBD to THC weight/weight ratio greater than 1, greater than 2, greater than 3, greater than 4 or greater than 5. According to an embodiment said therapeutic effect treats nociceptive pain and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats nociceptive pain and said primary terpene is selected from the group consisting of myrcene, linalool, caryophyllene, eucalyptol, cycloartenol, borneol, sabinene, camphene, terpineol, citronellol, geraniol, humulene, bisabolol, limonene and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, eucalyptol, terpineol, citronellol and combinations thereof. According to various embodiments said primary terpene comprises myrcene, linalool, caryophyllene, eucalyptol, cycloartenol, borneol, sabinene, camphene, terpineol, citronellol, geraniol, humulene, bisabolol and/or limonene.

According to an embodiment said therapeutic effect treats neuropathic pain and said administered product comprises at least one of CBD, THC, CBC, CBG, CBN, CBL, THCV and CBDV. According to an embodiment said therapeutic effect treats neuropathic pain and said product comprises CBD and optionally THC at CBD to THC weight/weight ratio greater than 1, greater than 2, greater than 3, greater than 4 or greater than 5. According to an embodiment said therapeutic effect treats neuropathic pain and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats neuropathic pain and said primary terpene is selected from the group consisting of caryophyllene, linalool, eucalyptol, amyrin, borneol, pinene, terpineol, limonene, nerolidol, geraniol, myrcene and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, eucalyptol and combinations thereof. According to an embodiment, the primary terpene is selected from the group consisting of caryophyllene, linalool, eucalyptol, borneol, limonene, myrcene and combinations thereof. According to an embodiment, the primary terpene is selected from the group consisting of pinene, terpineol, nerolidol and combinations thereof. According to various embodiments said primary terpene comprises caryophyllene, linalool, eucalyptol, amyrin, borneol, pinene, terpineol, limonene, nerolidol, geraniol and/or myrcene. According to an embodiment, the product includes humulene, bisabolol, borneol, limonene and/or linalool, and humulene, bisabolol, borneol, limonene and/or linalool forms less than 5% by weight of the total terpene content.

According to an embodiment said therapeutic effect treats pain and said product comprises at least one of CBD, THC, CBC, CBG, CBN, CBL, THCV and CBDV. According to an embodiment said therapeutic effect treats pain and said administered product comprises CBD and optionally THC at CBD to THC weight/weight ratio greater than 1, greater than 2, greater than 3, greater than 4 or greater than 5. According to an embodiment said therapeutic effect treats pain and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats pain and said primary terpene is selected from the group consisting of myrcene, linalool, humulene, eucalyptol, caryophyllene, caryophyllene oxide, amyrin, cycloartenol, borneol, sabinene, camphene, nerolidol, terpineol, geraniol, citronellol, camphor, bisabolol, limonene and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, eucalyptol, borneol, terpineol and combinations thereof. According to various embodiments said primary terpene comprises myrcene, linalool, humulene, eucalyptol, caryophyllene, caryophyllene oxide, amyrin, cycloartenol, borneol, sabinene, camphene, nerolidol, terpineol, geraniol, citronellol, camphor, bisabolol and/or limonene. According to an embodiment, said therapeutic effect treats pain and the product comprises a compound selected from the group consisting of linalyl acetate, geranyl acetate, eugenol, eugenyl acetate, piperine, methylis-oeugenol, Methyleugenol, menthol and combination thereof. According to an embodiment, the product includes humulene, bisabolol, borneol, limonene and/or linalool, wherein humulene, bisabolol, borneol, limonene and/or linalool forms less than 5% by weight of the total terpene content. According to an embodiment, said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis* and combinations thereof.

According to an embodiment said therapeutic effect treats arm or leg pain and said administered product comprises at least one of CBD, THC, CBC, CBG, CBN, CBL, THCV and CBDV. According to an embodiment said therapeutic effect treats arm or leg pain and said product comprises CBD and optionally THC at CBD to THC weight/weight ratio greater than 1, greater than 2, greater than 3, greater than 4 or greater than 5. According to an embodiment said therapeutic effect treats arm or leg pain and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats arm or leg pain and said primary terpene is selected from the group consisting of linalool, terpinene, pinene, limonene, terpineol, myrcene, nerolidol and combinations thereof. According to an embodiment, the product comprises at least 2 of these terpenes, at least 3, at least 4, or at least 5 of the terpenes. According to an embodiment, the primary terpene is selected from the group consisting of linalool, pinene, myrcene and combinations thereof. According to an embodiment, the primary terpene is selected from the group consisting of linalool, pinene, myrcene, limonene, terpineol, nerolidol and combinations thereof. According to various embodiments said primary terpene comprises linalool, terpinene, pinene, limonene, terpineol, myrcene and/or nerolidol.

According to an embodiment said therapeutic effect treats neurodegenerative diseases including Alzheimer disease, Parkinson disease, Huntington's disease, dystonia and/or Amyotrophic lateral sclerosis (ALS) and said administered product comprises at least one of CBD, THC, CBC, CBG, CBN, CBL, THCV and CBDV. According to an embodiment said therapeutic effect treats neurodegenerative diseases including Alzheimer disease, Parkinson disease, Huntington's disease, dystonia and/or Amyotrophic lateral sclerosis (ALS) and said product comprises CBD and optionally THC at CBD to THC weight/weight ratio greater than 1, greater than 2, greater than 3, greater than 4 or greater than 5. According to an embodiment said therapeutic effect treats neurodegenerative diseases including Alzheimer disease, Parkinson disease, Huntington's disease, dystonia and/or Amyotrophic lateral sclerosis (ALS) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats neurodegenerative diseases including Alzheimer disease, Parkinson disease, Huntington's disease, dystonia and/or Amyotrophic lateral sclerosis (ALS) and said primary terpene is selected from the group consisting of terpineol, caryophyllene, myrcene, terpineol, linalool, humulene, eucalyptol, pinene, pulegone, cymene, ocimene, limonene, nerolidol, sabinene, carene, citronellol, geraniol, menthol, borneol, terpinene, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, pinene, terpineol and combinations thereof. According to an embodiment, the primary terpene is selected from the group consisting of caryophyllene, linalool, pinene, terpineol, myrcene, terpineol, limonene, nerolidol, sabinene and combinations thereof. According to various embodiments said primary terpene comprises terpineol, caryophyllene, myrcene, terpineol, linalool, humulene, eucalyptol, pinene, pulegone, cymene, ocimene, limonene, nerolidol, sabinene, carene, citronellol, geraniol, menthol, borneol, terpinene, bisabolol and/or fenchol. According to an embodiment said therapeutic effect treats Alzheimer disease and said the primary terpene is selected from the group consisting of pinene, eucalyptol, linalool, terpineol, myrcene, caryophyllene and combinations thereof. According to an embodiment said therapeutic effect treats Alzheimer disease and said primary terpene is selected from the group consisting of pinene, eucalyptol, linalool and combinations thereof. According to an embodiment said therapeutic effect treats Parkinson disease, Huntington's disease, dystonia and/or Amyotrophic lateral sclerosis (ALS) and said primary terpene is selected from the group consisting caryophyllene, myrcene, linalool, pinene, limonene, nerolidol, sabinene, terpineol and combinations thereof. According to an embodiment said therapeutic effect treats Parkinson disease, Huntington's disease, dystonia and/or Amyotrophic lateral sclerosis (ALS) and said primary terpene is selected from the group consisting myrcene, linalool, pinene, nerolidol and combinations thereof. According to an embodiment, said therapeutic effect treats neurodegenerative diseases including Alzheimer, Parkinson disease, Huntington's disease, dystonia and/or Amyotrophic lateral sclerosis (ALS) and the product comprises a compound selected from the group consisting of linalyl acetate, geranyl acetate, menthol, piperine, eugenol, citronellyl formate, jasmone, benzy acetate, benzyl alcohol and combination thereof. According to an embodiment, the product includes pinene, myrcene and/or terpineol, and pinene, myrcene and/or terpineol forms less than 5% by weight of the total terpene content.

According to an embodiment said therapeutic effect treats multiple sclerosis and said administered product comprises at least one of CBD, THC, CBC, CBG, CBN, CBL, THCV and CBDV. According to an embodiment said therapeutic effect treats multiple sclerosis and said product comprises CBD and optionally THC at CBD to THC weight/weight ratio greater than 1, greater than 2, greater than 3, greater than 4 or greater than 5. According to an embodiment said therapeutic effect treats multiple sclerosis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats multiple sclerosis and said primary terpene is selected from the group consisting of caryophyllene, pinene, myrcene, limonene, humulene, citronellol, eucalyptol, caryophyllene oxide, linalool, amyrin, cycloartenol, cymene, terpinene, borneol, pulegol, nerolidol, terpineol, sabinene, geraniol and combinations thereof. According to an embodiment, the product comprises at least 2 of these terpenes, at least 3, at least 4, or at least 5 of the terpenes. According to an embodiment, the primary terpene is selected from the group consisting of caryophyllene, myrcene, linalool and combinations thereof. According to an embodiment, the primary terpene is selected from the group consisting of caryophyllene, myrcene, linalool, pinene, limonene, eucalyptol and combinations thereof. According to various embodiments said primary terpene comprises caryophyllene, pinene, myrcene, limonene, humulene, citronellol, eucalyptol, caryophyllene oxide, linalool, amyrin, cycloartenol, cymene, terpinene, borneol, pulegol, nerolidol, terpineol, sabinene and/or geraniol.

According to an embodiment said therapeutic effect treats Myasthenia gravis and said administered product comprises at least one of CBD, THC, CBC, CBG, CBN, CBL, THCV and CBDV. According to an embodiment said therapeutic effect treats Myasthenia gravis and said product comprises CBD and optionally THC at CBD to THC weight/weight ratio greater than 1, greater than 2, greater than 3, greater than 4 or greater than 5. According to an embodiment said therapeutic effect treats Myasthenia gravis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Myasthenia gravis and said primary terpene is selected from the group consisting of pinene, terpineol, eucalyptol, pulegone, cymene, ocimene, nerolidol, limonene, linalool, citronellol, geraniol, menthol, caryophyllene, borneol and combinations thereof. According to an embodiment, the product comprises at least 2 of these terpenes, at least 3, at least 4, or at least 5 of the terpenes. According to an embodiment, the primary terpene is selected from the group consisting of terpineol, eucalyptol, linalool and combinations thereof. According to an embodiment, the primary terpene is selected from the group consisting of terpineol, eucalyptol, linalool, pinene, nerolidol, limonene and combinations thereof. According to various embodiments said primary terpene comprises pinene, terpineol, eucalyptol, pulegone, cymene, ocimene, nerolidol, limonene, linalool, citronellol, geraniol, menthol, caryophyllene, and/or borneol. According to an embodiment, the product includes myrcene and/or pinene, and myrcene and/or pinene forms less than 5% by weight of the total terpene content.

According to an embodiment said therapeutic effect treats epilepsy and said administered product comprises at least one of CBD, THC, CBC, CBG, CBN, CBL, THCV and CBDV. According to an embodiment said therapeutic effect treats epilepsy and said product comprises CBD and optionally THC at CBD to THC weight/weight ratio greater than 1, greater than 2, greater than 3, greater than 4 or greater than 5. According to an embodiment said therapeutic effect treats epilepsy and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats epilepsy and said primary terpene is selected from the group consisting of linalool, terpineol, ocimene, myrcene, limonene, caryophyllene and combinations thereof. According to an embodiment, the product comprises at least 2 of these terpenes, at least 3, at least 4, or at least 5 of the terpenes. According to an embodiment, the primary terpene is selected from the group consisting of linalool, terpineol, ocimene and combinations thereof. According to various embodiments said primary terpene comprises linalool, terpineol, ocimene, myrcene, limonene and/or caryophyllene.

According to an embodiment said therapeutic effect treats cancer and/or cancer related symptom and said administered product comprises at least one of CBD, THC, CBC, CBG, CBN, CBL, THCV and CBDV. According to an embodiment said therapeutic effect treats cancer and/or cancer related symptom and said product comprises CBD and optionally THC at CBD to THC weight/weight ratio greater than 1, greater than 2, greater than 3, greater than 4 or greater than 5. According to an embodiment said therapeutic effect treats cancer and/or cancer related symptom and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats cancer and/or cancer related symptom and said primary terpene is selected from the group consisting of myrcene, limonene, caryophyllene, caryophyllene oxide, terpinene, citronellol, linalool, geraniol. Menthol. humulene, amyrin, cycloartenol, pinene, camphene, eucalyptol, terpineol, borneol and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, linalool and combinations thereof. According to an embodiment, the primary terpene is selected from the group consisting of limonene, caryophyllene, linalool, citronellol, myrcene, eucalyptol, pinene and combinations thereof. According to various embodiments said primary terpene comprises myrcene, limonene, caryophyllene, caryophyllene oxide, terpinene, citronellol, linalool, geraniol, menthol, humulene, amyrin, cycloartenol, pinene, camphene, eucalyptol, terpineol and/or borneol. According to an embodiment, said therapeutic effect treats cancer and/or cancer related symptom and the product comprises a compound selected from the group consisting of linalyl acetate, geranyl acetate, eugenol, eugenyl acetate, piperine, methylis-oeugenol, Methyleugenol, menthol and combination thereof.

According to an embodiment said therapeutic effect treats stroke and/or traumatic brain injury and said administered product comprises at least one of CBD, THC, CBC, CBG, CBN, CBL, THCV and CBDV. According to an embodiment said therapeutic effect treats stroke and/or traumatic brain injury and said product comprises CBD and optionally THC at CBD to THC weight/weight ratio greater than 1, greater than 2, greater than 3, greater than 4 or greater than 5. According to an embodiment said therapeutic effect treats stroke and/or traumatic brain injury and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats stroke and/or traumatic brain injury and said primary terpene is selected from the group consisting of myrcene, terpinene, caryophyllene, caryophyllene oxide, pinene, limonene, humulene, citronellol, eucalyptol, linalool, amyrin, cycloartenol, terpineol, thymol, eucalyptol, geraniol, carvacrol, thymol, cardinol, menth-2-en-1-ol, carotol and combinations thereof. According to an embodiment, the product comprises at least 2 of these terpenes, at least 3, at least 4, or at least 5 of the terpenes. According to an embodiment, the primary terpene is selected from the group consisting of myrcene, caryophyllene, limonene and combinations thereof. According to an embodiment, the primary terpene is selected from the group consisting of myrcene, caryophyllene, limonene, pinene, humulene, terpineol, thymol, eucalyptol and combinations thereof. According to various embodiments said primary terpene comprises myrcene, terpinene, caryophyllene, caryophyllene oxide, pinene, limonene, humulene, citronellol, eucalyptol, linalool, amyrin, cycloartenol, terpineol, thymol, eucalyptol, geraniol, carvacrol, thymol, cardinol, menth-2-en-1-ol and/or carotol. According to an embodiment, the product includes fenchol and/or borneol, and fenchol and/or borneol forms less than 5% by weight of the total terpene content.

According to an embodiment said therapeutic effect treats addiction, including addiction to drugs, smoking, drinks, food, gambling, sex, and sports and said administered product comprises at least one of CBD, THC, CBC, CBG, CBN, CBL, THCV and CBDV. According to an embodiment said therapeutic effect treats addiction, including addiction to drugs, smoking, drinks, food, gambling, sex, and sports and said product comprises CBD and optionally THC at CBD to THC weight/weight ratio greater than 1, greater than 2, greater than 3, greater than 4 or greater than 5. According to an embodiment said therapeutic effect treats addiction, including addiction to drugs, smoking, drinks, food, gambling, sex, and sports and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats addiction, including addiction to drugs, smoking, drinks, food, gambling, sex, and sports and said primary terpene is selected from the group consisting of caryophyllene, pinene, myrcene, limonene, linalool, terpineol and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, terpineol and combinations thereof. According to various embodiments said primary terpene comprises caryophyllene, pinene, myrcene, limonene, linalool and/or terpineol.

According to an embodiment said therapeutic effect treats inflammatory airway diseases including asthma and/or chronic obstructive pulmonary disease (COPD) and said administered product comprises at least one of CBD, THC, CBC, CBG, CBN, CBL, THCV and CBDV. According to an embodiment said therapeutic effect treats inflammatory airway diseases including asthma and/or chronic obstructive pulmonary disease (COPD) and said product comprises CBD and optionally THC at CBD to THC weight/weight ratio greater than 1, greater than 2, greater than 3, greater than 4 or greater than 5. According to an embodiment said therapeutic effect treats inflammatory airway diseases including asthma and/or chronic obstructive pulmonary disease (COPD) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats inflammatory airway diseases including asthma and/or chronic obstructive pulmonary disease (COPD) and said primary terpene is selected from the group consisting of pinene, eucalyptol, limonene, humulene, camphene, caryophyllene and combinations thereof. According to an embodiment, the product comprises at least 2 of these terpenes, at least 3, at least 4, or at least 5 of the terpenes. According to an embodiment, the primary terpene is selected from the group consisting of pinene, eucalyptol, humulene, and combinations thereof. According to various embodiments said primary terpene comprises pinene, eucalyptol, limonene, humulene, camphene and/or caryophyllene.

According to an embodiment said therapeutic effect treats cerebral palsy (CP) and said administered product comprises at least one of CBD, THC, CBC, CBG, CBN, CBL, THCV and CBDV. According to an embodiment said therapeutic effect treats cerebral palsy (CP) and said product comprises CBD and optionally THC at CBD to THC weight/weight ratio greater than 1, greater than 2, greater than 3, greater than 4 or greater than 5. According to an embodiment said therapeutic effect treats cerebral palsy (CP) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats cerebral palsy (CP) and said primary terpene is selected from the group consisting of myrcene, pinene, linalool, humulene, nerolidol, limonene, terpineol, sabinene and combinations thereof. According to an embodiment, the product comprises at least 2 of these terpenes, at least 3, at least 4, or at least 5 of the terpenes. According to an embodiment, the primary terpene is selected from the group consisting of myrcene, pinene, nerolidol and combinations thereof. According to an embodiment, the primary terpene is selected from the group consisting of linalool, limonene, sabinene and combinations thereof. According to various embodiments said primary terpene comprises myrcene, pinene, linalool, humulene, nerolidol, limonene, terpineol and/or sabinene.

According to an embodiment said therapeutic effect treats autism and/or autism spectrum disorder and said product comprises at least one of CBD, THC, CBC, CBG, CBN, CBL, THCV and CBDV. According to an embodiment said therapeutic effect treats autism and/or autism spectrum disorder and said administered product comprises CBD and optionally THC at CBD to THC weight/weight ratio greater than 1, greater than 2, greater than 3, greater than 4 or greater than 5. According to an embodiment said therapeutic effect treats autism and/or autism spectrum disorder and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats autism and/or autism spectrum disorder and said primary terpene is selected from the group consisting of limonene, caryophyllene, pinene, myrcene, humulene, citronellol, eucalyptol, linalool, terpineol, ocimene, geraniol, menthol, borneol, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of pinene, eucalyptol, linalool and combinations thereof. According to an embodiment, the primary terpene is selected from the group consisting of pinene, eucalyptol, linalool, caryophyllene, myrcene, terpineol and combinations thereof. According to various embodiments said primary terpene comprises limonene, caryophyllene, pinene, myrcene, humulene, citronellol, eucalyptol, linalool, terpinenol, ocimene, geraniol, menthol, borneol, bisabolol and/or fenchol.

According to an embodiment said therapeutic effect treats hyperactivity disorder (ADHD), attention deficit disorder (ADD) and/or obsessive-compulsive disorder (OCD) and said administered product comprises at least one of CBD, THC, CBC, CBG, CBN, CBL, THCV and CBDV. According to an embodiment said therapeutic effect treats hyperactivity disorder (ADHD), attention deficit disorder (ADD) and/or obsessive-compulsive disorder (OCD) and said product comprises CBD and optionally THC at CBD to THC weight/weight ratio greater than 1, greater than 2, greater than 3, greater than 4 or greater than 5. According to an embodiment said therapeutic effect treats hyperactivity disorder (ADHD), attention deficit disorder (ADD) and/or obsessive-compulsive disorder (OCD) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats hyperactivity disorder (ADHD), attention deficit disorder (ADD) and/or obsessive-compulsive disorder (OCD) and said primary terpene is selected from the group consisting of linalool, eucalyptol, terpineol, myrcene, pinene, pulegone, caryophyllene, geraniol, citronellol, menthol, caryophyllene, pinene, borneol, bisabolol, fenchol and combinations thereof. According to an embodiment, the product comprises at least 2 of these terpenes, at least 3, at least 4, or at least 5 of the terpenes. According to an embodiment said therapeutic effect treats hyperactivity disorder (ADHD) and/or attention deficit disorder (ADD) and said primary terpene is selected from the group consisting of linalool, eucalyptol, myrcene, and combinations thereof. According to an embodiment, the primary terpene is selected from the group consisting of linalool, eucalyptol, myrcene, caryophyllene, pinene, borneol and combinations thereof. According to an embodiment said therapeutic effect treats obsessive-compulsive disorder (OCD) and said primary terpene is selected from the group consisting of limonene, eucalyptol, pinene and combination thereof. According to an embodiment, the primary terpene is selected from the group consisting of linalool, caryophyllene, borneol and combination thereof. According to various embodiments said primary terpene comprises linalool, eucalyptol, terpineol, myrcene, pinene, pulegone, caryophyllene, geraniol, citronellol, menthol, caryophyllene, pinene, borneol, bisabolol and/or fenchol.

According to an embodiment said therapeutic effect treats Tourette syndrome, motor spasms, motor tics and/or vocal tics and said administered product comprises at least one of CBD, THC, CBC, CBG, CBN, CBL, THCV and CBDV. According to an embodiment said therapeutic effect treats Tourette syndrome, motor spasms, motor tics and/or vocal tics and said product comprises CBD and optionally THC at CBD to THC weight/weight ratio greater than 1, greater than 2, greater than 3, greater than 4 or greater than 5. According to an embodiment said therapeutic effect treats Tourette syndrome, motor spasms, motor tics and/or vocal tics and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Tourette syndrome, motor spasms, motor tics and/or vocal tics and said primary terpene is selected from the group consisting of myrcene, linalool, limonene, pinene, nerolidol, caryophyllene, eucalyptol, geraniol, menthol, borneol, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of myrcene, limonene, nerolidol and combinations thereof. According to an embodiment, the primary terpene is selected from the group consisting of linalool, pinene, eucalyptol and combinations thereof. According to various embodiments said primary terpene comprises myrcene, linalool, limonene, pinene, nerolidol, caryophyllene, eucalyptol, geraniol, menthol, borneol, bisabolol and/or fenchol.

According to an embodiment said therapeutic effect treats psoriasis and said administered product comprises at least one of CBD, THC, CBC, CBG, CBN, CBL, THCV and CBDV. According to an embodiment said therapeutic effect treats psoriasis and said product comprises CBD and optionally THC at CBD to THC weight/weight ratio greater than 1, greater than 2, greater than 3, greater than 4 or greater than 5. According to an embodiment said therapeutic effect treats psoriasis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats psoriasis and said primary terpene is selected from the group consisting of linalool, caryophyllene, limonene and combinations thereof. According to an embodiment, the product comprises at least 2 of these terpenes or all 3 of the terpenes. According to an embodiment, the primary terpene is selected from the group consisting of linalool, caryophyllene, limonene and combinations thereof. According to various embodiments said primary terpene comprises linalool, caryophyllene and/or limonene.

According to an embodiment said therapeutic effect treats dermatophytes and said administered product comprises at least one of CBD, THC, CBC, CBG, CBN, CBL, THCV and CBDV. According to an embodiment said therapeutic effect treats dermatophytes and said product comprises CBD and optionally THC at CBD to THC weight/weight ratio greater than 1, greater than 2, greater than 3, greater than 4 or greater than 5. According to an embodiment said therapeutic effect treats dermatophytes and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats dermatophytes and said primary terpene is selected from the group consisting of limonene, caryophyllene, caryophyllene oxide, nerolidol, eucalyptol, terpinene, cycloartenol, amyrin, campene and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, caryophyllene oxide and combinations thereof. According to an embodiment, the primary terpene is selected from the group consisting of limonene, caryophyllene, caryophyllene oxide, nerolidol, eucalyptol, terpinene and combinations thereof. According to various embodiments said primary terpene comprises limonene, caryophyllene, caryophyllene oxide, nerolidol, eucalyptol, terpinene, cycloartenol, amyrin and/or campene.

According to an embodiment said therapeutic effect treats *candida* infection and said administered product comprises at least one of CBD, THC, CBC, CBG, CBN, CBL, THCV and CBDV. According to an embodiment said therapeutic effect treats *candida* infection and said product comprises CBD and optionally THC at CBD to THC weight/weight ratio greater than 1, greater than 2, greater than 3, greater than 4 or greater than 5. According to an embodiment said therapeutic effect treats *candida* infection and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats *candida* infection and said primary terpene is selected from the group consisting of pinene, limonene, caryophyllene, caryophyllene oxide, nerolidol, eucalyptol, terpinene, terpineol, myrcene, cycloartenol, citronellol, amyrin, camphene, cymene, Ocimene, humulene, farnesene, guaiol, eudesmol, friedelin, linalool, camphor, menthol, thymol, carvacrol, eugenol, farnesol, citronellol, geraniol, citral, ionone and combinations thereof. According to an embodiment, the product comprises at least 2 of these terpenes, at least 3, at least 4, or at least 5 of the terpenes. According to an embodiment, the primary terpene is selected from the group consisting of thymol, carvacrol, eugenol and combinations thereof. According to an embodiment, the primary terpene is selected from the group consisting of thymol, carvacrol, eugenol, nerolidol, linalool, farnesol, citronellol, geraniol, citral and combinations thereof. According to various embodiments said primary terpene comprises pinene, limonene, caryophyllene, caryophyllene oxide, nerolidol, eucalyptol, terpinene, terpineol, myrcene, cycloartenol, citronellol, amyrin, camphene, cymene, Ocimene, humulene, farnesene, guaiol, eudesmol, friedelin, linalool, camphor, menthol, thymol, carvacrol, eugenol, farnesol, citronellol, geraniol, citral and/or ionone.

According to an embodiment said therapeutic effect treats leishmaniasis and said administered product comprises at least one of CBD, THC, CBC, CBG, CBN, CBL, THCV and CBDV. According to an embodiment said therapeutic effect treats leishmaniasis and said product comprises CBD and optionally THC at CBD to THC weight/weight ratio greater than 1, greater than 2, greater than 3, greater than 4 or greater than 5. According to an embodiment said therapeutic effect treats leishmaniasis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats leishmaniasis and said primary terpene is selected from the group consisting of linalool, nerolidol, pinene, caryophyllene and/or eucalyptol. According to an embodiment said primary terpene is linalool and/or nerolidol.

According to an embodiment said therapeutic effect treats Methycillin-resistant *Staphylococcus aureus* (MRSA) and said administered product comprises at least one of CBD, THC, CBC, CBG, CBN, CBL, THCV and CBDV. According to an embodiment said therapeutic effect treats Methycillin-resistant *Staphylococcus aureus* (MRSA) and said product comprises CBD and optionally THC at CBD to THC weight/weight ratio greater than 1, greater than 2, greater than 3, greater than 4 or greater than 5. According to an embodiment said therapeutic effect treats Methycillin-resistant *Staphylococcus aureus* (MRSA) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Methycillin-resistant *Staphylococcus aureus* (MRSA) and said primary terpene is selected from the group consisting of pinene, caryophyllene, caryophyllene oxide, limonene, nerolidol, cycloartenol, amyrin and combinations thereof. According to an embodiment, the product comprises at least 2 of these terpenes, at least 3, at least 4, or at least 5 of the terpenes. According to an embodiment, the primary terpene is selected from the group consisting of pinene, caryophyllene, limonene, amyrin and combinations thereof. According to various embodiments said primary terpene comprises pinene, caryophyllene, caryophyllene oxide, limonene, nerolidol, cycloartenol and/or amyrin.

According to an embodiment said therapeutic effect treats malaria and said administered product comprises at least one of CBD, THC, CBC, CBG, CBN, CBL, THCV and CBDV. According to an embodiment said therapeutic effect treats malaria and said product comprises CBD and optionally THC at CBD to THC weight/weight ratio greater than 1, greater than 2, greater than 3, greater than 4 or greater than 5. According to an embodiment said therapeutic effect treats malaria and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats malaria and said primary terpene is selected from the group consisting of caryophyllene, nerolidol, pinene, eucalyptol, limonene and combinations thereof. According to an embodiment, the product comprises at least 2 of these terpenes, at least 3, at least 4, or at least 5 of the terpenes. According to an embodiment, the primary terpene is selected from the group consisting of caryophyllene, nerolidol, pinene and combinations thereof. According to various embodiments said primary terpene comprises caryophyllene, nerolidol, pinene, eucalyptol and/or limonene.

According to an embodiment said therapeutic effect treats acne and said administered product comprises at least one of CBD, THC, CBC, CBG, CBN, CBL, THCV and CBDV. According to an embodiment said therapeutic effect treats acne and said product comprises CBD and optionally THC at CBD to THC weight/weight ratio greater than 1, greater than 2, greater than 3, greater than 4 or greater than 5. According to an embodiment said therapeutic effect treats acne) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats acne and said primary terpene is selected from the group consisting of limonene, linalool, nerolidol, pinene, terpineol and combinations thereof. According to an embodiment, the product comprises at least 2 of these terpenes, at least 3, at least 4, or all 5 of the terpenes. According to an embodiment, the primary terpene is selected from the group consisting of limonene, pinene, terpineol and combinations thereof. According to various embodiments said primary terpene comprises limonene, linalool, nerolidol, pinene and/or terpineol.

According to an embodiment said therapeutic effect treats allergy and said administered product comprises at least one of CBD, THC, CBC, CBG, CBN, CBL, THCV and CBDV. According to an embodiment said therapeutic effect treats allergy and said product comprises CBD and optionally THC at CBD to THC weight/weight ratio greater than 1, greater than 2, greater than 3, greater than 4 or greater than 5. According to an embodiment said therapeutic effect treats allergy and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats allergy and said primary terpene is selected from the group consisting of camphene, pinene, borneol, caryophyllene, geraniol and combinations thereof. According to an embodiment, the product comprises at least 2 of these terpenes, at least 3, at least 4, or all 5 of the terpenes. According to an embodiment, the primary terpene is selected from the group consisting of camphene, pinene, caryophyllene and combinations thereof. According to various embodiments said primary terpene comprises camphene, pinene, borneol, caryophyllene and/or geraniol.

According to an embodiment said therapeutic effect treats osteoporosis and said administered product comprises at least one of CBD, THC, CBC, CBG, CBN, CBL, THCV and CBDV. According to an embodiment said therapeutic effect treats osteoporosis and said product comprises CBD and optionally THC at CBD to THC weight/weight ratio greater than 1, greater than 2, greater than 3, greater than 4 or greater than 5. According to an embodiment said therapeutic effect treats osteoporosis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats osteoporosis and said the primary terpene is selected from the group consisting of caryophyllene, caryophyllene oxide, carene, eucalyptol, sabinene, pinene, limonene, borneol, thymol, camphor and combinations thereof. According to an embodiment, the product comprises at least 2 of these terpenes, at least 3, at least 4, or at least 5 of the terpenes. According to an embodiment, the primary terpene is selected from the group consisting of caryophyllene, carene, camphor and combinations thereof. According to an embodiment, the primary terpene is selected from the group consisting of caryophyllene, carene, camphor, pinene, limonene, borneol and combinations thereof. According to various embodiments said primary terpene comprises caryophyllene oxide, eucalyptol, sabinene, pinene, limonene, thymol and/or camphor. According to an embodiment, said therapeutic effect treats osteoporosis said product and comprises a herbal extract selected from the group consisting of extracts of *Angelica sinensis, Cimicifuga (Actaea) racemosa, Dioscorea villosa, Trifolium pratense* and combinations thereof.

According to an embodiment said therapeutic effect treats sleep disorder and/or insomnia and said administered product comprises at least one of CBD, THC, CBC, CBG, CBN, CBL, THCV and CBDV. According to an embodiment said therapeutic effect treats sleep disorder and/or insomnia and said product comprises CBD and optionally THC at CBD to THC weight/weight ratio greater than 1, greater than 2, greater than 3, greater than 4 or greater than 5. According to an embodiment said therapeutic effect treats sleep disorder and/or insomnia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats sleep disorder and/or insomnia and said the primary terpene is selected from the group consisting of linalool, caryophyllene, myrcene, terpineol, terpinene, citronellol, eucalyptol, nerolidol, sabinene, pinene, limonene, borneol, fenchol, bisabolol humulene, phytol, citral and combinations thereof. According to an embodiment, the product comprises at least 2 of these terpenes, at least 3, at least 4, or at least 5 of the terpenes. According to an embodiment, the primary terpene is selected from the group consisting of linalool, terpineol, myrcene and combinations thereof. According to an embodiment, the primary terpene is selected from the group consisting of linalool, terpineol, myrcene, caryophyllene, terpinene, borneol and combinations thereof. According to an embodiment, the primary terpene comprises terpineol, citronellol and/or linalool. According to various embodiments said primary terpene comprises terpineol, terpinene, citronellol, eucalyptol, nerolidol, sabinene, pinene, limonene, borneol, fenchol, bisabolol, phytol and/or humulene. According to an embodiment, said therapeutic effect treats sleep disorder and/or insomnia and the product comprises a compound selected from the group consisting of linalyl acetate and/or chamazulene. According to an embodiment, said therapeutic effect treats sleep disorder and/or insomnia and said product comprises a herbal extract selected from the group consisting of extracts of *Avena sativa, Cimicifuga (actaea) racemosa, Humulus lupulus, Hypericum perforatum, Lavendula officinalis, Melissa officinalis, Passiflora incarnata, Valeriana officinalis* and combinations thereof According to an embodiment, the product includes caryophyllene, and caryophyllene forms less than 5% by weight of the total terpene content.

According to an embodiment said therapeutic effect treats anxiety, irritability, nervousness, restless, stress, depression, general discomfort, mood problems and/or affect disorder and said administered product comprises at least one of CBD, THC, CBC, CBG, CBN, CBL, THCV and CBDV. According to an embodiment said therapeutic effect treats anxiety, irritability, nervousness, restless, stress, depression, general discomfort, mood problems and/or affect disorder and said product comprises CBD and optionally THC at CBD to THC weight/weight ratio greater than 1, greater than 2, greater than 3, greater than 4 or greater than 5. According to an embodiment said therapeutic effect treats anxiety, irritability, nervousness, restless, stress, depression, general discomfort, mood problems and/or affect disorder and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats anxiety, irritability, nervousness, restless, stress, depression, general discomfort, mood problems and/or affect disorder and said the primary terpene is selected from the group consisting of limonene, linalool, terpineol, citronellol, eucalyptol, caryophyllene, geraniol, menthol, iso-menthone, germacrene, pinene, citronellol, cardinol, neral, geranial, myrcene, terpinene, menth-2-en-1-ol, humulene, bisabolol, borneol, fenchol, nerolidol, phellandrene and combinations thereof. According to an embodiment, the product comprises at least 2 of these terpenes, at least 3, at least 4, or at least 5 of the terpenes. According to an embodiment, the primary terpene is selected from the group consisting of limonene, linalool, eucalyptol and combinations thereof. According to an embodiment, the primary terpene is selected from the group consisting of limonene, linalool, eucalyptol, terpineol, caryophyllene, pinene, myrcene and combinations thereof. According to an embodiment, the primary terpene is selected from the group consisting of limonene, linalool, caryophyllene, bisabolol and combinations thereof. According to an embodiment, the primary terpene is selected from the group consisting of limonene, linalool, pinene, humulene and combinations thereof. According to various embodiments said primary terpene comprises terpineol, citronellol, caryophyllene, geraniol, menthol, iso-menthone, germacrene, pinene, citronellol, cardinol, neral, geranial, myrcene, terpinene, menth-2-en-1-ol, humulene, bisabolol, borneol, nerolidol phellandrene and/or fenchol. According to an embodiment, said therapeutic effect treats anxiety, irritability, nervousness, restless, stress, depression, general discomfort, mood problems and/or affect disorder and the product comprises a compound selected from the group consisting of linalyl acetate, geranyl acetate, menthol, piperine, eugenol, citronellyl formate, jasmone, benzy acetate, benzyl alcohol and combinations thereof. According to an embodiment, said therapeutic effect treats anxiety, irritability, nervousness, restless, stress, depression, general discomfort, mood problems and/or affect disorder and said product comprises a herbal extract selected from the group consisting of extracts of *Avena sativa, Bacopa monnieri, Centella* (*Hydrocotyl*) *asiatica, Humulus lupulus, Hypericum perforatum, Melissa officinalis, Passiflora incarnata, Valeriana officinalis* and combinations thereof. According to an embodiment, the product includes bisabolol, nerolidol, terpinene, myrcene and/or pinene bisabolol, nerolidol, terpinene, myrcene and/or pinene, and bisabolol, nerolidol, terpinene and/or pinene forms less than 5% by weight of the total terpene content.

According to an embodiment said therapeutic effect treats difficulty in concentration, memory loss, and/or dementia and said administered product comprises at least one of CBD, THC, CBC, CBG, CBN, CBL, THCV and CBDV. According to an embodiment said therapeutic effect treats difficulty in concentration, memory loss, and/or dementia and said product comprises CBD and optionally THC at CBD to THC weight/weight ratio greater than 1, greater than 2, greater than 3, greater than 4 or greater than 5. According to an embodiment said therapeutic effect treats difficulty in concentration, memory loss, and/or dementia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats difficulty in concentration, memory loss, and/or dementia and said the primary terpene is selected from the group consisting of pinene, pulegone, eucalyptol, terpineol, cymene, ocimene, limonene, linalool, caryophyllene, humulene, carene and combinations thereof. According to an embodiment, the product comprises at least 2 of these terpenes, at least 3, at least 4, or at least 5 of the terpenes. According to an embodiment, the primary terpene is selected from the group consisting of eucalyptol, pinene, limonene and combinations thereof. According to an embodiment, the primary terpene is selected from the group consisting of eucalyptol, pinene, limonene, terpineol, humulene, carene and combinations thereof. According to various embodiments said primary terpene comprises pinene, pulegone, eucalyptol, terpineol, cymene, ocimene, limonene, linalool, caryophyllene, humulene and/or carene. According to an embodiment said therapeutic effect treats difficulty in concentration, memory loss, and/or dementia and said product comprises a herbal extract selected from the group consisting of extracts of *Asphalentum ponjabianum-mumio, Bacopa monnieri, Centella* (*hydrocotyl*) *asiatica, Eleutherococcus senticosus, Ginkgo biloba, Lepidium meyenii, Lycium barbarum, Paullinia cupana, Rhodiola rosea* and combinations thereof.

According to an embodiment said therapeutic effect treats muscle pain, myalgia, spasticity, muscle tension, cramps and/or spasms and said administered product comprises at least one of CBD, THC, CBC, CBG, CBN, CBL, THCV and CBDV. According to an embodiment said therapeutic effect treats muscle pain, myalgia, spasticity, muscle tension, cramps and/or spasms and said product comprises CBD and optionally THC at CBD to THC weight/weight ratio greater than 1, greater than 2, greater than 3, greater than 4 or greater than 5. According to an embodiment said therapeutic effect treats muscle pain, myalgia, spasticity, muscle tension, cramps and/or spasms and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats muscle pain, myalgia, spasticity, muscle tension, cramps and/or spasms and said primary terpene is selected from the group consisting of myrcene, pinene, nerolidol, linalool, humulene, caryophyllene, limonene, bisabolol, sabinene, citral, eucalyptol, terpineol, geraniol and combinations thereof. According to an embodiment, the product comprises at least 2 of these terpenes, at least 3, at least 4, or at least 5 of the terpenes. According to an embodiment, the primary terpene is selected from the group consisting of myrcene, pinene, limonene and combinations thereof. According to an embodiment, the primary terpene is selected from the group consisting of myrcene, pinene, limonene, nerolidol, linalool, caryophyllene, sabinene and combinations thereof. According to an embodiment, the primary terpene is selected from the group consisting of myrcene, pinene, nerolidol, linalool, humulene and combinations thereof. According to various embodiments said primary terpene comprises myrcene, pinene, nerolidol, linalool, humulene, caryophyllene, limonene, bisabolol, sabinene, citral, eucalyptol, geraniol and/or terpineol. According to an embodiment said therapeutic effect treats cramps and/or spasms and said primary terpene is selected from the group consisting of myrcene, pinene, nerolidol, sabinene, eucalyptol and combinations thereof. According to an embodiment said primary terpene is selected from the group consisting of myrcene, linalool, eucalyptol and combinations thereof. According to an embodiment said therapeutic effect treats muscle pain, myalgia, spasticity, muscle tension, cramps and/or spasms and said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis, Chamaemelum, Valeriana edulis* and combinations thereof.

According to an embodiment said therapeutic effect treats fatigue, weakness, decreased mental energy, decreased physical energy, dizziness and/or deficits in balance and said administered product comprises at least one of CBD, THC, CBC, CBG, CBN, CBL, THCV and CBDV. According to an embodiment said therapeutic effect treats fatigue, weakness, decreased mental energy, decreased physical energy, dizziness and/or deficits in balance and said product comprises CBD and optionally THC at CBD to THC weight/weight ratio greater than 1, greater than 2, greater than 3, greater than 4 or greater than 5. According to an embodiment said therapeutic effect treats fatigue, weakness, decreased mental energy, decreased physical energy, dizziness and/or deficits in balance and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats fatigue, weakness, decreased mental energy, decreased physical energy, dizziness and/or deficits in balance and said the primary terpene is selected from the group consisting of pinene, limonene, terpinene, eucalyptol, myrcene, terpineol, linalool, caryophyllene, borneol and combinations thereof. According to an embodiment, the product comprises at least 2 of these terpenes, at least 3, at least 4, or at least 5 of the terpenes. According to an embodiment, the primary terpene is selected from the group consisting of pinene, terpinene, eucalyptol and combinations thereof. According to an embodiment, the primary terpene is selected from the group consisting of limonene, myrcene, borneol and combinations thereof. According to various embodiments said primary terpene comprises terpinene, myrcene, borneol and/or caryophyllene. According to an embodiment said therapeutic effect treats fatigue, weakness, decreased mental energy, decreased physical energy, dizziness and/or deficits in balance and said product comprises a herbal extract selected from the group consisting of extracts of *Eleutherococcus senticosus, Ganoderma lucidum, Grifola frondosa, Lentinula edodes, Lepidium meyenii, Panax ginseng, Rhodiola rosea* and combinations thereof.

According to an embodiment said therapeutic effect treats itchy skin, pruritus and/or chronic pruritus, wrinkles, stretch marks and/or skin burns and said administered product comprises at least one of CBD, THC, CBC, CBG, CBN, CBL, THCV and CBDV. According to an embodiment said therapeutic effect treats itchy skin, pruritus and/or chronic pruritus, wrinkles, stretch marks and/or skin burns and said product comprises CBD and optionally THC at CBD to THC weight/weight ratio greater than 1, greater than 2, greater than 3, greater than 4 or greater than 5. According to an embodiment said therapeutic effect treats itchy skin, pruritus and/or chronic pruritus, wrinkles, stretch marks and/or skin burns and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats itchy skin, pruritus and/or chronic pruritus, wrinkles, stretch marks and/or skin burns and said the primary terpene is selected from the group consisting of linalool limonene, nerolidol, pinene terpineol, myrcene, geraniol, nerol, citronellol, farnesol, carotol, sabinene and combinations thereof. According to an embodiment, the product comprises at least 2 of these terpenes, at least 3, at least 4, or at least 5 of the terpenes. According to an embodiment, the primary terpene is selected from the group consisting of linalool, terpineol, geraniol and combinations thereof. According to an embodiment said therapeutic effect treats skin burns and said the primary terpene is linalool and/or sabinene. According to an embodiment said therapeutic effect treats wrinkles, stretch marks and said the primary terpene is selected from the group consisting of geraniol, linalool, citronellol and combinations thereof. According to various embodiments said primary terpene comprises limonene, nerolidol, pinene myrcene, nerol, citronellol, farnesol, linalool, terpineol, geraniol and/or carotol. According to an embodiment, said therapeutic effect treats itchy skin, pruritus and/or chronic pruritus, wrinkles, stretch marks and/or skin burns and the product comprises a compound selected from the group consisting of linalyl acetate, citronellyl formate, eugenol, benzy acetate, benzyl alcohol, and combinations thereof. According to an embodiment said therapeutic effect treats itchy skin, pruritus and/or chronic pruritus, wrinkles, stretch marks and/or skin burns and said product comprises a herbal extract selected from the group consisting of extracts of *Glycyrrhiza glabra, Plantago* spp, *Symphytum officinalis, Trifolium pratense, Trigonella foenum graecum, Ulmus rubra\fulva, Verbascum thapsus* and combinations thereof.

According to an embodiment said therapeutic effect treats headache and/or migraine and said administered product comprises at least one of CBD, THC, CBC, CBG, CBN, CBL, THCV and CBDV. According to an embodiment said therapeutic effect treats headache and/or migraine and said product comprises CBD and optionally THC at CBD to THC weight/weight ratio greater than 1, greater than 2, greater than 3, greater than 4 or greater than 5. According to an embodiment said therapeutic effect treats headache and/or migraine and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats headache and/or migraine and said the primary terpene is selected from the group consisting of myrcene, linalool, caryophyllene, eucalyptol, limonene, nerolidol, fenchol, humulene, guaiol, borneol, pinene, bisabolol, terpinene, terpineol and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, limonene, nerolidol, fenchol and combinations thereof. According to various embodiments said primary terpene comprises of myrcene, linalool, caryophyllene, eucalyptol, limonene, nerolidol, fenchol, humulene, guaiol, borneol, pinene, terpinene, terpineol and/or bisabolol. According to an embodiment, the product includes linalool, bisabolol and/or humulene wherein linalool, bisabolol and/or humulene forms less than 5% by weight of the total terpene content. According to an embodiment said therapeutic effect treats headache and/or migraine and said product comprises a herbal extract selected from the group consisting of extracts of *Angelica sinensis, Corydalis yanhusuo, Piscidia erythrina, Rosmarinus officinalis, Stachys betonica, Tanacetum parthenium, Verbena officinalis* and combinations thereof.

According to an embodiment said therapeutic effect treats weight gain and/or reduces appetite and said administered product comprises at least one of CBD, THC, CBC, CBG, CBN, CBL, THCV and CBDV. According to an embodiment said therapeutic effect treats weight gain and/or reduces appetite and said product comprises CBD and optionally THC at CBD to THC weight/weight ratio greater than 1, greater than 2, greater than 3, greater than 4 or greater than 5. According to an embodiment said therapeutic effect treats weight gain and/or reduces appetite and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats weight gain and/or reduces appetite and said the primary terpene is selected from the group consisting of eucalyptol, caryophyllene, limonene, humulene, phytol and combinations thereof. According to an embodiment, the product comprises at least 2 of these terpenes, at least 3, at least 4, or at least 5 of the terpenes. According to an embodiment, the primary terpene is selected from the group consisting of eucalyptol, limonene, humulene and combinations thereof. According to various embodiments said primary terpene comprises caryophyllene, eucalyptol, limonene, humulene and/or phytol. According to an embodiment said therapeutic effect treats weight gain and/or reduces appetite and said product comprises a herbal extract selected from the group consisting of extracts of *Ephedra sinica, Foeniculum vulgare, Fucus vesiculosus, Garcinia cambogia, Gymnema sylvestre, Laminaria* spp, *Paullinia cupana* and combinations thereof.

According to an embodiment said therapeutic effect treats digestive problems, intestinal disorders, gastrointestinal pain, abdominal pain (colic), pelvic pain, constipation and/or diarrhea and said administered product comprises at least one of CBD, THC, CBC, CBG, CBN, CBL, THCV and CBDV. According to an embodiment said therapeutic effect treats digestive problem, intestinal disorder, gastrointestinal pain, abdominal pain (colic), pelvic pain, constipation and/or diarrhea and said product comprises CBD and optionally THC at CBD to THC weight/weight ratio greater than 1, greater than 2, greater than 3, greater than 4 or greater than 5. According to an embodiment said therapeutic effect treats digestive problem, intestinal disorder, gastrointestinal pain, abdominal pain (colic), pelvic pain, constipation and/or diarrhea and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats digestive problem, intestinal disorder, gastrointestinal pain, abdominal pain (colic), pelvic pain, constipation and/or diarrhea and said the primary terpene is selected from the group consisting of limonene, cymene, ocimene, terpinene, caryophyllene, citronellol, sabinene, linalool, pinene, myrcene, germacrene, geraniol, nerolidol, menthol, humulene, fenchol, borneol and combinations thereof. According to an embodiment, the product comprises at least 2 of these terpenes, at least 3, at least 4, or at least 5 of the terpenes. According to an embodiment, the primary terpene is selected from the group consisting of limonene, sabinene, caryophyllene and combinations thereof. According to an embodiment, the primary terpene is selected from the group consisting of limonene, sabinene, caryophyllene, citronellol, linalool, myrcene, nerolidol and combinations thereof According to various embodiments said primary terpene comprises limonene, cymene, ocimene, terpinene, caryophyllene, citronellol, sabinene, linalool, pinene, myrcene, germacrene, geraniol, nerolidol, menthol, humulene, fenchol and/or borneol. According to an embodiment, said therapeutic effect treats digestive problem, intestinal disorder, gastrointestinal pain, abdominal pain (colic), pelvic pain, constipation and/or diarrhea and the product further comprises piperine. According to an embodiment said therapeutic effect treats digestive problems, intestinal disorders, gastrointestinal pain, abdominal pain (colic), pelvic pain, constipation and/or diarrhea and said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis* and combinations thereof. According to an embodiment, the product includes pinene, bisabolol and/or limonene, and pinene, bisabolol and/or limonene forms less than 5% by weight of the total terpene content.

According to an embodiment said therapeutic effect treats lack of appetite, nausea, vomiting and/or anorexia and said administered product comprises at least one of CBD, THC, CBC, CBG, CBN, CBL, THCV and CBDV. According to an embodiment said therapeutic effect treats lack of appetite, nausea, vomiting and/or anorexia and said product comprises CBD and optionally THC at CBD to THC weight/weight ratio greater than 1, greater than 2, greater than 3, greater than 4 or greater than 5. According to an embodiment said therapeutic effect treats lack of appetite, nausea, vomiting and/or anorexia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats lack of appetite, nausea, vomiting and/or anorexia and said the primary terpene is selected from the group consisting of linalool, citronellol, geraniol, menthol, humulene, bisabolol, borneol, fenchol, linalool, limonene, terpineol, pinene, caryophyllene, myrcene, cymene, terpinene and combinations thereof. According to an embodiment, the product comprises at least 2 of these terpenes, at least 3, at least 4, or at least 5 of the terpenes. According to an embodiment, the primary terpene is selected from the group consisting of citronellol, linalool caryophyllene and combinations thereof. According to an embodiment, the primary terpene is selected from the group consisting of citronellol, linalool caryophyllene, limonene, myrcene, nerolidol and combinations thereof According to various embodiments said primary terpene comprises linalool, citronellol, geraniol, menthol, humulene, bisabolol, borneol, fenchol, linalool, limonene, terpineol, pinene, caryophyllene, myrcene, cymene and/or terpinene. According to an embodiment, the product includes pinene. borneol, fenchol, terpinene and/or terpineol, and pinene, bisabolol and/or limonene forms less than 5% by weight of the total terpene content.

According to an embodiment said therapeutic effect treats joint pain, joint stiffness, arthralgia, arthritis and/or osteoarthritis and said administered product comprises at least one of CBD, THC, CBC, CBG, CBN, CBL, THCV and CBDV. According to an embodiment said therapeutic effect treats joint pain, joint stiffness, arthralgia, arthritis and/or osteoarthritis and said product comprises CBD and optionally THC at CBD to THC weight/weight ratio greater than 1, greater than 2, greater than 3, greater than 4 or greater than 5. According to an embodiment said therapeutic effect treats joint pain, joint stiffness, arthralgia, arthritis and/or osteoarthritis and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats a joint pain, joint stiffness, arthralgia, arthritis and/or osteoarthritis and said the primary terpene is selected from the group consisting of myrcene, linalool, caryophyllene, eucalyptol, pinene, nerolidol, sabinene, limonene, terpinene, menth-2-en-1-ol, terpineol, geraniol, guaiol, humulene, bisabolol, borneol, fenchol and combinations thereof. According to an embodiment, the product comprises at least 2 of these terpenes, at least 3, at least 4, or at least 5 of the terpenes. According to an embodiment, the primary terpene is selected from the group consisting of myrcene, pinene, sabinene and combinations thereof. According to an embodiment, the primary terpene is selected from the group consisting of myrcene, pinene, sabinene linalool, caryophyllene, limonene and combinations thereof. According to various embodiments said primary terpene comprises myrcene, linalool, caryophyllene, eucalyptol, pinene, nerolidol, sabinene, limonene, terpinene, menth-2-en-1-ol, geraniol, guaiol, humulene, bisabolol, borneol, fenchol 1 and/or terpineol. According to an embodiment, said therapeutic effect treats joint pain, joint stiffness, arthralgia, arthritis and/or osteoarthritis and the product comprises a compound selected from the group consisting of linalyl acetate, geranyl acetate, eugenol, methylis-oeugenol, menthol, eugenyl acetate, piperine and combinations thereof. According to an embodiment said therapeutic effect treats joint pain, joint stiffness, arthralgia, arthritis and/or osteoarthritis and said product comprises a herbal extract selected from the group consisting of extracts of *Boswellia* spp, *Capsicum* spp, *Corydalis yanhusuo, Harpagophytum procumbens, Piscidia erythrina, Salix alba, Zingiber officinalis* and combinations thereof. According to an embodiment, the product optionally includes humulene, pinene, bisabolol, borneol, fenchol, guaiol, linalool, ocimene, terpineol, terpinene and/or caryophyllene, and humulene, pinene, bisabolol, borneol, fenchol, guaiol, linalool, ocimene, terpineol, terpinene and/or caryophyllene forms less than 5% by weight of the total terpene content.

According to an embodiment said therapeutic effect treats hot flashes, night sweat, palpitation, irritability and/or restlessness and said administered product comprises at least one of CBD, THC, CBC, CBG, CBN, CBL, THCV and CBDV. According to an embodiment said therapeutic effect treats hot flashes, night sweat, palpitation, irritability and/or restlessness and said product comprises CBD and optionally THC at CBD to THC weight/weight ratio greater than 1, greater than 2, greater than 3, greater than 4 or greater than 5. According to an embodiment said therapeutic effect treats hot flashes, night sweat, palpitation, irritability and/or restlessness and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats hot flashes, night sweat, palpitation, irritability and/or restlessness and said the primary terpene is selected from the group consisting of caryophyllene, myrcene, humulene, pinene, linalool, limonene, nerolidol, terpinene, terpineol, geraniol, carene, citronellol, eucalyptol, sabinene, myrtenol, bisabolol, borneol, fenchol and combinations thereof. According to an embodiment, the product comprises at least 2 of these terpenes, at least 3, at least 4, or at least 5 of the terpenes. According to an embodiment, the primary terpene is selected from the group consisting of linalool, limonene, eucalyptol and combinations thereof. According to an embodiment, the primary terpene is selected from the group consisting of linalool, limonene, terpineol, geraniol, citronellol, eucalyptol and combinations thereof. According to various embodiments said primary terpene comprises caryophyllene, myrcene, humulene, pinene, linalool, limonene, nerolidol, terpinene, terpineol, geraniol, carene, citronellol, eucalyptol, sabinene, myrtenol, bisabolol, borneol and/or fenchol. According to an embodiment, said therapeutic effect treats hot flashes, night sweat, palpitation, irritability and/or restlessness and the product further comprises a compound selected from the group consisting of linalyl acetate, geranyl acetate, citronellyl formate and combinations thereof. According to an embodiment said therapeutic effect treats hot flashes, night sweat, palpitation, irritability and/or restlessness and said product comprises a herbal extract selected from the group consisting of extracts of *Angelica sinensis, Anemarrhenae asphodeloides, Cimicifuga (actaea) racemosa, Dioscorea villosa, Salvia officinalis, Salvia officinalis, Rehmania glutinosa preparata* and combinations thereof. According to an embodiment, the product optionally includes pinene, bisabolol and/or terpineol, and pinene, bisabolol and/or terpineol forms less than 5% by weight of the total terpene content.

According to an embodiment said therapeutic effect treats inflammation, oxidative stress and/or paresthesia and said administered product comprises at least one of CBD, THC, CBC, CBG, CBN, CBL, THCV and CBDV. According to an embodiment said therapeutic effect treats inflammation, oxidative stress and/or paresthesia and said product comprises CBD and optionally THC at CBD to THC weight/weight ratio greater than 1, greater than 2, greater than 3, greater than 4 or greater than 5. According to an embodiment said therapeutic effect treats inflammation, oxidative stress and/or paresthesia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats inflammation, oxidative stress and/or paresthesia and said the primary terpene is selected from the group consisting of caryophyllene, pinene, myrcene, limonene, humulene, citronellol, eucalyptol, linalool, beta amyrin, cycloartenol, terpinene, terpineol, geraniol, carvacrol, thymol, cardinol, terpinene, menth-2-en-1-ol, carotol, humulene, nerolidol and combinations thereof. According to an embodiment, the product comprises at least 2 of these terpenes, at least 3, at least 4, or at least 5 of the terpenes. According to an embodiment, the primary terpene is selected from the group consisting of myrcene, limonene, thymol and combinations thereof. According to an embodiment, the primary terpene is selected from the group consisting of caryophyllene, pinene, linalool, humulene, myrcene, limonene, thymol and combinations thereof. According to various embodiments said primary terpene comprises caryophyllene, pinene, myrcene, limonene, humulene, citronellol, eucalyptol, linalool, beta amyrin, cycloartenol, terpinene, terpineol, geraniol, carvacrol, thymol, cardinol, terpinene, menth-2-en-1-ol, carotol, humulene, n and/or nerolidol. According to an embodiment, said therapeutic effect treats inflammation, oxidative stress and/or paresthesia and the product further comprises a compound selected from the group consisting of linalyl acetate, geranyl acetate, eugenol, eugenyl acetate, piperine and combinations thereof. According to an embodiment, the product optionally includes fenchol and/or borneol, and fenchol and/or borneol forms less than 5% by weight of the total terpene content.

According to an embodiment said therapeutic effect treats cardiovascular disease, palpitation and tachycardia and said administered product comprises at least one of CBD, THC, CBC, CBG, CBN, CBL, THCV and CBDV. According to an embodiment said therapeutic effect treats cardiovascular disease, palpitation and tachycardia and said product comprises CBD and optionally THC at CBD to THC weight/weight ratio greater than 1, greater than 2, greater than 3, greater than 4 or greater than 5. According to an embodiment said therapeutic effect treats cardiovascular disease, palpitation and tachycardia and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats cardiovascular disease, palpitation and tachycardia and said the primary terpene is selected from the group consisting of linalool, camphene, limonene, pinene, borneol and combinations thereof. According to an embodiment, the product comprises at least 2 of these terpenes, at least 3, at least 4, or all 5 of the terpenes. According to an embodiment, the primary terpene is selected from the group consisting of camphene, limonene, pinene and combinations thereof. According to various embodiments said primary terpene comprises linalool, camphene, limonene, pinene and/or borneol. According to an embodiment said therapeutic effect treats cardiovascular disease, palpitation and tachycardia and said product comprises a herbal extract selected from the group consisting of extracts of *Cimicifuga* (*actaea*) *racemosa*, *Crataegus* spp, *Leonurus* spp, *Passiflora incarnata* and combinations thereof.

According to an embodiment, the enhanced therapeutic effect comprises reducing side effects associated with *cannabis* consumption. According to an embodiment, the primary terpene comprises geraniol, and the side effect comprises hypoglycemia and/or reduction of glucose level. According to an embodiment, the primary terpene is selected from the group consisting of pinene, terpinene, linalool, eucalyptol, myrcene, terpineol, limonene, caryophyllene, borneol and combinations thereof, and the side effect comprises fatigue, weakness, dizziness and/or deficits in balance. According to an embodiment, the primary terpene is selected from the group consisting of camphene, limonene, pinene, borneol and combinations thereof, and the side effect comprises palpitation and/or tachycardia. According to an embodiment, the primary terpene is selected from the group consisting of linalool, citronellol, geraniol, menthol, humulene, bisabolol, borneol, fenchol, linalool, limonene, terpineol, pinene, caryophyllene, myrcene, cymene, terpinene and combinations thereof, and the side effect comprises digestive disorders including vomiting and/or diarrhea. According to an embodiment, the primary terpene is selected from the group consisting myrcene, linalool, caryophyllene, eucalyptol, limonene, nerolidol, fenchol, humulene, guaiol, borneol, bisabolol and combinations thereof, and the side effect comprises headache. According to an embodiment, the primary terpene is selected from the group consisting of pinene, eucalyptol, limonene and combinations thereof, and the side effect comprises coughing. According to an embodiment, the primary terpene is selected from the group consisting of linalool, terpineol, geraniol, thujone, camphor, viridiflorol, borneol, champhene, pinene, eucalyptol, caryophyllene, germacrene, pinene, carene, cirtonellol, nerol, farnesol, limonene, myrcene, terpinene, menth-2-en-1-ol, carotol, sabinene, neral, geranial and combinations thereof, and the side effect comprises impaired fertility. According to an embodiment, the primary terpene is selected from the group consisting of eucalyptol, caryophyllene, limonene, humulene, phytol and combinations thereof, and the side effect comprises increased appetite. According to an embodiment, the primary terpene is selected from the group consisting of pinene, pulegone, eucalyptol, terpineol, cymene, ocimene, limonene, linalool, caryophyllene, humulene, carene and combinations thereof, and the side effect comprises impaired memory, impaired concentration and/or impaired perception. According to an embodiment, the primary terpene is selected from the group consisting of limonene, linalool, caryophyllene, eucalyptol, pinene, myrcene, terpinene, nerolidol, terpineol, geraniol, menthol, citronellol, neral, geraniol, menthol, borneol, phellandrene, bisabolol, fenchol, humulene and combinations thereof, and the side effect comprises anxiety and/or psychotic-like effects.

According to an embodiment, terpene-enriched cannabinoid product is produced by adding isolated terpenes to a *cannabis* extract t.

According to an embodiment, the method for treating a patient comprises (i) administering to the patient for a first period of time a first terpene-enriched *cannabis* product comprising a first cannabinoid at a first cannabinoid amount and a first primary terpene at a first primary terpene amount, followed by (ii) administering to the patient for a second period of time a second terpene-enriched *cannabis* product comprising the first cannabinoid amount and a second primary terpenes at a second primary terpene amount. According to an embodiment, the method further comprises administering to the patient for a third period of time the first terpene-enriched *cannabis* product comprising the first cannabinoid amount and a third primary terpene at a third primary terpene amount. According to an embodiment, the third primary terpene is identical to the first primary terpene.

According to an embodiment, the method for treating a patient comprises administering to said subject for a first period of time a first said product comprising a first cannabinoid at a first cannabinoid amount and a first primary terpene at a first primary terpene amount, followed by (i) administering to said subject for a second period of time said product comprising said first cannabinoid at said first cannabinoid amount or less and a second primary terpene at a second primary terpene amount; (ii) administering to said subject for a second period of time said product comprising said first cannabinoid at said first cannabinoid amount or less and a first primary terpene at an increased first primary terpene amount; (iii) administering to said subject for a second period of time said product comprising said first cannabinoid at a said first cannabinoid amount or less, first primary terpene at a first primary terpene amount and at least one secondary terpene; and/or (iv) administering to said subject for a second period of time said product comprising said first cannabinoid at a said first cannabinoid amount or less, first primary terpene at a first primary terpene amount and a second primary terpene.

According to another embodiment, the method for treating a patient comprises (i) administering to the patient a first terpene-enriched *cannabis* product comprising a first cannabinoid at a first cannabinoid amount and a first primary terpene at a first primary terpene amount and administering to the patient, at least 2 hours later a second terpene-enriched *cannabis* product comprising the first cannabinoid amount and a second primary terpenes at a second primary terpene amount. According to another embodiment, the first terpene-enriched *cannabis* product is administered for day time and the second terpene-enriched *cannabis* product is administered for night time.

According to another embodiment, the method for treating a patient comprises administering to the patient (i) a first terpene-enriched *cannabis* product comprising a first cannabinoid at a first cannabinoid amount and a first primary terpene at a first primary terpene amount and (ii) a second terpene-enriched *cannabis* product comprising the first cannabinoid and a second primary terpenes at a second primary terpene amount.

According to an embodiment, the method for treating a patient comprises (i) administering to the patient multiple *cannabis* products to find the best working one; (ii) mimicking the best working product by extracting *cannabis* plant material to form an extract and blending the extract with suitable terpenes, whereby a mimicking product is formed and (iii) administering to the patient the mimicking product. According to an embodiment, the method further comprises removing terpenes from the extract prior to the blending.

According to an embodiment, the method for treating a patient comprises administering to said patient a product selected from the group consisting of tablets, gel capsules, medical patches, topicals, creams, varnishes, sublingual oils, sprays, edibles, beverages, suppositories including tampons and/or rectal candles, cigarettes, vaporizer liquids, micro and nano-emulsions, preparations containing micro and nano-particle and combinations thereof, containing the administered product. According to an embodiment, the product comprising tablets containing the product. According to an embodiment, the product comprising gel capsules containing the product. According to an embodiment, the product comprising medical patches containing the product. According to an embodiment, the product comprising topicals containing the product. According to an embodiment, the product comprising creams containing the product. According to an embodiment, the product comprising varnishes containing the product. According to an embodiment, the product comprising sublingual oils containing the product. According to an embodiment, the product comprising edibles containing the product. According to an embodiment, the product comprising beverages containing the product. According to an embodiment, the product comprising tampons containing the product. According to an embodiment, the product comprising rectal candles containing the product. According to an embodiment, the product comprising cigarettes containing the product. According to an embodiment, the product comprising vaporizer liquids containing the product.

According to an embodiment, further provided is a treatment method comprising administering to a subject in need a therapeutically effective amount of a product comprising (i) a primary terpene in a specific amount; (ii) optionally at least three secondary terpenes; (iii) optionally at least one cannabinoid in a specific amount; having an enhanced therapeutic effect compared with administrating a product comprising one half the amount of said primary terpene. According to an embodiment the products comprises at least 5% by weight of a non-cannabinoid, non-terpene, carrier. According to an embodiment the administrated product has an enhanced therapeutic effect in treating and/or healing and/or relieving and/or decreasing, preventing and/or reducing the risk associated with, and/or improving the quality of life associated with conditions and/or symptoms associated with at least one of arthritis, osteoarthritis, arthralgia, joint pain, joint stiffness, diabetes, lack of appetite, anorexia, vomiting, nausea, an inflammatory bowel disease including Crohn's disease and ulcerative colitis, dementia, memory loss, osteoporosis, fatigue, weakness, decreased mental energy, decreased physical energy, dizziness, deficits in balance, itchy skin, pruritus and/or chronic pruritus, wrinkles, stretch marks, skin burn, headache, migraine, weight gain, digestive problem, intestinal disorder, gastro-intestinal pain, abdominal pain, pelvic pain, constipation, diarrhea, hot flashes, sweating, difficulty in concentration, weakened immune system, cardiovascular disease, palpitation and tachycardia, psoriasis, dermatophytes, *Candida*, leishmaniasis, Methycillin-resistant *Staphylococcus aureus* (MRSA), malaria, allergy, fibromyalgia, nociceptive pain, neuropathic pain, pain, arm or leg pain, acne, insomnia and/or sleep disorders, muscle pain, myalgia, spasticity, muscle tension, cramps, spasms, anxiety, irritability, nervousness, restless, stress, depression, mood problem, affect disorders, anger, autism and/or autism spectrum disorder, neurodegenerative diseases, Alzheimer disease, Parkinson disease, Huntington's disease, Dystonia, Amyotrophic Lateral Sclerosis (ALS), multiple sclerosis, Tourette syndrome, Myasthenia Gravis, epilepsy, cancer, inflammatory airway diseases including asthma and/or chronic obstructive pulmonary disease (COPD), addiction, stroke, traumatic brain injury, motor spasm and/or tic, vocal tic, obsessive compulsive disorder (OCD), attention deficit hyperactivity disorder (ADHD), attention deficit disorder (ADD), cerebral palsy (CP), inflammation, oxidative stress, paresthesia, glaucoma and combinations thereof. According to an embodiment, the conditions and/or symptoms are associated with aging. According to an embodiment, the composition comprises less than 20% by weight water.

According to an embodiment, the administered composition additionally contains an additive selected from the group consisting of antioxidants, emulsifiers and texturizers vegetable oils, plant extracts, honey, sucrose, glucose and fructose, pharmaceutical excipients and combinations thereof.

According to an embodiment, the primary terpene is selected from the group consisting of pinene, limonene, linalool, caryophyllene, caryophyllene oxide, myrcene, humulene, borneol, eucalyptol, terpineol, nerolidol, phytol, geraniol, bisabolol, camphene, amyrin, thujone, citronellol, pulegone, cycloartenol, cymene, sabinene, carene, terpinene, fenchol, isopulegol, guaiol, phellandrene, eudesmol, ocimene, cardinol, elemene, friedelin, carvacrol, eugenol, camphor, menthol, iso-menthone, neral, gerial, viridiflorol, germacrene, thymol, Menth-2-en-1-ol, farensol, carotol, myrtenol and combinations thereof. According to an embodiment, the administered product comprises a primary terpene and optionally at least one secondary terpenes, at least two, at least three secondary terpenes, at least four, or at least five secondary terpenes. As used here, the term "primary terpene" refers to a terpene that forms at least 20% by weight of the total amount of terpenes in the product, at least 25%, at least 30%, at least 35%, at least 40%, at least 50%, at least 60%, at least 70% or at least 80%. As used here, the term "primary terpene" refers to a terpene having the greatest amount in the composition. As used here, the term "primary terpene" refers to a terpene that forms the highest terpene concentration in the composition. According to an embodiment, the product comprises multiple (e.g. two, three, or four) According to an embodiment, the primary terpene forms at least 20% by weight of the total terpene content, at least 30%, at least 40%, at least 50%, at least 60%, at least 70% or at least 80%, at least 90% by weight of the total terpene content. According to an embodiment, the product comprises multiple (e.g. two or three) terpenes, each one of which forms at least 20% by weight of the total amount of terpenes in the product and each one of these terpenes is considered a primary terpene. According to an embodiment, the product comprises multiple (e.g. two, three, or four) terpenes, each one of which forms at least 15% by weight of the total amount of terpenes in the product, at least 18%, at least 22%, at least 25%, at least 300%, at least 35%, or at least 40%, and each one of these terpenes is considered a primary terpene. As used here, the term "secondary terpene" refers to a terpene that forms at least 10 parts per million (ppm) of the product. According to an embodiment, the content of the primary terpene in the product is at least 1.3 times greater than that of any secondary terpene, at least 1.5, at least 2, at least 2.2, at least 2.5, at least 3, at least 3.5, at least 4, at least 6, at least 8, at least 10, at least 15, at least 20, at least 25, or at least 30 times greater. According to a related embodiment, the administered product comprises chlorophyll. According to an embodiment, the product comprises at least 0.5% by weight chlorophyll, at least 1%, at least 5%, at least 10%, at least 15%, at least 20% chlorophyll. According to an embodiment, the administered product comprises at least one flavonoid. According to an embodiment, the product comprises at least two, at least three, at least four, or at least five flavonoids. According to an embodiment, the product comprises at least one of bergamottin, apigenin, amentoflavone, quercetin and piperine. According to an embodiment, the product comprises at least two, at least three, or at least four of bergamottin, apigenin, amentoflavone, quercetin and piperine. According to an embodiment, the product comprises bergamottin. According to an embodiment, the product comprises apigenin. According to an embodiment, the product comprises amentoflavone. According to an embodiment, the product comprises quercetin. According to an embodiment, the product comprises piperine.

According to an embodiment, the product has an enhanced therapeutic effect in treating conditions and/or symptoms associated with aging. According to a related embodiment, the primary terpene is selected from the group consisting of caryophyllene, linalool, pinene, eucalyptol, sabinene, terpineol and combinations thereof. According to an embodiment, the composition comprises at least 2 of the terpenes, at least 3, at least 4 or at least 5 of the terpenes. According to an embodiment, the primary terpene is selected from the group consisting of caryophyllene, linalool, pinene, terpineol and combinations thereof. According to an embodiment, the primary terpene is selected from the group consisting of caryophyllene, linalool, sabinene and combinations thereof.

According to an embodiment, the enhanced therapeutic effect applies to a child. As used herein the term "therapeutic effect applies to a child" refers to therapeutic effect observed when the treated patient is a child.

According to an embodiment, the product has an enhanced therapeutic effect in treating a child. According to a related embodiment, the primary terpene is selected from the group consisting of caryophyllene, limonene, pinene, terpineol and combinations thereof. According to an embodiment, the composition comprises at least 2 of the terpenes, at least 3, or all 4 of the terpenes. According to an embodiment, the primary terpene is selected from the group consisting of caryophyllene, limonene and combination thereof.

According to an embodiment, the conditions and/or symptoms are observed in a child.

According to an embodiment, the composition comprises at least 5% by weight carrier, at least 10%, at least 15%, at least 20%, at least 25%, at least 30%, at least 35% or at least 40% by weight. Any compound other than cannabinoids and terpenes is a suitable carrier. According to an embodiment, the carrier is selected from the group consisting of vegetable oils, e.g. coconut oil, olive oil or sesame oil, pharmaceutical excipients, honey, bees wax, cellulose and combinations thereof. According to an embodiment, the carrier is an essential oil. According to an embodiment, the carrier is an herbal extract.

According to an embodiment, said enhanced therapeutic effect comprises shorter onset time of the therapeutic effect. According to an embodiment, the primary terpene, and optionally cannabinoids and secondary terpenes are present in specific amounts, and the onset time of the therapeutic effect, as measured by methods known in the art, is at least 20% shorter than that of a product comprising the same amounts of cannabinoids and secondary terpenes and one half the amount of the primary terpene, at least 30%, at least 40%, at least 50%, at least 60%, or at least 70% shorter. Shorter onset time, or differently put an earlier effect, is important particularly in cases of sublingual, edible and topical delivery and in cases where a rapid effect is desired, as in treating pain.

According to an embodiment, said enhanced therapeutic effect comprises longer onset time of the therapeutic effect. According to an embodiment, the primary terpene, and optionally cannabinoids and secondary terpenes are present in specific amounts, and the onset time of the therapeutic effect, as measured by methods known in the art, is at least 20% longer than that of a product comprising the same amounts of cannabinoids and secondary terpenes and one half the amount of the primary terpene, at least 30%, at least 40%, at least 50%, at least 60%, or at least 70% longer. According to an embodiment, products of delayed onset time are used in combination with shorter onset time to reach a sustained release effect.

According to an embodiment, said enhanced therapeutic effect comprises greater and/or increased magnitude of the therapeutic effect. According to an embodiment, the primary terpene, and optionally cannabinoids and secondary terpenes are present in specific amounts, and the magnitude of the therapeutic effect, as measured by methods known in the art, is at least 20% greater compared with that of a product comprising the same amounts of cannabinoids and secondary terpenes and one half the amount of the primary terpene, at least 30%, at least 40%, at least 50%, at least 60%, or at least 70% greater. Without wishing to be limited by any particular theory, such increased magnitude of the therapeutic effect may indicate increased bioavailability. Such increased magnitude enables achieving a desired therapeutic effect on administering smaller doses of cannabinoids, saving thereby on cost.

According to an embodiment, said enhanced therapeutic effect comprises longer and/or extended duration of the therapeutic effect. According to an embodiment, the primary terpene, and optionally cannabinoids and secondary terpenes are present in specific amounts, and the duration of the therapeutic effect, as measured by methods known in the art, is at least 20% longer compared with that of a product comprising the same amounts of cannabinoids and secondary terpenes and one half the amount of the primary terpene, at least 30%, at least 40%, at least 50%, at least 60%, at least 70%, at least 80%, at least 90% or at least 100% longer.

According to an embodiment, said enhanced therapeutic effect comprises smaller therapeutically effective amount of a product and/or reduced dosages of the product. According to an embodiment, the primary terpene, and optionally cannabinoids and secondary terpenes are present in specific amounts, and the therapeutically effective amount of the product, as measured by methods known in the art, is at least 20% smaller compared with that of a product comprising the same amounts of cannabinoids and secondary terpenes and one half the amount of the primary terpene, at least 30%, at least 40%, at least 50%, at least 60%, at least 70%, at least 80%, at least 90% or at least 100% smaller.

According to an embodiment, said enhanced therapeutic effect comprises reduced secondary adverse symptoms. According to an embodiment, the primary terpene, and optionally cannabinoids and secondary terpenes are present in specific amounts, and the secondary adverse symptoms, as measured by methods known in the art, are reduced by at least 20% compared with that of a product comprising the same amounts of cannabinoids and secondary terpenes and one half the amount of the primary terpene, by at least 30%, at least 40%, at least 50%, at least 60%, at least 70%, at least 80%, at least 90% or at least 100%.

According to an embodiment, said enhanced therapeutic effect comprises smaller and/or reduced frequency of conditions and/or symptoms. According to an embodiment, the primary terpene, and optionally cannabinoids and secondary terpenes are present in specific amounts, and the frequency of the conditions and/or symptoms, as measured by methods known in the art, is at least 20% smaller compared with that of a product comprising the same amounts of cannabinoids and secondary terpenes and one half the amount of the primary terpene, at least 30%, at least 40%, at least 50% at least 60%, at least 70%, at least 80%, or at least 90% smaller. According to an embodiment, said enhanced therapeutic effect comprises smaller and/or reduced severity of conditions and/or symptoms. According to an embodiment, the primary terpene, the cannabinoids and optionally secondary terpenes are present in specific amounts, and the severity of the conditions and/or symptoms, as measured by methods known in the art, is at least 20% smaller compared with that of a product comprising the same amounts of cannabinoids and secondary terpenes and one half the amount of the primary terpene, at least 30%, at least 40%, at least 50% at least 60%, at least 70%, at least 80%, or at least 90% smaller.

According to an embodiment, said enhanced therapeutic effect comprises smaller and/or reduced consumption of other drugs. According to an embodiment, the primary terpene, and optionally cannabinoids and secondary terpenes are present in specific amounts, and the consumption of other drugs is reduced by at least 20% compared with that of a product comprising the same amounts of cannabinoids and secondary terpenes and one half the amount of said primary terpene, reduced by at least 30%, by at least 40%, by at least 50%, by at least 60%, by at least 70%, by at least 80%, or by at least 90%.

According to an embodiment said therapeutic effect treats diabetes and said primary terpene is selected from the group consisting of limonene, pinene, linalool, humulene, myrcene, phytol, geraniol, bisabolol, borneol, guaiol, ocimene, fenchol, terpineol, terpinene, eucalyptol and combinations thereof. According to an embodiment, the product comprises at least 2 of these terpenes, at least 3, at least 4, or at least 5 of the terpenes. According to an embodiment, the primary terpene is selected from the group consisting of limonene, linalool, geraniol and combinations thereof. According to an embodiment, the primary terpene is selected from the group consisting of limonene, linalool, geraniol, pinene, humulene, phytol and combinations thereof. According to various embodiments said primary terpene comprises limonene, pinene, linalool, humulene, myrcene, phytol, geraniol, bisabolol, borneol, guaiol, ocimene, fenchol, terpineol, terpinene and/or eucalyptol.

According to an embodiment said therapeutic effect treats Crohn's disease and ulcerative colitis and said primary terpene is selected from the group consisting of limonene, caryophyllene, borneol, myrcene, pinene, terpinene, isopulegol, phellandrene, carene, carvacol, terpineol, humulene and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, myrcene and combinations thereof. According to an embodiment, the primary terpene is selected from the group consisting of limonene, caryophyllene, myrcene, pinene, carene, carvacol and combinations thereof. According to various embodiments said primary terpene comprises limonene, caryophyllene, borneol, myrcene, pinene, terpinene, isopulegol, phellandrene, carene, carvacol, terpineol and/or humulene. According to an embodiment, said therapeutic effect treats Crohn's disease and ulcerative colitis and the product further comprises a compound selected from the group consisting of linalyl acetate, geranyl acetate, eugenol, eugenyl acetate, piperine and combinations thereof. According to an embodiment, the product includes fenchol and fenchol forms less than 5% by weight of the total terpene content.

According to an embodiment said therapeutic effect stimulates the immune system and/or treats weakened immune system and said primary terpene is selected from the group consisting linalool, pinene, borneol, caryophyllene, geraniol, amyrin, terpinene, myrcene, eucalyptol, humulene and combinations thereof. According to an embodiment, the product comprises at least 2 of these terpenes, at least 3, at least 4, or at least 5 of the terpenes. According to an embodiment, the primary terpene is selected from the group consisting of linalool, caryophyllene, amyrin, and combinations thereof. According to an embodiment, the primary terpene is selected from the group consisting of linalool, caryophyllene, amyrin, pinene, terpinene, myrcene and combinations thereof. According to various embodiments said primary terpene comprises linalool, pinene, borneol, caryophyllene, geraniol, amyrin, terpinene, myrcene, eucalyptol and/or humulene.

According to an embodiment said therapeutic effect treats Fibromyalgia and said primary terpene is selected from the group consisting of linalool, caryophyllene, limonene, humulene, eucalyptol, amyrin, cycloartenol, pinene, sabinene, myrcene, terpinene, borneol, bisabolol and combinations thereof. According to an embodiment, the product comprises at least 2 of these terpenes, at least 3, at least 4, or at least 5 of the terpenes. According to an embodiment, the primary terpene is selected from the group consisting of linalool, caryophyllene, eucalyptol and combinations thereof. According to an embodiment, the primary terpene is selected from the group consisting of linalool, caryophyllene, eucalyptol, limonene, pinene, sabinene, myrcene and combinations thereof. According to various embodiments said primary terpene comprises linalool, caryophyllene, limonene, humulene, eucalyptol, amyrin, cycloartenol, pinene, sabinene, myrcene, terpinene, borneol and/or bisabolol. According to an embodiment, the product includes myrcene, humulene, bisabolol, borneol, limonene and/or linalool and myrcene, humulene, bisabolol, borneol, limonene and/or linalool forms less than 5% by weight of the total terpene content.

According to an embodiment said therapeutic effect treats nociceptive pain and said primary terpene is selected from the group consisting of myrcene, linalool, caryophyllene, eucalyptol, cycloartenol, borneol, sabinene, camphene, terpineol, citronellol, geraniol, humulene, bisabolol, limonene and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, eucalyptol, terpineol, citronellol and combinations thereof. According to various embodiments said primary terpene comprises myrcene, linalool, caryophyllene, eucalyptol, cycloartenol, borneol, sabinene, camphene, terpineol, citronellol, geraniol, humulene, bisabolol and/or limonene.

According to an embodiment said therapeutic effect treats neuropathic pain and said primary terpene is selected from the group consisting of caryophyllene, linalool, eucalyptol, amyrin, borneol, pinene, terpineol, limonene, nerolidol, geraniol, myrcene and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, eucalyptol and combinations thereof. According to an embodiment, the primary terpene is selected from the group consisting of caryophyllene, linalool, eucalyptol, borneol, limonene, myrcene and combinations thereof. According to an embodiment, the primary terpene is selected from the group consisting of pinene, terpineol, nerolidol and combinations thereof. According to various embodiments said primary terpene comprises caryophyllene, linalool, eucalyptol, amyrin, borneol, pinene, terpineol, limonene, nerolidol, geraniol and/or myrcene. According to an embodiment, the product includes humulene, bisabolol, borneol, limonene and/or linalool, and humulene, bisabolol, borneol, limonene and/or linalool forms less than 5% by weight of the total terpene content.

According to an embodiment said therapeutic effect treats pain and said primary terpene is selected from the group consisting of myrcene, linalool, humulene, eucalyptol, caryophyllene, caryophyllene oxide, amyrin, cycloartenol, borneol, sabinene, camphene, nerolidol, terpineol, geraniol, citronellol, camphor, bisabolol, limonene and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, eucalyptol, borneol, terpineol and combinations thereof. According to various embodiments said primary terpene comprises myrcene, linalool, humulene, eucalyptol, caryophyllene, caryophyllene oxide, amyrin, cycloartenol, borneol, sabinene, camphene, nerolidol, terpineol, geraniol, citronellol, camphor, bisabolol and/or limonene. According to an embodiment, said therapeutic effect treats pain and the product comprises a compound selected from the group consisting of linalyl acetate, geranyl acetate, eugenol, eugenyl acetate, piperine, methylis-oeugenol, Methyleugenol, menthol and combination thereof. According to an embodiment, the product includes humulene, bisabolol, borneol, limonene and/or linalool, wherein humulene, bisabolol, borneol, limonene and/or linalool forms less than 5% by weight of the total terpene content. According to an embodiment, said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis* and combinations thereof.

According to an embodiment said therapeutic effect treats arm or leg pain and said primary terpene is selected from the group consisting of linalool, terpinene, pinene, limonene, terpineol, myrcene, nerolidol and combinations thereof. According to an embodiment, the product comprises at least 2 of these terpenes, at least 3, at least 4, or at least 5 of the terpenes. According to an embodiment, the primary terpene is selected from the group consisting of linalool, pinene, myrcene and combinations thereof. According to an embodiment, the primary terpene is selected from the group consisting of linalool, pinene, myrcene, limonene, terpineol, nerolidol and combinations thereof. According to various embodiments said primary terpene comprises linalool, terpinene, pinene, limonene, terpineol, myrcene and/or nerolidol.

According to an embodiment said therapeutic effect treats neurodegenerative diseases including Alzheimer disease, Parkinson disease, Huntington's disease, dystonia and/or Amyotrophic lateral sclerosis (ALS) and said primary terpene is selected from the group consisting of terpineol, carvophyllene, myrcene, terpineol, linalool, humulene, eucalyptol, pinene, pulegone, cymene, ocimene, limonene, nerolidol, sabinene, carene, citronellol, geraniol, menthol, borneol, terpinene, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, pinene, terpineol and combinations thereof. According to an embodiment, the primary terpene is selected from the group consisting of caryophyllene, linalool, pinene, terpineol, myrcene, terpineol, limonene, nerolidol, sabinene and combinations thereof. According to various embodiments said primary terpene comprises terpineol, caryophyllene, myrcene, terpineol, linalool, humulene, eucalyptol, pinene, pulegone, cymene, ocimene, limonene, nerolidol, sabinene, carene, citronellol, geraniol, menthol, borneol, terpinene, bisabolol and/or fenchol. According to an embodiment said therapeutic effect treats Alzheimer disease and said the primary terpene is selected from the group consisting of pinene, eucalyptol, linalool, terpineol, myrcene, caryophyllene and combinations thereof. According to an embodiment said therapeutic effect treats Alzheimer disease and said primary terpene is selected from the group consisting of pinene, eucalyptol, linalool and combinations thereof. According to an embodiment said therapeutic effect treats Parkinson disease, Huntington's disease, dystonia and/or Amyotrophic lateral sclerosis (ALS) and said primary terpene is selected from the group consisting caryophyllene, myrcene, linalool, pinene, limonene, nerolidol, sabinene, terpineol and combinations thereof. According to an embodiment said therapeutic effect treats Parkinson disease, Huntington's disease, dystonia and/or Amyotrophic lateral sclerosis (ALS) and said primary terpene is selected from the group consisting myrcene, linalool, pinene, nerolidol and combinations thereof. According to an embodiment, said therapeutic effect treats neurodegenerative diseases including Alzheimer, Parkinson disease, Huntington's disease, dystonia and/or Amyotrophic lateral sclerosis (ALS) and the product comprises a compound selected from the group consisting of linalyl acetate, geranyl acetate, menthol, piperine, eugenol, citronellyl formate, jasmone, benzy acetate, benzyl alcohol and combination thereof. According to an embodiment, the product includes pinene, myrcene and/or terpineol, and pinene, myrcene and/or terpineol forms less than 5% by weight of the total terpene content.

According to an embodiment said therapeutic effect treats multiple sclerosis and said primary terpene is selected from the group consisting of caryophyllene, pinene, myrcene, limonene, humulene, citronellol, eucalyptol, caryophyllene oxide, linalool, amyrin, cycloartenol, cymene, terpinene, borneol, pulegol, nerolidol, terpineol, sabinene, geraniol and combinations thereof. According to an embodiment, the product comprises at least 2 of these terpenes, at least 3, at least 4, or at least 5 of the terpenes. According to an embodiment, the primary terpene is selected from the group consisting of caryophyllene, myrcene, linalool and combinations thereof. According to an embodiment, the primary terpene is selected from the group consisting of caryophyllene, myrcene, linalool, pinene, limonene, eucalyptol and combinations thereof. According to various embodiments said primary terpene comprises caryophyllene, pinene, myrcene, limonene, humulene, citronellol, eucalyptol, caryophyllene oxide, linalool, amyrin, cycloartenol, cymene, terpinene, borneol, pulegol, nerolidol, terpineol, sabinene and/or geraniol.

According to an embodiment said therapeutic effect treats Myasthenia gravis and said primary terpene is selected from the group consisting of pinene, terpineol, eucalyptol, pulegone, cymene, ocimene, nerolidol, limonene, linalool, citronellol, geraniol, menthol, caryophyllene, borneol and combinations thereof. According to an embodiment, the product comprises at least 2 of these terpenes, at least 3, at least 4, or at least 5 of the terpenes. According to an embodiment, the primary terpene is selected from the group consisting of terpineol, eucalyptol, linalool and combinations thereof. According to an embodiment, the primary terpene is selected from the group consisting of terpineol, eucalyptol, linalool, pinene, nerolidol, limonene and combinations thereof. According to various embodiments said primary terpene comprises pinene, terpineol, eucalyptol, pulegone, cymene, ocimene, nerolidol, limonene, linalool, citronellol, geraniol, menthol, caryophyllene, and/or borneol. According to an embodiment, the product includes myrcene and/or pinene, and myrcene and/or pinene forms less than 5% by weight of the total terpene content.

According to an embodiment said therapeutic effect treats epilepsy and said primary terpene is selected from the group consisting of linalool, terpineol, ocimene, myrcene, limonene, caryophyllene and combinations thereof. According to an embodiment, the product comprises at least 2 of these terpenes, at least 3, at least 4, or at least 5 of the terpenes. According to an embodiment, the primary terpene is selected from the group consisting of linalool, terpineol, ocimene and combinations thereof. According to various embodiments said primary terpene comprises linalool, terpineol, ocimene, myrcene, limonene and/or caryophyllene.

According to an embodiment said therapeutic effect treats cancer and/or cancer related symptom and said primary terpene is selected from the group consisting of myrcene, limonene, caryophyllene, caryophyllene oxide, terpinene, citronellol, linalool, geraniol. Menthol. humulene, amyrin, cycloartenol, pinene, camphene, eucalyptol, terpineol, borneol and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, linalool and combinations thereof. According to an embodiment, the primary terpene is selected from the group consisting of limonene, caryophyllene, linalool, citronellol, myrcene, eucalyptol, pinene and combinations thereof. According to various embodiments said primary terpene comprises myrcene, limonene, caryophyllene, caryophyllene oxide, terpinene, citronellol, linalool, geraniol, menthol, humulene, amyrin, cycloartenol, pinene, camphene, eucalyptol, terpineol and/or borneol. According to an embodiment, said therapeutic effect treats cancer and/or cancer related symptom and the product comprises a compound selected from the group consisting of linalyl acetate, geranyl acetate, eugenol, eugenyl acetate, piperine, methylis-oeugenol, Methyleugenol, menthol and combination thereof.

According to an embodiment said therapeutic effect treats stroke and/or traumatic brain injury and said primary terpene is selected from the group consisting of myrcene, terpinene, caryophyllene, caryophyllene oxide, pinene, limonene, humulene, citronellol, eucalyptol, linalool, amyrin, cycloartenol, terpineol, thymol, eucalyptol, geraniol, carvacrol, thymol, cardinol, menth-2-en-1-ol, carotol and combinations thereof. According to an embodiment, the product comprises at least 2 of these terpenes, at least 3, at least 4, or at least 5 of the terpenes. According to an embodiment, the primary terpene is selected from the group consisting of myrcene, caryophyllene, limonene and combinations thereof. According to an embodiment, the primary terpene is selected from the group consisting of myrcene, caryophyllene, limonene, pinene, humulene, terpineol, thymol, eucalyptol and combinations thereof. According to various embodiments said primary terpene comprises myrcene, terpinene, caryophyllene, caryophyllene oxide, pinene, limonene, humulene, citronellol, eucalyptol, linalool, amyrin, cycloartenol, terpineol, thymol, eucalyptol, geraniol, carvacrol, thymol, cardinol, menth-2-en-1-ol and/or carotol. According to an embodiment, the product includes fenchol and/or borneol, and fenchol and/or borneol forms less than 5% by weight of the total terpene content.

According to an embodiment said therapeutic effect treats addiction, including addiction to drugs, smoking, drinks, food, gambling, sex, and sports and said primary terpene is selected from the group consisting of caryophyllene, pinene, myrcene, limonene, linalool, terpineol and combinations thereof. According to an embodiment, the product comprises at least 2 of these terpenes, at least 3, at least 4, or at least 5 of the terpenes. According to an embodiment, the primary terpene is selected from the group consisting of caryophyllene, linalool, terpineol and combinations thereof. According to various embodiments said primary terpene comprises caryophyllene, pinene, myrcene, limonene, linalool and/or terpineol.

According to an embodiment said therapeutic effect treats inflammatory airway diseases including asthma and/or chronic obstructive pulmonary disease (COPD) and said primary terpene is selected from the group consisting of pinene, eucalyptol, limonene, humulene, camphene, caryophyllene and combinations thereof. According to an embodiment, the product comprises at least 2 of these terpenes, at least 3, at least 4, or at least 5 of the terpenes. According to an embodiment, the primary terpene is selected from the group consisting of pinene, eucalyptol, humulene, and combinations thereof. According to various embodiments said primary terpene comprises pinene, eucalyptol, limonene, humulene, camphene and/or caryophyllene.

According to an embodiment said therapeutic effect treats cerebral palsy (CP) and said primary terpene is selected from the group consisting of myrcene, pinene, linalool, humulene, nerolidol, limonene, terpineol, sabinene and combinations thereof. According to an embodiment, the product comprises at least 2 of these terpenes, at least 3, at least 4, or at least 5 of the terpenes. According to an embodiment, the primary terpene is selected from the group consisting of myrcene, pinene, nerolidol and combinations thereof. According to an embodiment, the primary terpene is selected from the group consisting of linalool, limonene, sabinene and combinations thereof. According to various embodiments said primary terpene comprises myrcene, pinene, linalool, humulene, nerolidol, limonene, terpineol and/or sabinene.

According to an embodiment said therapeutic effect treats autism and/or autism spectrum disorder and said primary terpene is selected from the group consisting of limonene, caryophyllene, pinene, myrcene, humulene, citronellol, eucalyptol, linalool, terpineol, ocimene, geraniol, menthol, borneol, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of pinene, eucalyptol, linalool and combinations thereof. According to an embodiment, the primary terpene is selected from the group consisting of pinene, eucalyptol, linalool, caryophyllene, myrcene, terpineol and combinations thereof. According to various embodiments said primary terpene comprises limonene, caryophyllene, pinene, myrcene, humulene, citronellol, eucalyptol, linalool, terpineol, ocimene, geraniol, menthol, borneol, bisabolol and/or fenchol.

According to an embodiment said therapeutic effect treats hyperactivity disorder (ADHD), attention deficit disorder (ADD) and/or obsessive-compulsive disorder (OCD) and said primary terpene is selected from the group consisting of linalool, eucalyptol, terpineol, myrcene, pinene, pulegone, caryophyllene, geraniol, citronellol, menthol, caryophyllene, pinene, borneol, bisabolol, fenchol and combinations thereof. According to an embodiment, the product comprises at least 2 of these terpenes, at least 3, at least 4, or at least 5 of the terpenes. According to an embodiment said therapeutic effect treats hyperactivity disorder (ADHD) and/or attention deficit disorder (ADD) and said primary terpene is selected from the group consisting of linalool, eucalyptol, myrcene, and combinations thereof. According to an embodiment, the primary terpene is selected from the group consisting of linalool, eucalyptol, myrcene, caryophyllene, pinene, borneol and combinations thereof. According to an embodiment said therapeutic effect treats obsessive-compulsive disorder (OCD) and said primary terpene is selected from the group consisting of limonene, eucalyptol, pinene and combination thereof. According to an embodiment, the primary terpene is selected from the group consisting of linalool, caryophyllene, borneol and combination thereof. According to various embodiments said primary terpene comprises linalool, eucalyptol, terpineol, myrcene, pinene, pulegone, caryophyllene, geraniol, citronellol, menthol, caryophyllene, pinene, borneol, bisabolol and/or fenchol.

According to an embodiment said therapeutic effect treats Tourette syndrome, motor spasms, motor tics and/or vocal tics and said primary terpene is selected from the group consisting of myrcene, linalool, limonene, pinene, nerolidol, caryophyllene, eucalyptol, geraniol, menthol, borneol, bisabolol, fenchol and combinations thereof. According to an embodiment, the product comprises at least 2 of these terpenes, at least 3, at least 4, or at least 5 of the terpenes. According to an embodiment, the primary terpene is selected from the group consisting of myrcene, limonene, nerolidol and combinations thereof. According to an embodiment, the primary terpene is selected from the group consisting of linalool, pinene, eucalyptol and combinations thereof. According to various embodiments said primary terpene comprises myrcene, linalool, limonene, pinene, nerolidol, caryophyllene, eucalyptol, geraniol, menthol, borneol, bisabolol and/or fenchol.

According to an embodiment said therapeutic effect treats psoriasis and said primary terpene is selected from the group consisting of linalool, caryophyllene, limonene and combinations thereof. According to an embodiment, the product comprises at least 2 of these terpenes or all 3 of the terpenes. According to an embodiment, the primary terpene is selected from the group consisting of linalool, caryophyllene, limonene and combinations thereof. According to various embodiments said primary terpene comprises linalool, caryophyllene and/or limonene.

According to an embodiment said therapeutic effect treats dermatophytes and said primary terpene is selected from the group consisting of limonene, caryophyllene, caryophyllene oxide, nerolidol, eucalyptol, terpinene, cycloartenol, amyrin, campene and combinations thereof. According to an embodiment, the product comprises at least 2 of these terpenes, at least 3, at least 4, or at least 5 of the terpenes. According to an embodiment, the primary terpene is selected from the group consisting of limonene, caryophyllene, caryophyllene oxide and combinations thereof. According to an embodiment, the primary terpene is selected from the group consisting of limonene, caryophyllene, caryophyllene oxide, nerolidol, eucalyptol, terpinene and combinations thereof. According to various embodiments said primary terpene comprises limonene, caryophyllene, caryophyllene oxide, nerolidol, eucalyptol, terpinene, cycloartenol, amyrin and/or campene.

According to an embodiment said therapeutic effect treats *candida* infection and said primary terpene is selected from the group consisting of pinene, limonene, caryophyllene, caryophyllene oxide, nerolidol, eucalyptol, terpinene, terpineol, myrcene, cycloartenol, citronellol, amyrin, camphene, cymene, Ocimene, humulene, farnesene, guaiol, eudesmol, friedelin, linalool, camphor, menthol, thymol, carvacrol, eugenol, farnesol, citronellol, geraniol, citral, ionone and combinations thereof. According to an embodiment, the product comprises at least 2 of these terpenes, at least 3, at least 4, or at least 5 of the terpenes. According to an embodiment, the primary terpene is selected from the group consisting of thymol, carvacrol, eugenol and combinations thereof. According to an embodiment, the primary terpene is selected from the group consisting of thymol, carvacrol, eugenol, nerolidol, linalool, farnesol, citronellol, geraniol, citral and combinations thereof. According to various embodiments said primary terpene comprises pinene, limonene, caryophyllene, caryophyllene oxide, nerolidol, eucalyptol, terpinene, terpineol, myrcene, cycloartenol, citronellol, amyrin, camphene, cymene, Ocimene, humulene, farnesene, guaiol, eudesmol, friedelin, linalool, camphor, menthol, thymol, carvacrol, eugenol, farnesol, citronellol, geraniol, citral and/or ionone.

According to an embodiment said therapeutic effect treats leishmaniasis and said primary terpene is selected from the group consisting of linalool, nerolidol, pinene, caryophyllene and/or eucalyptol.

According to an embodiment said therapeutic effect treats Methycillin-resistant *Staphylococcus aureus* (MRSA) and said administered product comprises at least one of CBD, THC, CBC, CBG, CBN, CBL, THCV and CBDV. According to an embodiment said therapeutic effect treats Methycillin-resistant *Staphylococcus aureus* (MRSA) and said product comprises CBD and optionally THC at CBD to THC weight/weight ratio greater than 1, greater than 2, greater than 3, greater than 4 or greater than 5. According to an embodiment said therapeutic effect treats Methycillin-resistant *Staphylococcus aureus* (MRSA) and said product comprises THC and optionally CBD at THC to CBD weight/weight ratio greater than 0.9, greater than 2, greater than 3, greater than 4 or greater than 5. According to various embodiments, said product comprises CBD, comprises THC, comprises CBC, comprises CBG, comprises CBN, comprises CBL, comprises THCV and/or comprises CBDV. According to an embodiment said therapeutic effect treats Methycillin-resistant *Staphylococcus aureus* (MRSA) and said primary terpene is selected from the group consisting of pinene, caryophyllene, caryophyllene oxide, limonene, nerolidol, cycloartenol, amyrin and combinations thereof. According to an embodiment, the product comprises at least 2 of these terpenes, at least 3, at least 4, or at least 5 of the terpenes. According to an embodiment, the primary terpene is selected from the group consisting of pinene, caryophyllene, limonene, amyrin and combinations thereof. According to various embodiments said primary terpene comprises pinene, caryophyllene, caryophyllene oxide, limonene, nerolidol, cycloartenol and/or amyrin.

According to an embodiment said therapeutic effect treats malaria and said primary terpene is selected from the group consisting of caryophyllene, nerolidol, pinene, eucalyptol, limonene and combinations thereof. According to an embodiment, the product comprises at least 2 of these terpenes, at least 3, at least 4, or at least 5 of the terpenes. According to an embodiment, the primary terpene is selected from the group consisting of caryophyllene, nerolidol, pinene and combinations thereof. According to various embodiments said primary terpene comprises caryophyllene, nerolidol, pinene, eucalyptol and/or limonene.

According to an embodiment said therapeutic effect treats acne and said primary terpene is selected from the group consisting of limonene, linalool, nerolidol, pinene, terpineol and combinations thereof. According to an embodiment, the product comprises at least 2 of these terpenes, at least 3, at least 4, or all 5 of the terpenes. According to an embodiment, the primary terpene is selected from the group consisting of limonene, pinene, terpineol and combinations thereof. According to various embodiments said primary terpene comprises limonene, linalool, nerolidol, pinene and/or terpineol.

According to an embodiment said therapeutic effect treats allergy and said primary terpene is selected from the group consisting of camphene, pinene, borneol, caryophyllene, geraniol and combinations thereof. According to an embodiment, the product comprises at least 2 of these terpenes, at least 3, at least 4, or all 5 of the terpenes. According to an embodiment, the primary terpene is selected from the group consisting of camphene, pinene, caryophyllene and combinations thereof. According to various embodiments said primary terpene comprises camphene, pinene, borneol, caryophyllene and/or geraniol.

According to an embodiment said therapeutic effect treats osteoporosis and said the primary terpene is selected from the group consisting of caryophyllene, caryophyllene oxide, carene, eucalyptol, sabinene, pinene, limonene, borneol, thymol, camphor and combinations thereof. According to an embodiment, the product comprises at least 2 of these terpenes, at least 3, at least 4, or at least 5 of the terpenes. According to an embodiment, the primary terpene is selected from the group consisting of caryophyllene, carene, camphor and combinations thereof. According to an embodiment, the primary terpene is selected from the group consisting of caryophyllene, carene, camphor, pinene, limonene, borneol and combinations thereof. According to various embodiments said primary terpene comprises caryophyllene oxide, eucalyptol, sabinene, pinene, limonene, thymol and/or camphor. According to an embodiment, said therapeutic effect treats osteoporosis said product and comprises a herbal extract selected from the group consisting of extracts of *Angelica sinensis, Cimicifuga (Actaea) racemosa, Dioscorea villosa, Trifolium pratense* and combinations thereof.

According to an embodiment said therapeutic effect treats sleep disorder and/or insomnia and said the primary terpene is selected from the group consisting of linalool, caryophyllene, myrcene, terpineol, terpinene, citronellol, eucalyptol, nerolidol, sabinene, pinene, limonene, borneol, fenchol, bisabolol humulene, phytol, citral and combinations thereof. According to an embodiment, the product comprises at least 2 of these terpenes, at least 3, at least 4, or at least 5 of the terpenes. According to an embodiment, the primary terpene is selected from the group consisting of linalool, terpineol, myrcene and combinations thereof. According to an embodiment, the primary terpene is selected from the group consisting of linalool, terpineol, myrcene, caryophyllene, terpinene, borneol and combinations thereof. According to an embodiment, the primary terpene comprises terpineol, citronellol and/or linalool. According to various embodiments said primary terpene comprises terpineol, terpinene, citronellol, eucalyptol, nerolidol, sabinene, pinene, limonene, borneol, fenchol, bisabolol, phytol and/or humulene. According to an embodiment, said therapeutic effect treats sleep disorder and/or insomnia and the product comprises a compound selected from the group consisting of linalyl acetate and/or chamazulene. According to an embodiment, said therapeutic effect treats sleep disorder and/or insomnia and said product comprises a herbal extract selected from the group consisting of extracts of *Avena sativa, Cimicifuga (actaea) racemosa, Humulus lupulus, Hypericum perforatum, Lavendula officinalis, Melissa officinalis, Passiflora incarnata, Valeriana officinalis* and combinations thereof According to an embodiment, the product includes caryophyllene, and caryophyllene forms less than 5% by weight of the total terpene content.

According to an embodiment said therapeutic effect treats anxiety, irritability, nervousness, restless, stress, depression, general discomfort, mood problems and/or affect disorder and said the primary terpene is selected from the group consisting of limonene, linalool, terpineol, citronellol, eucalyptol, caryophyllene, geraniol, menthol, iso-menthone, germacrene, pinene, citronellol, cardinol, neral, geranial, myrcene, terpinene, menth-2-en-1-ol, humulene, bisabolol, borneol, fenchol, nerolidol, phellandrene and combinations thereof. According to an embodiment, the product comprises at least 2 of these terpenes, at least 3, at least 4, or at least 5 of the terpenes. According to an embodiment, the primary terpene is selected from the group consisting of limonene, linalool, eucalyptol and combinations thereof. According to an embodiment, the primary terpene is selected from the group consisting of limonene, linalool, eucalyptol, terpineol, caryophyllene, pinene, myrcene and combinations thereof. According to an embodiment, the primary terpene is selected from the group consisting of limonene, linalool, caryophyllene, bisabolol and combinations thereof. According to an embodiment, the primary terpene is selected from the group consisting of limonene, linalool, pinene, humulene and combinations thereof. According to various embodiments said primary terpene comprises terpineol, citronellol, caryophyllene, geraniol, menthol, iso-menthone, germacrene, pinene, citronellol, cardinol, neral, geranial, myrcene, terpinene, menth-2-en-1-ol, humulene, bisabolol, borneol, nerolidol phellandrene and/or fenchol. According to an embodiment, said therapeutic effect treats anxiety, irritability, nervousness, restless, stress, depression, general discomfort, mood problems and/or affect disorder and the product comprises a compound selected from the group consisting of linalyl acetate, geranyl acetate, menthol, piperine, eugenol, citronellyl formate, jasmone, benzy acetate, benzyl alcohol and combinations thereof. According to an embodiment, said therapeutic effect treats anxiety, irritability, nervousness, restless, stress, depression, general discomfort, mood problems and/or affect disorder and said product comprises a herbal extract selected from the group consisting of extracts of *Avena sativa, Bacopa monnieri, Centella (Hydrocotyl) asiatica, Humulus lupulus, Hypericum perforatum, Melissa officinalis, Passiflora incarnata, Valeriana officinalis* and combinations thereof. According to an embodiment, the product includes bisabolol, nerolidol, terpinene, myrcene and/or pinene bisabolol, nerolidol, terpinene, myrcene and/or pinene, and bisabolol, nerolidol, terpinene and/or pinene forms less than 5% by weight of the total terpene content.

According to an embodiment said therapeutic effect treats difficulty in concentration, memory loss, and/or dementia and said primary terpene is selected from the group consisting of pinene, pulegone, eucalyptol, terpineol, cymene, ocimene, limonene, linalool, caryophyllene, humulene, carene and combinations thereof. According to an embodiment, the product comprises at least 2 of these terpenes, at least 3, at least 4, or at least 5 of the terpenes. According to an embodiment, the primary terpene is selected from the group consisting of eucalyptol, pinene, limonene and combinations thereof. According to an embodiment, the primary terpene is selected from the group consisting of eucalyptol, pinene, limonene, terpineol, humulene, carene and combinations thereof. According to various embodiments said primary terpene comprises pinene, pulegone, eucalyptol, terpineol, cymene, ocimene, limonene, linalool, caryophyllene, humulene and/or carene. According to an embodiment said therapeutic effect treats difficulty in concentration, memory loss, and/or dementia and said product comprises a herbal extract selected from the group consisting of extracts of *Asphalentum ponjabianum-mumio, Bacopa monnieri, Centella (hydrocotyl) asiatica, Eleutherococcus senticosus, Ginkgo biloba, Lepidium meyenii, Lycium barbarum, Paullinia cupana, Rhodiola rosea* and combinations thereof.

According to an embodiment said therapeutic effect treats muscle pain, myalgia, spasticity, muscle tension, cramps and/or spasms and said primary terpene is selected from the group consisting of myrcene, pinene, nerolidol, linalool, humulene, caryophyllene, limonene, bisabolol, sabinene, citral, eucalyptol, terpineol, geraniol and combinations thereof. According to an embodiment, the product comprises at least 2 of these terpenes, at least 3, at least 4, or at least 5 of the terpenes. According to an embodiment, the primary terpene is selected from the group consisting of myrcene, pinene, limonene and combinations thereof. According to an embodiment, the primary terpene is selected from the group consisting of myrcene, pinene, limonene, nerolidol, linalool, caryophyllene, sabinene and combinations thereof. According to an embodiment, the primary terpene is selected from the group consisting of myrcene, pinene, nerolidol, linalool, humulene and combinations thereof. According to various embodiments said primary terpene comprises myrcene, pinene, nerolidol, linalool, humulene, caryophyllene, limonene, bisabolol, sabinene, citral, eucalyptol, geraniol and/or terpineol According to an embodiment said therapeutic effect treats cramps and/or spasms and said primary terpene is selected from the group consisting of myrcene, pinene, nerolidol, sabinene, eucalyptol and combinations thereof. According to an embodiment said primary terpene is selected from the group consisting of myrcene, linalool, eucalyptol and combinations thereof. According to an embodiment said therapeutic effect treats muscle pain, myalgia, spasticity, muscle tension, cramps and/or spasms and said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis, Chamaemelum, Valeriana edulis* and combinations thereof.

According to an embodiment said therapeutic effect treats fatigue, weakness, decreased mental energy, decreased physical energy, dizziness and/or deficits in balance and said primary terpene is selected from the group consisting of pinene, limonene, terpinene, eucalyptol, myrcene, terpineol, linalool, caryophyllene, borneol and combinations thereof. According to an embodiment, the product comprises at least 2 of these terpenes, at least 3, at least 4, or at least 5 of the terpenes. According to an embodiment, the primary terpene is selected from the group consisting of pinene, terpinene, eucalyptol and combinations thereof. According to an embodiment, the primary terpene is selected from the group consisting of limonene, myrcene, borneol and combinations thereof. According to various embodiments said primary terpene comprises terpinene, myrcene, borneol and/or caryophyllene According to an embodiment said therapeutic effect treats fatigue, weakness, decreased mental energy, decreased physical energy, dizziness and/or deficits in balance and said product comprises a herbal extract selected from the group consisting of extracts of *Eleutherococcus senticosus, Ganoderma lucidum, Grifola frondosa, Lentinula edodes, Lepidium meyenii, Panax ginseng, Rhodiola rosea* and combinations thereof.

According to an embodiment said therapeutic effect treats itchy skin, pruritus and/or chronic pruritus, wrinkles, stretch marks and/or skin burns and said the primary terpene is selected from the group consisting of linalool limonene, nerolidol, pinene terpineol, myrcene, geraniol, nerol, citronellol, farnesol, carotol, sabinene and combinations thereof. According to an embodiment, the product comprises at least 2 of these terpenes, at least 3, at least 4, or at least 5 of the terpenes. According to an embodiment, the primary terpene is selected from the group consisting of linalool, terpineol, geraniol and combinations thereof. According to an embodiment said therapeutic effect treats skin burns and said the primary terpene is linalool and/or sabinene. According to an embodiment said therapeutic effect treats wrinkles, stretch marks and said the primary terpene is selected from the group consisting of geraniol, linalool, citronellol and combinations thereof. According to various embodiments said primary terpene comprises limonene, nerolidol, pinene myrcene, nerol, citronellol, farnesol, linalool, terpineol, geraniol and/or carotol. According to an embodiment, said therapeutic effect treats itchy skin, pruritus and/or chronic pruritus, wrinkles, stretch marks and/or skin burns and the product comprises a compound selected from the group consisting of linalyl acetate, citronellyl formate, eugenol, benzy acetate, benzyl alcohol, and combinations thereof. According to an embodiment said therapeutic effect treats itchy skin, pruritus and/or chronic pruritus, wrinkles, stretch marks and/or skin burns and said product comprises a herbal extract selected from the group consisting of extracts of *Glycyrrhiza glabra, Plantago* spp, *Symphytum officinalis, Trifolium pratense, Trigonella foenum graecum, Ulmus rubra\fulva, Verbascum thapsus* and combinations thereof.

According to an embodiment said therapeutic effect treats headache and/or migraine and said the primary terpene is selected from the group consisting of myrcene, linalool, caryophyllene, eucalyptol, limonene, nerolidol, fenchol, humulene, guaiol, borneol, pinene, bisabolol, terpinene, terpineol and combinations thereof. According to an embodiment, the product comprises at least 2 of these terpenes, at least 3, at least 4, or at least 5 of the terpenes. According to an embodiment, the primary terpene is selected from the group consisting of myrcene, linalool, caryophyllene and combinations thereof. According to an embodiment, the primary terpene is selected from the group consisting of myrcene, linalool, caryophyllene, limonene, nerolidol, fenchol and combinations thereof. According to various embodiments said primary terpene comprises of myrcene, linalool, caryophyllene, eucalyptol, limonene, nerolidol, fenchol, humulene, guaiol, borneol, pinene, terpinene, terpineol and/or bisabolol. According to an embodiment, the product includes linalool, bisabolol and/or humulene wherein linalool, bisabolol and/or humulene forms less than 5% by weight of the total terpene content. According to an embodiment said therapeutic effect treats headache and/or migraine and said product comprises a herbal extract selected from the group consisting of extracts of *Angelica sinensis, Corydalis yanhusuo, Piscidia erythrina, Rosmarinus officinalis, Stachys betonica, Tanacetum parthenium, Verbena officinalis* and combinations thereof.

According to an embodiment said therapeutic effect treats weight gain and/or reduces appetite and said the primary terpene is selected from the group consisting of eucalyptol, caryophyllene, limonene, humulene, phytol and combinations thereof. According to an embodiment, the product comprises at least 2 of these terpenes, at least 3, at least 4, or at least 5 of the terpenes. According to an embodiment, the primary terpene is selected from the group consisting of eucalyptol, limonene, humulene and combinations thereof. According to various embodiments said primary terpene comprises caryophyllene, eucalyptol, limonene, humulene and/or phytol. According to an embodiment said therapeutic effect treats weight gain and/or reduces appetite and said product comprises a herbal extract selected from the group consisting of extracts of *Ephedra sinica, Foeniculum vulgare, Fucus vesiculosus, Garcinia cambogia, Gymnema sylvestre, Laminaria* spp, *Paullinia cupana* and combinations thereof.

According to an embodiment said therapeutic effect treats digestive problem, intestinal disorder, gastrointestinal pain, abdominal pain (colic), pelvic pain, constipation and/or diarrhea and said the primary terpene is selected from the group consisting of limonene, cymene, ocimene, terpinene, caryophyllene, citronellol, sabinene, linalool, pinene, myrcene, germacrene, geraniol, nerolidol, menthol, humulene, fenchol, borneol and combinations thereof. According to an embodiment, the product comprises at least 2 of these terpenes, at least 3, at least 4, or at least 5 of the terpenes. According to an embodiment, the primary terpene is selected from the group consisting of limonene, sabinene, caryophyllene and combinations thereof. According to an embodiment, the primary terpene is selected from the group consisting of limonene, sabinene, caryophyllene, citronellol, linalool, myrcene, nerolidol and combinations thereof According to various embodiments said primary terpene comprises limonene, cymene, ocimene, terpinene, caryophyllene, citronellol, sabinene, linalool, pinene, myrcene, germacrene, geraniol, nerolidol, menthol, humulene, fenchol and/or borneol. According to an embodiment, said therapeutic effect treats digestive problem, intestinal disorder, gastrointestinal pain, abdominal pain (colic), pelvic pain, constipation and/or diarrhea and the product further comprises piperine. According to an embodiment said therapeutic effect treats digestive problems, intestinal disorders, gastrointestinal pain, abdominal pain (colic), pelvic pain, constipation and/or diarrhea and said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis* and combinations thereof. According to an embodiment, the product includes pinene, bisabolol and/or limonene, and pinene, bisabolol and/or limonene forms less than 5% by weight of the total terpene content.

According to an embodiment said therapeutic effect treats lack of appetite, nausea, vomiting and/or anorexia and said the primary terpene is selected from the group consisting of linalool, citronellol, geraniol, menthol, humulene, bisabolol, borneol, fenchol, linalool, limonene, terpineol, pinene, caryophyllene, myrcene, cymene, terpinene and combinations thereof. According to an embodiment, the product comprises at least 2 of these terpenes, at least 3, at least 4, or at least 5 of the terpenes. According to an embodiment, the primary terpene is selected from the group consisting of citronellol, linalool caryophyllene and combinations thereof. According to an embodiment, the primary terpene is selected from the group consisting of citronellol, linalool caryophyllene, limonene, myrcene, nerolidol and combinations thereof According to various embodiments said primary terpene comprises linalool, citronellol, geraniol, menthol, humulene, bisabolol, borneol, fenchol, linalool, limonene, terpineol, pinene, caryophyllene, myrcene, cymene and/or terpinene. According to an embodiment, the product includes pinene. borneol, fenchol, terpinene and/or terpineol, and pinene, bisabolol and/or limonene forms less than 5% by weight of the total terpene content.

According to an embodiment said therapeutic effect treats a joint pain, joint stiffness, arthralgia, arthritis and/or osteoarthritis and said the primary terpene is selected from the group consisting of myrcene, linalool, caryophyllene, eucalyptol, pinene, nerolidol, sabinene, limonene, terpinene, menth-2-en-1-ol, terpineol, geraniol, guaiol, humulene, bisabolol, borneol, fenchol and combinations thereof. According to an embodiment, the product comprises at least 2 of these terpenes, at least 3, at least 4, or at least 5 of the terpenes. According to an embodiment, the primary terpene is selected from the group consisting of myrcene, pinene, sabinene and combinations thereof. According to an embodiment, the primary terpene is selected from the group consisting of myrcene, pinene, sabinene linalool, caryophyllene, limonene and combinations thereof. According to various embodiments said primary terpene comprises myrcene, linalool, caryophyllene, eucalyptol, pinene, nerolidol, sabinene, limonene, terpinene, menth-2-en-1-ol, geraniol, guaiol, humulene, bisabolol, borneol, fenchol 1 and/or terpineol. According to an embodiment, said therapeutic effect treats joint pain, joint stiffness, arthralgia, arthritis and/or osteoarthritis and the product comprises a compound selected from the group consisting of linalyl acetate, geranyl acetate, eugenol, methylis-oeugenol, menthol, eugenyl acetate, piperine and combinations thereof. According to an embodiment said therapeutic effect treats joint pain, joint stiffness, arthralgia, arthritis and/or osteoarthritis and said product comprises a herbal extract selected from the group consisting of extracts of *Boswellia* spp, *Capsicum* spp, *Corydalis yanhusuo*, *Harpagophytum procumbens*, *Piscidia erythrina*, *Salix alba*, *Zingiber officinalis* and combinations thereof. According to an embodiment, the product optionally includes humulene, pinene, bisabolol, borneol, fenchol, guaiol, linalool, ocimene, terpineol, terpinene and/or caryophyllene, and humulene, pinene, bisabolol, borneol, fenchol, guaiol, linalool, ocimene, terpineol, terpinene and/or caryophyllene forms less than 5% by weight of the total terpene content.

According to an embodiment said therapeutic effect treats hot flashes, night sweat, palpitation, irritability and/or restlessness and said the primary terpene is selected from the group consisting of caryophyllene, myrcene, humulene, pinene, linalool, limonene, nerolidol, terpinene, terpineol, geraniol, carene, citronellol, eucalyptol, sabinene, myrtenol, bisabolol, borneol, fenchol and combinations thereof. According to an embodiment, the product comprises at least 2 of these terpenes, at least 3, at least 4, or at least 5 of the terpenes. According to an embodiment, the primary terpene is selected from the group consisting of linalool, limonene, eucalyptol and combinations thereof. According to an embodiment, the primary terpene is selected from the group consisting of linalool, limonene, terpineol, geraniol, citronellol, eucalyptol and combinations thereof. According to various embodiments said primary terpene comprises caryophyllene, myrcene, humulene, pinene, linalool, limonene, nerolidol, terpinene, terpineol, geraniol, carene, citronellol, eucalyptol, sabinene, myrtenol, bisabolol, borneol and/or fenchol. According to an embodiment, said therapeutic effect treats hot flashes, night sweat, palpitation, irritability and/or restlessness and the product further comprises a compound selected from the group consisting of linalyl acetate, geranyl acetate, citronellyl formate and combinations thereof. According to an embodiment said therapeutic effect treats hot flashes, night sweat, palpitation, irritability and/or restlessness and said product comprises a herbal extract selected from the group consisting of extracts of *Angelica sinensis, Anemarrhenae asphodeloides, Cimicifuga (actaea) racemosa, Dioscorea villosa, Salvia officinalis, Salvia officinalis, Rehmania glutinosa preparata* and combinations thereof. According to an embodiment, the product optionally includes pinene, bisabolol and/or terpineol, and pinene, bisabolol and/or terpineol forms less than 5% by weight of the total terpene content.

According to an embodiment said therapeutic effect treats inflammation, oxidative stress and/or paresthesia and said the primary terpene is selected from the group consisting of caryophyllene, pinene, myrcene, limonene, humulene, citronellol, eucalyptol, linalool, beta amyrin, cycloartenol, terpinene, terpineol, geraniol, carvacrol, thymol, cardinol, terpinene, menth-2-en-1-ol, carotol, humulene, nerolidol and combinations thereof. According to an embodiment, the product comprises at least 2 of these terpenes, at least 3, at least 4, or at least 5 of the terpenes. According to an embodiment, the primary terpene is selected from the group consisting of myrcene, limonene, thymol and combinations thereof. According to an embodiment, the primary terpene is selected from the group consisting of caryophyllene, pinene, linalool, humulene, myrcene, limonene, thymol and combinations thereof. According to various embodiments said primary terpene comprises caryophyllene, pinene, myrcene, limonene, humulene, citronellol, eucalyptol, linalool, beta amyrin, cycloartenol, terpinene, terpineol, geraniol, carvacrol, thymol, cardinol, terpinene, menth-2-en-1-ol, carotol, humulene, n and/or nerolidol. According to an embodiment, said therapeutic effect treats inflammation, oxidative stress and/or paresthesia and the product further comprises a compound selected from the group consisting of linalyl acetate, geranyl acetate, eugenol, eugenyl acetate, piperine and combinations thereof. According to an embodiment, the product optionally includes fenchol and/or borneol, and fenchol and/or borneol forms less than 5% by weight of the total terpene content.

According to an embodiment said therapeutic effect treats cardiovascular disease, palpitation and tachycardia and said the primary terpene is selected from the group consisting of linalool, camphene, limonene, pinene, borneol and combinations thereof. According to an embodiment, the product comprises at least 2 of these terpenes, at least 3, at least 4, or all 5 of the terpenes. According to an embodiment, the primary terpene is selected from the group consisting of camphene, limonene, pinene and combinations thereof. According to various embodiments said primary terpene comprises linalool, camphene, limonene, pinene and/or borneol. According to an embodiment said therapeutic effect treats cardiovascular disease, palpitation and tachycardia and said product comprises a herbal extract selected from the group consisting of extracts of *Cimicifuga (actaea) racemosa, Crataegus* spp, *Leonurus* spp, *Passiflora incarnata* and combinations thereof.

According to an embodiment, the enhanced therapeutic effect comprises reducing side effects associated with *cannabis* consumption. According to an embodiment, the primary terpene comprises geraniol, and the side effect comprises hypoglycemia and/or reduction of glucose level. According to an embodiment, the primary terpene is selected from the group consisting of pinene, terpinene, linalool, eucalyptol, myrcene, terpineol, limonene, caryophyllene, borneol and combinations thereof, and the side effect comprises fatigue, weakness, dizziness and/or deficits in balance. According to an embodiment, the primary terpene is selected from the group consisting of camphene, limonene, pinene, borneol and combinations thereof, and the side effect comprises palpitation and/or tachycardia. According to an embodiment, the primary terpene is selected from the group consisting of linalool, citronellol, geraniol, menthol, humulene, bisabolol, borneol, fenchol, linalool, limonene, terpineol, pinene, caryophyllene, myrcene, cymene, terpinene and combinations thereof, and the side effect comprises digestive disorders including vomiting and/or diarrhea. According to an embodiment, the primary terpene is selected from the group consisting myrcene, linalool, caryophyllene, eucalyptol, limonene, nerolidol, fenchol, humulene, guaiol, borneol, bisabolol and combinations thereof, and the side effect comprises headache. According to an embodiment, the primary terpene is selected from the group consisting of pinene, eucalyptol, limonene and combinations thereof, and the side effect comprises coughing. According to an embodiment, the primary terpene is selected from the group consisting of linalool, terpineol, geraniol, thujone, camphor, viridiflorol, borneol, camphene, pinene, eucalyptol, caryophyllene, germacrene, pinene, carene, cirtonellol, nerol, farnesol, limonene, myrcene, terpinene, menth-2-en-1-ol, carotol, sabinene, neral, geranial and combinations thereof, and the side effect comprises impaired fertility. According to an embodiment, the primary terpene is selected from the group consisting of eucalyptol, caryophyllene, limonene, humulene, phytol and combinations thereof, and the side effect comprises increased appetite. According to an embodiment, the primary terpene is selected from the group consisting of pinene, pulegone, eucalyptol, terpineol, cymene, ocimene, limonene, linalool, caryophyllene, humulene, carene and combinations thereof, and the side effect comprises impaired memory, impaired concentration and/or impaired perception. According to an embodiment, the primary terpene is selected from the group consisting of limonene, linalool, caryophyllene, eucalyptol, pinene, myrcene, terpinene, nerolidol, terpineol, geraniol, menthol, citronellol, neral, geraniol, menthol, borneol, phellandrene, bisabolol, fenchol, humulene and combinations thereof, and the side effect comprises anxiety and/or psychotic-like effects.

According to an embodiment, the method for treating a patient comprises administering to said patient a product selected from the group consisting of tablets, gel capsules, medical patches, topicals, creams, varnishes, sublingual oils, sprays, edibles, suppositories including tampons and/or rectal candles, cigarettes, vaporizer liquids, micro and nano-emulsion preparations containing micro and nano-particle, and combinations thereof, containing the administered composition. According to an embodiment, the product comprising tablets containing the composition. According to an embodiment, the product comprising gel capsules containing the composition. According to an embodiment, the product comprising medical patches containing the composition. According to an embodiment, the product comprising topicals containing the composition. According to an embodiment, the product comprising creams containing the composition. According to an embodiment, the product comprising varnishes containing the composition. According to an embodiment, the product comprising sublingual oils containing the composition. According to an embodiment, the product comprising edibles containing the composition. According to an embodiment, the product comprising tampons containing the composition. A According to an embodiment, the product comprising rectal candles containing the composition. According to an embodiment, the product comprising cigarettes containing the composition. According to an embodiment, the product comprising vaporizer liquids containing the composition.

According to an embodiment, provided is a therapeutic product comprising (i) a primary terpene blend in a specific amount, (ii) optionally at least three secondary terpenes, and (iii) optionally at least one cannabinoid; wherein said primary terpene blend comprises five or less terpenes, and wherein each one of those terpenes comprises at least 100% of the total terpene content, forming a therapeutic product with an enhanced therapeutic effect compared with that of a product comprising one half the amount of the primary terpene blend. According to an embodiment said primary terpene blend comprises five or less terpenes, and each one of those comprises at least 10% of the total terpene content, at least 12%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% of the total terpene content. According to an embodiment the primary terpene blend comprises 50% of the total terpene content, 55%, 60%, 65%, 70%, 75%, 80%, 85%, 90%, 95% or 100% of the total terpene content. According to an embodiment the primary terpene blend comprises 50% of the product, 55%, 60%, 65%, 70%, 75%, 80%, 85%, 90%, 95% or 100% of the product. According to an embodiment, the primary terpene blend comprises five or less terpenes, four or less, three or less or two or less terpenes. According to an embodiment, the primary terpene blend comprises one terpene.

According to an embodiment, the product has an enhanced therapeutic effect in treating and/or healing and/or relieving and/or decreasing, preventing and/or reducing the risk associated with, and/or improving the quality of life associated with conditions and/or symptoms associated with at least one of arthritis, osteoarthritis, arthralgia, joint pain, joint stiffness, diabetes, lack of appetite, anorexia, vomiting, nausea, an inflammatory bowel disease including Crohn's disease and ulcerative colitis, dementia, memory loss, osteoporosis, fatigue, weakness, decreased mental energy, decreased physical energy, dizziness, deficits in balance, itchy skin, pruritus and/or chronic pruritus, wrinkles, stretch marks, skin burn, headache, migraine, weight gain, digestive problem, intestinal disorder, gastrointestinal pain, abdominal pain, pelvic pain, constipation, diarrhea, hot flashes, sweating, difficulty in concentration, weakened immune system, cardiovascular disease, palpitation and tachycardia, psoriasis, dermatophytes, *Candida*, leishmaniasis, Methycillin-resistant *Staphylococcus aureus* (MRSA), malaria, allergy, fibromyalgia, nociceptive pain, neuropathic pain, pain, arm or leg pain, acne, insomnia and/or sleep disorders, muscle pain, myalgia, spasticity, muscle tension, cramps, spasms, anxiety, irritability, nervousness, restless, stress, depression, mood problem, affect disorders, anger, autism and/or autism spectrum disorder, neurodegenerative diseases, Alzheimer disease, Parkinson disease, Huntington's disease, Dystonia, Amyotrophic Lateral Sclerosis (ALS), multiple sclerosis, Tourette syndrome, Myasthenia Gravis, epilepsy, cancer, inflammatory airway diseases including asthma and/or chronic obstructive pulmonary disease (COPD), addiction, stroke, traumatic brain injury, motor spasm and/or tic, vocal tic, obsessive compulsive disorder (OCD), attention deficit hyperactivity disorder (ADHD), attention deficit disorder (ADD), cerebral palsy (CP), inflammation, oxidative stress, paresthesia, glaucoma and combinations thereof. According to an embodiment, the conditions and/or symptoms are associated with aging.

According to an embodiment, the product has an enhanced therapeutic effect in treating conditions and/or symptoms associated with aging. According to a related embodiment, the terpenes of said primary terpene blend are selected from the group consisting of caryophyllene, linalool, pinene, eucalyptol, sabinene, terpineol and combinations thereof. According to an embodiment, said primary terpene blend comprises at least 2 of the terpenes, at least 3, at least 4 or at least 5 of the terpenes. According to an embodiment, the terpenes of said primary terpene blend are selected from the group consisting of caryophyllene, linalool, pinene, terpineol and combinations thereof. According to an embodiment, the terpenes of said primary terpene blend are selected from the group consisting of caryophyllene, linalool, sabinene and combinations thereof.

According to an embodiment, the enhanced therapeutic effect applies to a child. As used herein the term "therapeutic effect applies to a child" refers to therapeutic effect observed when the treated patient is a child.

According to an embodiment, the product has an enhanced therapeutic effect in treating a child. According to a related embodiment, the terpenes of said primary terpene blend are selected from the group consisting of caryophyllene, limonene, pinene, terpineol and combinations thereof. According to an embodiment, said primary terpene blend comprises at least 2 of these terpenes, at least 3, or all 4 of the terpenes. According to an embodiment, the terpenes of said primary terpene blend are selected from the group consisting of caryophyllene, limonene and combination thereof.

According to an embodiment, the conditions and/or symptoms are observed in a child.

According to an embodiment, the terpenes of said primary terpene blend are selected from the group consisting of pinene, limonene, linalool, caryophyllene, caryophyllene oxide, myrcene, humulene, borneol, eucalyptol, terpineol, nerolidol, phytol, geraniol, bisabolol, camphene, amyrin, thujone, citronellol, pulegone, cycloartenol, cymene, sabinene, carene, terpinene, fenchol, isopulegol, guaiol, phellandrene, eudesmol, ocimene, cardinol, elemene, friedelin, carvacrol, eugenol, camphor, menthol, iso-menthone, neral, gerial, viridiflorol, germacrene, thymol, Menth-2-en-1-ol, farensol, carotol, myrtenol, isomers thereof and combinations thereof. According to an embodiment, the terpenes of said primary terpene blend are selected from the group consisting of pinene, limonene, linalool, caryophyllene, myrcene, terpineol, eucalyptol, geraniol and combinations thereof. According to an embodiment, the terpenes of said primary terpene blend are selected from the group consisting of pinene, limonene, linalool, caryophyllene, myrcene, terpineol, eucalyptol and combinations thereof. According to an embodiment, the terpenes of said primary terpene blend are selected from the group consisting of pinene, limonene, linalool, caryophyllene, myrcene, terpineol, eucalyptol, geraniol, humulene and combinations thereof. According to an embodiment, at least one of the terpenes is a-cyclic. According to an embodiment, at least one of the terpenes is cyclic. According to an embodiment, at least one of the terpenes is not found in *cannabis* buds or is present there at less than 0.2%, less than 0.1%, less than 0.05% or less than 0.02%. Such terpene is referred to as "non-*cannabis* terpene". According to an embodiment, the therapeutic terpene product comprises the non-*cannabis* terpene at a concentration of at least 0.2%, at least 0.5%, least 0.8%, at least 1%, least 1.5%, at least 2%, at least 3%, least 4%, at least 5%, at least 8% or at least 12%.

According to an embodiment, said primary terpene blend comprises at least one monoterpene selected from the group consisting of limonene, myrcene, pinene, linalool, geraniol, terpinene camphene and isomers thereof. According to an embodiment, said primary terpene blend comprises at least one sesquiterpene selected from the group consisting of nerolidol, caryophyllene, farnesene, Zingiberene, vetivazulene, guaiazulene, longifolene, copaene, patchoulol humulene and isomers thereof. According to an embodiment, said primary terpene blend comprises at least one diterpene selected from the group consisting of phytol, retinal, retinol, phytane, cembrene, sclarene, labdane, abietane, texadiene, stemarene, stemoden and isomers thereof. According to an embodiment, said primary terpene blend comprises at least one hydroxy-terpene selected from the group consisting of nerolidol, geraniol, linalool, phytol and isomers thereof. As used herein "hydroxy-terpene" refers to a terpene carrying a hydroxyl function.

According to an embodiment, at least one of the terpenes is a monoterpene, at least one of the terpenes is a sesquiterpene and the monoterpenes to sesquiterpenes weight/weight ratio (i.e. the weight ratio between the total amount of monoterpenes and the total amount of the sesquiterpenes) is greater than 1.5 greater than 2, greater than 2.5, greater than 3, greater than 3.5, greater than 4, greater than 4.5, greater than 5, greater than 6, greater than 7, greater than 8, greater than 9, greater than 10, greater than 15, or greater than 20.

According to an embodiment, at least one of the terpenes is a monoterpene, at least one of the terpenes is a diterpene and the monoterpenes to diterpenes weight/weight ratio (i.e. the weight ratio between the total amount of monoterpenes and the total amount of the diterpenes) is greater than 5, greater than 6, greater than 7, greater than 8, greater than 9, greater than 10, greater than 12, greater than 14, greater than 16, greater than 18, greater than 20, greater than 25, or greater than 30.

According to an embodiment, at least one of the terpenes carries no hydroxyl group, at least one of the terpenes carries hydroxyl group and the non-hydroxy-terpenes to hydroxyl-terpenes weight/weight ratio (i.e. the weight ratio between the total amount of non-hydroxy-terpenes and the total amount of the hydroxy-terpenes) is greater than 1.5, greater than 2, greater than 2.5, greater than 3, greater than 3.5, greater than 4, greater than 4.5, greater than 5, greater than 6, greater than 7, greater than 8, greater than 9, greater than 10, greater than 15, or greater than 20.

According to an embodiment, the composition comprises less than 1% THC, less than 0.8%, less than 0.6%, less than 0.4%, less than 0.2%, or less than 0.1% THC.

According to an embodiment, the product comprises at least one of bergamottin, apigenin, amentoflavone, quercetin and piperine. According to an embodiment, the product comprises at least two, at least three, or at least four of bergamottin, apigenin, amentoflavone, quercetin and piperine. According to an embodiment, the product comprises bergamottin. According to an embodiment, the product comprises apigenin. According to an embodiment, the product comprises amentoflavone. According to an embodiment, the product comprises quercetin. According to an embodiment, the product comprises piperine.

According to an embodiment, the product results in an increased and/or enhanced therapeutic effect compared with that of a product comprising a smaller amount of said primary terpene blend, e.g. one half of that amount. According to various embodiment, the increased therapeutic effect has various forms, e.g. a shorter onset time, increased magnitude, extended duration, reduced dosages, reduced secondary adverse symptoms, reduced frequency of conditions and/or symptoms, reduced severity of conditions and/or symptoms, reduced consumption of other drugs and combinations thereof. According to an embodiment, the increased therapeutic effect comprises a shorter onset time, or differently put an earlier effect, which is important particularly in cases of sublingual and topical delivery and in cases where a rapid effect is desired, as in treating pain. According to an embodiment, the increased therapeutic effect comprises extended duration of the therapeutic effect, for example an extended time of pain relief. According to an embodiment, the increased therapeutic effect comprises increased magnitude of the therapeutic effect, enabling achieving a desired therapeutic effect on administering smaller doses of cannabinoids, saving thereby on cost. According to an embodiment, the increased therapeutic effect comprises using smaller doses of cannabinoids and still achieving at least the same beneficial result. According to an embodiment, the increased therapeutic effect comprises reduction of secondary adverse symptoms, e.g. adverse symptoms of the main illness, of ones of another illness and/or ones related to administered the product or other drugs. According to an embodiment, the increased therapeutic effect comprises reduced frequency of the conditions and/or symptoms. According to an embodiment, the increased therapeutic effect comprises reduced severity of the conditions and/or symptoms.

According to an embodiment, said enhanced therapeutic effect comprises shorter onset time of the therapeutic effect. According to an embodiment, the primary terpene blend and optionally cannabinoids and secondary terpenes are present in specific amounts, and the onset time of the therapeutic effect, as measured by methods known in the art, is at least 20% shorter than that of a product comprising the same amounts of cannabinoids and secondary terpenes and one half the amount of said primary terpene blend, at least 30%, at least 40%, at least 50%, at least 60%, or at least 70% shorter. Shorter onset time, or differently put an earlier effect, is important particularly in cases of sublingual, edible and topical delivery and in cases where a rapid effect is desired, as in treating pain.

According to an embodiment, said enhanced therapeutic effect comprises longer onset time of the therapeutic effect. According to an embodiment, the primary terpene blend, the optionally cannabinoids and secondary terpenes are present in specific amounts, and the onset time of the therapeutic effect, as measured by methods known in the art, is at least 20% longer than that of a product comprising the same amounts of cannabinoids and secondary terpenes and one half the amount of said primary terpene blend, at least 30%, at least 40%, at least 50%, at least 60%, or at least 70% longer. According to an embodiment, products of delayed onset time are used in combination with shorter onset time to reach a sustained release effect.

According to an embodiment, said enhanced therapeutic effect comprises greater and/or increased magnitude of the therapeutic effect. According to an embodiment, the primary terpene blend, the optionally cannabinoids and secondary terpenes are present in specific amounts, and the magnitude of the therapeutic effect, as measured by methods known in the art, is at least 20% greater compared with that of a product comprising the same amounts of cannabinoids and secondary terpenes and one half the amount of the said primary terpene blend, at least 30%, at least 40%, at least 50%, at least 60%, or at least 70% greater. Without wishing to be limited by any particular theory, such increased magnitude of the therapeutic effect may indicate increased bioavailability. Such increased magnitude enables achieving a desired therapeutic effect on administering smaller doses of cannabinoids, saving thereby on cost.

According to an embodiment, said enhanced therapeutic effect comprises longer and/or extended duration of the therapeutic effect. According to an embodiment, the primary terpene blend, the optionally cannabinoids and secondary terpenes are present in specific amounts, and the duration of the therapeutic effect, as measured by methods known in the art, is at least 20% longer compared with that of a product comprising the same amounts of cannabinoids and secondary terpenes and one half the amount of said primary terpene blend, at least 30%, at least 40%, at least 50%, at least 60%, at least 70%, at least 80%, at least 90% or at least 100% longer.

According to an embodiment, said enhanced therapeutic effect comprises smaller therapeutically effective amount of a product and/or reduced dosages of the product. According to an embodiment, the primary terpene blend, the optionally cannabinoids and secondary terpenes are present in specific amounts, and the therapeutically effective amount of the product, as measured by methods known in the art, is at least 20% smaller compared with that of a product comprising the same amounts of cannabinoids and secondary terpenes and one half the amount of said primary terpene blend, at least 30%, at least 40%, at least 50%, at least 60%, at least 70%, at least 80%, at least 90% or at least 100% smaller.

According to an embodiment, said enhanced therapeutic effect comprises reduced secondary adverse symptoms. According to an embodiment, the primary terpene blend, the optionally cannabinoids and secondary terpenes are present in specific amounts, and the secondary adverse symptoms, as measured by methods known in the art, are reduced by at least 20% compared with that of a product comprising the same amounts of cannabinoids and secondary terpenes and one half the amount of said primary terpene blend, by at least 30%, at least 40%, at least 50%, at least 60%, at least 70%, at least 80%, at least 90% or at least 100%.

According to an embodiment, said enhanced therapeutic effect comprises smaller and/or reduced frequency of conditions and/or symptoms. According to an embodiment, the primary terpene blend, and optionally cannabinoids and secondary terpenes are present in specific amounts, and the frequency of the conditions and/or symptoms, as measured by methods known in the art, is at least 20% smaller compared with that of a product comprising the same amounts of cannabinoids and secondary terpenes and one half the amount of said primary terpene blend, at least 30%, at least 40%, at least 50% at least 60%, at least 70%, at least 80%, or at least 90% smaller.

According to an embodiment, said enhanced therapeutic effect comprises smaller and/or reduced severity of conditions and/or symptoms. According to an embodiment, the primary terpene blend, and optionally cannabinoids and secondary terpenes are present in specific amounts, and the severity of the conditions and/or symptoms, as measured by methods known in the art, is at least 20% smaller compared with that of a product comprising the same amounts of cannabinoids and secondary terpenes and one half the amount of said primary terpene blend, at least 300%, at least 40%, at least 50% at least 60%, at least 70%, at least 80%, or at least 90% smaller.

According to an embodiment, said enhanced therapeutic effect comprises smaller and/or reduced consumption of other drugs. According to an embodiment, the primary terpene blend, and optionally cannabinoids and secondary terpenes are present in specific amounts, and the consumption of other drugs is reduced by at least 20% compared with that of a product comprising the same amounts of cannabinoids and secondary terpenes and one half the amount of said primary terpene blend, reduced by at least 30%, by at least 40%, by at least 50%, by at least 60%, by at least 70%, by at least 80%, or by at least 90%.

According to an embodiment, the product is selected from the group consisting of tablets, gel capsules, medical patches, topicals, creams, varnishes, sublingual oils, sprays, edibles, beverages, suppositories, tampons, rectal candles, cigarettes, vaporizer liquids, nasal preparation, preparations containing micro and/or nano-emulsions, preparations containing micro and/or nano-particles and combinations thereof.

According to an embodiment, the product comprises an additive selected from the group consisting of antioxidants, emulsifiers and texturizers vegetable oils, plant extracts, honey, pharmaceutical excipients, sucrose, glucose and fructose, pharmaceutical excipients and combinations thereof. According to an embodiment, the product comprises a surfactant selected from the group consisting of phospholipids, glycerides, glycolipids and combinations thereof. According to an embodiment, the product further comprises a food-approved texturizer. According to an embodiment, the product further comprises at least 10 ppm ethanol. According to an embodiment, the product further comprises at least one of vitamin C, vitamin E, polyunsaturated fatty acids, beeswax and coconut oil. According to an embodiment, the product further comprises a sweetener. According to an embodiment, the product further comprises omega 3 fatty acid. According to an embodiment, the product further comprises omega 6 fatty acid. According to an embodiment, the product further comprises curcumin.

According to an embodiment, the terpene product of improved therapeutic effect is a human medication. According to an embodiment, the terpene product of improved therapeutic effect is a veterinary medication.

According to an embodiment said therapeutic effect treats diabetes and said primary terpene blend comprises limonene, pinene, linalool, phytol and/or geraniol. According to an embodiment, said primary terpene blend comprises at least 2 of these terpenes, at least 3, at least 4, or all 5 of the terpenes. According to an embodiment said therapeutic effect treats diabetes and terpenes of said primary terpene blend are selected from the group consisting of limonene pinene, linalool, humulene, myrcene, phytol, geraniol, bisabolol, borneol, guaiol, ocimene, fenchol, terpineol, terpinene eucalyptol and combinations thereof. According to an embodiment, said primary terpene blend comprises at least 2 of these terpenes, at least 3, at least 4, or at least 5 of the terpenes. According to an embodiment, said primary terpene blend comprises limonene, linalool and/or geraniol.

According to an embodiment said therapeutic effect treats Crohn's disease and ulcerative colitis and said primary terpene blend comprises limonene, caryophyllene, myrcene, pinene and/or carene. According to an embodiment, said primary terpene blend comprises at least 2 of these terpenes, at least 3, at least 4, or all 5 of the terpenes. According to an embodiment said therapeutic effect treats Crohn's disease and ulcerative colitis and terpenes of said primary terpene blend are selected from the group consisting of limonene, caryophyllene, borneol, myrcene, pinene, terpinene, isopulegol, phellandrene, carene, carvacol, terpineol, humulene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of limonene, caryophyllene, myrcene and combinations thereof. According to an embodiment, said therapeutic effect treats Crohn's disease and ulcerative colitis and the product comprises a compound selected from the group consisting of linalyl acetate, geranyl acetate, eugenol, eugenyl acetate, piperine and combinations thereof. According to an embodiment, the product includes fenchol and fenchol forms less than 5% by weight of the total terpene content.

According to an embodiment said therapeutic effect stimulates the immune system and/or treats weakened immune system and said primary terpene blend comprises linalool, pinene, caryophyllene, amyrin and/or terpinene. According to an embodiment, said primary terpene blend comprises at least 2 of these terpenes, at least 3, at least 4, or all 5 of the terpenes. According to an embodiment said therapeutic effect stimulates the immune system and/or treats weakened immune system and terpenes of said primary terpene blend are selected from the group consisting of linalool, pinene, borneol, caryophyllene, geraniol, amyrin, terpinene, myrcene, eucalyptol, humulene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of linalool, caryophyllene, amyrin, and combinations thereof.

According to an embodiment said therapeutic effect treats Fibromyalgia and said primary terpene blend comprises linalool, caryophyllene, limonene, eucalyptol and/or sabinene. According to an embodiment, said primary terpene blend comprises at least 2 of these terpenes, at least 3, at least 4, or all 5 of the terpenes. According to an embodiment said therapeutic effect treats Fibromyalgia and terpenes of said primary terpene blend are selected from the group consisting of linalool, caryophyllene, limonene, humulene, eucalyptol, amyrin, cycloartenol, pinene, sabinene, myrcene, terpinene, borneol, bisabolol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of linalool, caryophyllene, eucalyptol and combinations thereof. According to an embodiment, the product optionally includes myrcene, humulene, bisabolol, borneol, limonene and/or linalool and myrcene, humulene, bisabolol, borneol, limonene and/or linalool forms less than 5% by weight of the total terpene content.

According to an embodiment said therapeutic effect treats nociceptive pain and said primary terpene blend comprises myrcene, linalool, caryophyllene, terpineol and/or citronellol. According to an embodiment, said primary terpene blend comprises at least 2 of these terpenes, at least 3, at least 4, or all 5 of the terpenes. According to an embodiment said therapeutic effect treats nociceptive pain and terpenes of said primary terpene blend are selected from the group consisting of myrcene, linalool, caryophyllene, eucalyptol, cycloartenol, borneol, sabinene, camphene, terpineol, citronellol, geraniol, humulene, bisabolol, limonene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, linalool, caryophyllene and combinations thereof.

According to an embodiment said therapeutic effect treats neuropathic pain and said primary terpene blend comprises caryophyllene, linalool, eucalyptol, borneol and/or myrcene. According to an embodiment, said primary terpene blend comprises at least 2 of these terpenes, at least 3, at least 4, or all 5 of the terpenes. According to an embodiment said therapeutic effect treats neuropathic pain and terpenes of said primary terpene blend are selected from the group consisting of caryophyllene, linalool, eucalyptol, amyrin, borneol, pinene, terpineol, limonene, nerolidol, geraniol, myrcene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of caryophyllene, linalool, eucalyptol and combinations thereof. According to an embodiment, the product optionally includes humulene, bisabolol, borneol, limonene and/or linalool, and humulene, bisabolol, borneol, limonene and/or linalool forms less than 5% by weight of the total terpene content.

According to an embodiment said therapeutic effect treats pain and terpenes of said primary terpene blend comprises myrcene, linalool, caryophyllene, borneol and/or terpineol. According to an embodiment, said primary terpene blend comprises at least 2 of these terpenes, at least 3, at least 4, or all 5 of the terpenes. According to an embodiment said therapeutic effect treats pain and terpenes of said primary terpene blend are selected from the group consisting of myrcene, linalool, humulene, eucalyptol, caryophyllene, caryophyllene oxide, amyrin, cycloartenol, borneol, sabinene, camphene, nerolidol, terpineol, geraniol, citronellol, camphor, bisabolol, limonene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, linalool, caryophyllene and combinations thereof. According to an embodiment, said therapeutic effect treats pain and the product comprises a compound selected from the group consisting of linalyl acetate, geranyl acetate, eugenol, eugenyl acetate, piperine, methylis-oeugenol, Methyleugenol, menthol and combination thereof. According to an embodiment, the product optionally includes humulene, bisabolol, borneol, limonene and/or linalool, wherein humulene, bisabolol, borneol, limonene and/or linalool forms less than 5% by weight of the total terpene content. According to an embodiment, said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis* and combinations thereof.

According to an embodiment said therapeutic effect treats arm or leg pain and said primary blend comprises linalool, pinene, limonene, terpineol and/or myrcene. According to an embodiment, said primary terpene blend comprises at least 2 of these terpenes, at least 3, at least 4, or all 5 of the terpenes. According to an embodiment said therapeutic effect treats arm or leg pain and terpenes of said primary terpene blend are selected from the group consisting of linalool, terpinene, pinene, limonene, terpineol, myrcene, nerolidol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of linalool, pinene, myrcene and combinations thereof.

According to an embodiment said therapeutic effect treats neurodegenerative diseases including Alzheimer disease, Parkinson disease, Huntington's disease, dystonia and/or Amyotrophic lateral sclerosis (ALS) and said primary terpene blend comprises terpineol, carvophyllene, myrcene, linalool and/or pinene. According to an embodiment, said primary terpene blend comprises at least 2 of these terpenes, at least 3, at least 4, or all 5 of the terpenes. According to an embodiment said therapeutic effect treats neurodegenerative diseases including Alzheimer disease, Parkinson disease, Huntington's disease, dystonia and/or Amyotrophic lateral sclerosis (ALS) and terpenes of said primary terpene blend are selected from the group consisting of terpineol, caryophyllene, myrcene, terpineol, linalool, humulene, eucalyptol, pinene, pulegone, cymene, ocimene, limonene, nerolidol, sabinene, carene, citronellol, geraniol, menthol, borneol, terpinene, bisabolol, fenchol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of carvophyllene, linalool, pinene, terpineol and combinations thereof. According to an embodiment said therapeutic effect treats Alzheimer disease and said primary terpene blend comprises pinene, eucalyptol, linalool, terpineol, myrcene and/or caryophyllene. According to an embodiment said therapeutic effect treats Parkinson disease, Huntington's disease, dystonia and/or Amyotrophic lateral sclerosis (ALS) and said the primary terpene blend comprises caryophyllene, myrcene, linalool, pinene, limonene, nerolidol, sabinene and/or terpineol. According to an embodiment, said therapeutic effect treats neurodegenerative diseases including Alzheimer, Parkinson disease, Huntington's disease, dystonia and/or Amyotrophic lateral sclerosis (ALS) and the product comprises a compound selected from the group consisting of linalyl acetate, geranyl acetate, menthol, piperine, eugenol, citronellyl formate, jasmone, benzy acetate, benzyl alcohol and combination thereof. According to an embodiment, the product includes pinene, myrcene and/or terpineol, and pinene, myrcene and/or terpineol forms less than 5% by weight of the total terpene content.

According to an embodiment said therapeutic effect treats multiple sclerosis and said primary terpene blend comprises caryophyllene, pinene, myrcene, limonene and/or linalool. According to an embodiment, said primary terpene blend comprises at least 2 of these terpenes, at least 3, at least 4, or all 5 of the terpenes. According to an embodiment said therapeutic effect treats multiple sclerosis and terpenes of said primary terpene blend are selected from the group consisting of caryophyllene, pinene, myrcene, limonene, humulene, citronellol, eucalyptol, caryophyllene oxide, linalool, amyrin, cycloartenol, cymene, terpinene, borneol, pulegol, nerolidol, terpineol, sabinene, geraniol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of caryophyllene, myrcene, linalool and combinations thereof.

According to an embodiment said therapeutic effect treats Myasthenia gravis and said primary terpene blend comprises pinene, terpineol, nerolidol, limonene and/or linalool. According to an embodiment, said primary terpene blend comprises at least 2 of these terpenes, at least 3, at least 4, or all 5 of the terpenes. According to an embodiment said therapeutic effect treats Myasthenia gravis and terpenes of said primary terpene blend are selected from the group consisting of pinene, terpineol, eucalyptol, pulegone, cymene, ocimene, nerolidol, limonene, linalool, citronellol, geraniol, menthol, caryophyllene, borneol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of terpineol, eucalyptol, linalool and combinations thereof. According to an embodiment, the product includes myrcene and/or pinene, and myrcene and/or pinene forms less than 5% by weight of the total terpene content.

According to an embodiment said therapeutic effect treats epilepsy and said primary terpene blend comprises linalool, terpineol, ocimene, limonene and/or caryophyllene. According to an embodiment, said primary terpene blend comprises at least 2 of these terpenes, at least 3, at least 4, or all 5 of the terpenes. According to an embodiment said therapeutic effect treats epilepsy and the terpenes of said primary terpene blend are selected from the group consisting of linalool, terpineol, ocimene, myrcene, limonene, caryophyllene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of linalool, terpineol, ocimene and combinations thereof.

According to an embodiment said therapeutic effect treats cancer and/or cancer related symptom and said primary terpene blend comprise limonene, caryophyllene, citronellol, linalool, and/or pinene. According to an embodiment, said primary terpene blend comprises at least 2 of these terpenes, at least 3, at least 4, or all 5 of the terpenes. According to an embodiment said therapeutic effect treats cancer and/or cancer related symptom and the terpenes of said primary terpene blend are selected from the group consisting of myrcene, limonene, caryophyllene, caryophyllene oxide, terpinene, citronellol, linalool, geraniol. Menthol. humulene, amyrin, cycloartenol, pinene, camphene, eucalyptol, terpineol, borneol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of limonene, caryophyllene, linalool and combinations thereof. According to an embodiment, said therapeutic effect treats cancer and/or cancer related symptom and the product comprises a compound selected from the group consisting of linalyl acetate, geranyl acetate, eugenol, eugenyl acetate, piperine, methylis-oeugenol, Methyleugenol, menthol and combination thereof.

According to an embodiment said therapeutic effect treats stroke and/or traumatic brain injury and said primary terpene blend comprises myrcene, caryophyllene, limonene, terpineol and/or eucalyptol. According to an embodiment, said primary terpene blend comprises at least 2 of these terpenes, at least 3, at least 4, or all 5 of the terpenes. According to an embodiment said therapeutic effect treats stroke and/or traumatic brain injury and the terpenes of said primary terpene blend are selected from the group consisting of myrcene, terpinene, caryophyllene, caryophyllene oxide, pinene, limonene, humulene, citronellol, eucalyptol, linalool, amyrin, cycloartenol, terpineol, thymol, eucalyptol, geraniol, carvacrol, thymol, cardinol, menth-2-en-1-ol, carotol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, caryophyllene, limonene and combinations thereof. According to an embodiment, the product includes fenchol and/or borneol, and fenchol and/or borneol forms less than 5% by weight of the total terpene content.

According to an embodiment said therapeutic effect treats addiction, including addiction to drugs, smoking, drinks, food, gambling, sex, and sports and said primary terpene blend comprises caryophyllene, pinene, limonene, linalool and/or terpineol. According to an embodiment, said primary terpene blend comprises at least 2 of these terpenes, at least 3, at least 4, or all 5 of the terpenes. According to an embodiment said therapeutic effect treats addiction, including addiction to drugs, smoking, drinks, food, gambling, sex, and sports and terpenes of said primary terpene blend are selected from the group consisting of caryophyllene, pinene, myrcene, limonene, linalool, terpineol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of caryophyllene, linalool, terpineol and combinations thereof.

According to an embodiment said therapeutic effect treats inflammatory airway diseases including asthma and/or chronic obstructive pulmonary disease (COPD) and said primary terpene blend comprises pinene, eucalyptol, humulene, camphene and/or caryophyllene. According to an embodiment, said primary terpene blend comprises at least 2 of these terpenes, at least 3, at least 4, or all 5 of the terpenes. According to an embodiment said therapeutic effect treats inflammatory airway diseases including asthma and/or chronic obstructive pulmonary disease (COPD) and terpenes of said primary terpene blend are selected from the group consisting of pinene, eucalyptol, limonene, humulene, camphene, caryophyllene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of pinene, eucalyptol, humulene, and combinations thereof.

According to an embodiment said therapeutic effect treats cerebral palsy (CP) and said primary terpene blend comprises myrcene, pinene nerolidol, limonene and/or sabinene. According to an embodiment, said primary terpene blend comprises at least 2 of these terpenes, at least 3, at least 4, or all 5 of the terpenes. According to an embodiment said therapeutic effect treats cerebral palsy (CP) and terpenes of said primary terpene blend are selected from the group consisting of myrcene, pinene, linalool, humulene, nerolidol, limonene, terpineol, sabinene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, pinene, nerolidol and combinations thereof.

According to an embodiment said therapeutic effect treats autism and/or autism spectrum disorder and said primary terpene blend comprises pinene, myrcene, eucalyptol, linalool and/or terpineol. According to an embodiment, said primary terpene blend comprises at least 2 of these terpenes, at least 3, at least 4, or all 5 of the terpenes. According to an embodiment said therapeutic effect treats autism and/or autism spectrum disorder and the terpenes of said primary terpene blend are selected from the group consisting of limonene, caryophyllene, pinene, myrcene, humulene, citronellol, eucalyptol, linalool, terpineol, ocimene, geraniol, menthol, borneol, bisabolol, fenchol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of pinene, eucalyptol, linalool and combinations thereof.

According to an embodiment said therapeutic effect treats attention deficit hyperactivity disorder (ADHD) and/or attention deficit disorder (ADD) and said primary terpene blend comprises linalool, eucalyptol, myrcene, caryophyllene and/or pinene. According to an embodiment, said primary terpene blend comprises at least 2 of these terpenes, at least 3, at least 4, or all 5 of the terpenes. According to an embodiment said therapeutic effect treats obsessive-compulsive disorder (OCD) and said primary terpene blend comprises limonene, eucalyptol, pinene, linalool and/or borneol. According to an embodiment, said primary terpene blend comprises at least 2 of these terpenes, at least 3, at least 4, or all 5 of the terpenes. According to an embodiment said therapeutic effect treats hyperactivity disorder (ADHD), attention deficit disorder (ADD) and/or obsessive-compulsive disorder (OCD) and terpenes of said primary terpene blend are selected from the group consisting of linalool, eucalyptol, terpineol, myrcene, pinene, pulegone, caryophyllene, geraniol, citronellol, menthol, caryophyllene, pinene, borneol, bisabolol, fenchol and combinations thereof. According to an embodiment, said primary terpene blend comprises at least 2 of these terpenes, at least 3, at least 4, or at least 5 of the terpenes. According to an embodiment said therapeutic effect treats hyperactivity disorder (ADHD) and/or attention deficit disorder (ADD) and terpenes of said primary terpene blend are selected from the group consisting of linalool, eucalyptol, myrcene, and combinations thereof. According to an embodiment said therapeutic effect treats obsessive-compulsive disorder (OCD) and terpenes of said primary terpene blend are selected from the group consisting of limonene, eucalyptol, pinene and combination thereof.

According to an embodiment said therapeutic effect treats Tourette syndrome, motor spasms, motor tics and/or vocal tics and said primary terpene blend comprises myrcene, linalool, pinene, nerolidol and/or eucalyptol. According to an embodiment, said primary terpene blend comprises at least 2 of these terpenes, at least 3, at least 4, or all 5 of the terpenes. According to an embodiment said therapeutic effect treats Tourette syndrome, motor spasms, motor tics and/or vocal tics and terpenes of said primary terpene blend are selected from the group consisting of myrcene, linalool, limonene, pinene, nerolidol, caryophyllene, eucalyptol, geraniol, menthol, borneol, bisabolol, fenchol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, limonene, nerolidol and combinations thereof.

According to an embodiment said therapeutic effect treats psoriasis and said primary terpene blend comprises linalool, caryophyllene, limonene, sabinene and/or terpinene. According to an embodiment, said primary terpene blend comprises at least 2 of these terpenes, at least 3, at least 4, or all 5 of the terpenes. According to an embodiment said therapeutic effect treats psoriasis and terpenes of said primary terpene blend are selected from the group consisting of linalool, caryophyllene, limonene and combinations thereof. According to an embodiment, said primary terpene blend comprises at least 2 of these terpenes or all 3 of the terpenes.

According to an embodiment said therapeutic effect treats dermatophytes and said primary terpene blend comprises limonene, caryophyllene, caryophyllene oxide, nerolidol and/or thymol. According to an embodiment, said primary terpene blend comprises at least 2 of these terpenes, at least 3, at least 4, or all 5 of the terpenes. According to an embodiment said therapeutic effect treats dermatophytes and terpenes of said primary terpene blend are selected from the group consisting of limonene, caryophyllene, caryophyllene oxide, nerolidol, eucalyptol, terpinene, cycloartenol, amyrin, campene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of limonene, caryophyllene, caryophyllene oxide and combinations thereof.

According to an embodiment said therapeutic effect treats *candida* infection and said primary terpene blend comprises pinene, limonene, thymol, carvacrol and/or eugenol. According to an embodiment, said primary terpene blend comprises at least 2 of these terpenes, at least 3, at least 4, or all 5 of the terpenes. According to an embodiment said therapeutic effect treats *candida* infection and terpenes of said primary terpene blend are selected from the group consisting of pinene, limonene, caryophyllene, caryophyllene oxide, nerolidol, eucalyptol, terpinene, terpineol, myrcene, cycloartenol, citronellol, amyrin, camphene, cymene, Ocimene, humulene, farnesene, guaiol, eudesmol, friedelin, linalool, camphor, menthol, thymol, carvacrol, eugenol, farnesol, citronellol, geraniol, citral, ionone and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of thymol, carvacrol, eugenol and combinations thereof.

According to an embodiment said therapeutic effect treats leishmaniasis and said primary terpene blend comprises linalool, nerolidol, pinene, caryophyllene and/or eucalyptol. According to an embodiment, said primary terpene blend comprises at least 2 of these terpenes, at least 3, at least 4, or all 5 of the terpenes. According to an embodiment said therapeutic effect treats leishmaniasis and said primary terpene blend comprises linalool and/or nerolidol.

According to an embodiment said therapeutic effect treats Methycillin-resistant *Staphylococcus aureus* (MRSA) and said primary terpene blend comprises pinene, caryophyllene, limonene, eucalyptol and/or amyrin. According to an embodiment, said primary terpene blend comprises at least 2 of these terpenes, at least 3, at least 4, or all 5 of the terpenes. According to an embodiment said therapeutic effect treats Methycillin-resistant *Staphylococcus aureus* (MRSA) and the terpenes of said primary terpene blend are selected from the group consisting of pinene, caryophyllene, caryophyllene oxide, limonene, nerolidol, cycloartenol, amyrin and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of pinene, caryophyllene, limonene, amyrin and combinations thereof.

According to an embodiment said therapeutic effect treats malaria and said primary terpene blend comprises limonene, pinene, linalool, phytol and/or geraniol. According to an embodiment, said primary terpene blend comprises at least 2 of these terpenes, at least 3, at least 4, or all 5 of the terpenes. According to an embodiment said therapeutic effect treats malaria and the terpenes of said primary terpene blend are selected from the group consisting of caryophyllene, nerolidol, pinene, eucalyptol, limonene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of caryophyllene, nerolidol, pinene and combinations thereof.

According to an embodiment said therapeutic effect treats acne and said primary terpene blend comprises limonene, linalool, nerolidol, pinene and/or terpineol. According to an embodiment, said primary terpene blend comprises at least 2 of these terpenes, at least 3, at least 4, or all 5 of the terpenes. According to an embodiment said therapeutic effect treats acne and the terpenes of said primary terpene blend are selected from the group consisting of limonene, linalool, nerolidol, pinene, terpineol and combinations thereof. According to an embodiment, said primary terpene blend comprises at least 2 of these terpenes, at least 3, at least 4, or all 5 of the terpenes. According to an embodiment, the terpenes of said primary terpene blend are selected from the group consisting of limonene, pinene, terpineol and combinations thereof.

According to an embodiment said therapeutic effect treats allergy and said primary terpene blend comprises camphene, pinene, borneol, caryophyllene and/or geraniol. According to an embodiment, said primary terpene blend comprises at least 2 of these terpenes, at least 3, at least 4, or all 5 of the terpenes. According to an embodiment said therapeutic effect treats allergy and terpenes of said primary terpene blend are selected from the group consisting of camphene, pinene, borneol, caryophyllene, geraniol and combinations thereof. According to an embodiment, said primary terpene blend comprises at least 2 of these terpenes, at least 3, at least 4, or all 5 of the terpenes. According to an embodiment, the terpenes of said primary terpene blend are selected from the group consisting of camphene, pinene, caryophyllene and combinations thereof.

According to an embodiment said therapeutic effect treats osteoporosis and said primary terpene blend comprises caryophyllene, carene, borneol, thymol and/or camphor. According to an embodiment, said primary terpene blend comprises at least 2 of these terpenes, at least 3, at least 4, or all 5 of the terpenes. According to an embodiment said therapeutic effect treats osteoporosis and terpenes of said primary terpene blend are selected from the group consisting of caryophyllene, caryophyllene oxide, carene, eucalyptol, sabinene, pinene, limonene, borneol, thymol, camphor and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of caryophyllene, carene, camphor and combinations thereof. According to an embodiment, said therapeutic effect treats osteoporosis said product and comprises a herbal extract selected from the group consisting of extracts of *Angelica sinensis, Cimicifuga (Actaea) racemosa, Dioscorea villosa, Trifolium pratense* and combinations thereof.

According to an embodiment said therapeutic effect treats sleep disorder and/or insomnia and said primary terpene blend comprises linalool, caryophyllene, myrcene, terpineol and/or borneol. According to an embodiment, said primary terpene blend comprises at least 2 of these terpenes, at least 3, at least 4, or all 5 of the terpenes. According to an embodiment said therapeutic effect treats sleep disorder and/or insomnia and terpenes of said primary terpene blend are selected from the group consisting of linalool, caryophyllene, myrcene, terpineol, terpinene, citronellol, eucalyptol, nerolidol, sabinene, pinene, limonene, borneol, fenchol, bisabolol humulene, phytol, citral and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of linalool, terpineol, myrcene and combinations thereof. According to an embodiment, said therapeutic effect treats sleep disorder and/or insomnia and the product comprises a compound selected from the group consisting of linalyl acetate and/or chamazulene. According to an embodiment, said therapeutic effect treats sleep disorder and/or insomnia and said product comprises a herbal extract selected from the group consisting of extracts of *Avena sativa, Cimicifuga (actaea) racemosa, Humulus lupulus, Hypericum perforatum, Lavendula officinalis, Melissa officinalis, Passiflora incarnata, Valeriana officinalis* and combinations thereof According to an embodiment, the product includes caryophyllene, and caryophyllene forms less than 5% by weight of the total terpene content.

According to an embodiment said therapeutic effect treats anxiety, irritability, nervousness, restless, stress, depression, general discomfort, mood problems and said primary terpene blend comprises limonene, linalool, eucalyptol, caryophyllene and/or myrcene. According to an embodiment, said primary terpene blend comprises at least 2 of these terpenes, at least 3, at least 4, or all 5 of the terpenes. According to an embodiment said therapeutic effect treats anxiety, irritability, nervousness, restless, stress, depression, general discomfort, mood problems and/or affect disorder and the terpenes of said primary terpene blend are selected from the group consisting of limonene, linalool, terpineol, citronellol, eucalyptol, caryophyllene, geraniol, menthol, iso-menthone, germacrene, pinene, citronellol, cardinol, neral, geranial, myrcene, terpinene, menth-2-en-1-ol, humulene, bisabolol, borneol, fenchol, nerolidol, phellandrene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of limonene, linalool, eucalyptol and combinations thereof. According to an embodiment, said therapeutic effect treats anxiety, irritability, nervousness, restless, stress, depression, general discomfort, mood problems and/or affect disorder and the product comprises a compound selected from the group consisting of linalyl acetate, geranyl acetate, menthol, piperine, eugenol, citronellyl formate, jasmone, benzy acetate, benzyl alcohol and combinations thereof. According to an embodiment, said therapeutic effect treats anxiety, irritability, nervousness, restless, stress, depression, general discomfort, mood problems and/or affect disorder and product comprises a herbal extract selected from the group consisting of extracts of *Avena sativa, Bacopa monnieri, Centella (Hydrocotyl) asiatica, Humulus lupulus, Hypericum perforatum, Melissa officinalis, Passiflora incarnata, Valeriana officinalis* and combinations thereof. According to an embodiment, the product includes bisabolol, nerolidol, terpinene, myrcene and/or pinene bisabolol, nerolidol, terpinene, myrcene and/or pinene, and bisabolol, nerolidol, terpinene and/or pinene forms less than 5% by weight of the total terpene content.

According to an embodiment said therapeutic effect treats difficulty in concentration, memory loss, and/or dementia and said primary terpene blend comprises eucalyptol, pinene, carene, limonene and/or terpineol. According to an embodiment, said primary terpene blend comprises at least 2 of these terpenes, at least 3, at least 4, or all 5 of the terpenes. According to an embodiment said therapeutic effect treats difficulty in concentration, memory loss, and/or dementia and terpenes of said primary terpene blend are selected from the group consisting of pinene, pulegone, eucalyptol, terpineol, cymene, ocimene, limonene, linalool, caryophyllene, humulene, carene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of eucalyptol, pinene, limonene and combinations thereof. According to an embodiment said therapeutic effect treats difficulty in concentration, memory loss, and/or dementia and said product comprises a herbal extract selected from the group consisting of extracts of *Asphalentum ponjabianum-mumio, Bacopa monnieri, Centella (hydrocotyl) asiatica, Eleutherococcus senticosus, Ginkgo biloba, Lepidium meyenii, Lycium barbarum, Paullinia cupana, Rhodiola rosea* and combinations thereof.

According to an embodiment said therapeutic effect treats muscle pain, myalgia, spasticity, muscle tension, cramps and/or spasms and said primary terpene blend comprises myrcene, pinene, nerolidol, linalool and/or limonene. According to an embodiment, said primary terpene blend comprises at least 2 of these terpenes, at least 3, at least 4, or all 5 of the terpenes. According to an embodiment said therapeutic effect treats muscle pain, myalgia, spasticity, muscle tension, cramps and/or spasms and terpenes of said primary terpene blend are selected from the group consisting of myrcene, pinene, nerolidol, linalool, humulene, caryophyllene, limonene, bisabolol, sabinene, citral, eucalyptol, terpineol, geraniol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, pinene, limonene and combinations thereof. According to an embodiment said therapeutic effect treats cramps and/or spasms and terpenes of said primary terpene blend are selected from the group consisting of myrcene, pinene, nerolidol, sabinene, eucalyptol and combinations thereof. According to an embodiment said primary terpene blend comprises myrcene, linalool, eucalyptol and combinations thereof. According to an embodiment said therapeutic effect treats muscle pain, myalgia, spasticity, muscle tension, cramps and/or spasms and said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis, Chamaemelum, Valeriana edulis* and combinations thereof.

According to an embodiment said therapeutic effect treats fatigue, weakness, decreased mental energy, decreased physical energy, dizziness and/or deficits in balance and said primary terpene blend comprises pinene, terpinene, eucalyptol, myrcene and/or borneol. According to an embodiment, said primary terpene blend comprises at least 2 of these terpenes, at least 3, at least 4, or all 5 of the terpenes. According to an embodiment said therapeutic effect treats fatigue, weakness, decreased mental energy, decreased physical energy, dizziness and/or deficits in balance and terpenes of said primary terpene blend are selected from the group consisting of pinene, limonene, terpinene, eucalyptol, myrcene, terpineol, linalool, caryophyllene, borneol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of pinene, terpinene, eucalyptol and combinations thereof. According to an embodiment said therapeutic effect treats fatigue, weakness, decreased mental energy, decreased physical energy, dizziness and/or deficits in balance and said product comprises a herbal extract selected from the group consisting of extracts of *Eleutherococcus senticosus, Ganoderma lucidum, Grifola frondosa, Lentinula edodes, Lepidium meyenii, Panax ginseng, Rhodiola rosea* and combinations thereof.

According to an embodiment said therapeutic effect treats itchy skin, pruritus and/or chronic pruritus, wrinkles, stretch marks and/or skin burns and said primary terpene blend comprises linalool, terpineol, geraniol, citronellol and/or farnesol. According to an embodiment, said primary terpene blend comprises at least 2 of these terpenes, at least 3, at least 4, or all 5 of the terpenes. According to an embodiment said therapeutic effect treats itchy skin, pruritus and/or chronic pruritus, wrinkles, stretch marks and/or skin burns and the terpenes of said primary terpene blend are selected from the group consisting of linalool limonene, nerolidol, pinene terpineol, myrcene, geraniol, nerol, citronellol, farnesol, carotol, sabinene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of linalool, terpineol, geraniol and combinations thereof. According to an embodiment said therapeutic effect treats skin burns and said primary terpene blend comprises linalool and/or sabinene. According to an embodiment said therapeutic effect treats wrinkles, stretch marks and the terpenes of said primary terpene blend are selected from the group consisting of geraniol, linalool, citronellol and combinations thereof. According to an embodiment, said therapeutic effect treats itchy skin, pruritus and/or chronic pruritus, wrinkles, stretch marks and/or skin burns and the product comprises a compound selected from the group consisting of linalyl acetate, citronellyl formate, eugenol, benzy acetate, benzyl alcohol, and combinations thereof. According to an embodiment said therapeutic effect treats itchy skin, pruritus and/or chronic pruritus, wrinkles, stretch marks and/or skin burns and said product comprises a herbal extract selected from the group consisting of extracts of *Glycyrrhiza glabra, Plantago* spp, *Symphytum officinalis, Trifolium pratense, Trigonella foenum graecum, Ulmus rubra\fulva, Verbascum thapsus* and combinations thereof.

According to an embodiment said therapeutic effect treats headache and/or migraine and said primary terpene blend comprises myrcene, linalool, caryophyllene, limonene and/or nerolidol. According to an embodiment, said primary terpene blend comprises at least 2 of these terpenes, at least 3, at least 4, or all 5 of the terpenes. According to an embodiment said therapeutic effect treats headache and/or migraine and said the terpenes of said primary terpene blend are selected from the group consisting of myrcene, linalool, caryophyllene, eucalyptol, limonene, nerolidol, fenchol, humulene, guaiol, borneol, pinene, bisabolol, terpinene, terpineol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, linalool, caryophyllene and combinations thereof. According to an embodiment, the product includes linalool, bisabolol and/or humulene wherein linalool, bisabolol and/or humulene forms less than 5% by weight of the total terpene content. According to an embodiment said therapeutic effect treats headache and/or migraine and said product comprises a herbal extract selected from the group consisting of extracts of *Angelica sinensis, Corydalis yanhusuo, Piscidia erythrina, Rosmarinus officinalis, Stachys betonica, Tanacetum parthenium, Verbena officinalis* and combinations thereof.

According to an embodiment said therapeutic effect treats weight gain and/or reduces appetite and said primary terpene blend comprises eucalyptol, caryophyllene, limonene, humulene and/or phytol. According to an embodiment, said primary terpene blend comprises at least 2 of these terpenes, at least 3, at least 4, or all 5 of the terpenes. According to an embodiment said therapeutic effect treats weight gain and/or reduces appetite and the terpenes of said primary terpene blend are selected from the group consisting of eucalyptol, caryophyllene, limonene, humulene, phytol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of eucalyptol, limonene, humulene and combinations thereof. According to an embodiment said therapeutic effect treats weight gain and/or reduces appetite and said product comprises a herbal extract selected from the group consisting of extracts of *Ephedra sinica, Foeniculum vulgare, Fucus vesiculosus, Garcinia cambogia, Gymnema sylvestre, Laminaria* spp, *Paullinia cupana* and combinations thereof.

According to an embodiment said therapeutic effect treats digestive problem, intestinal disorder, gastrointestinal pain, abdominal pain (colic), pelvic pain, constipation and/or diarrhea and said primary terpene blend comprises limonene, caryophyllene, sabinene, myrcene and/or linalool. According to an embodiment, said primary terpene blend comprises at least 2 of these terpenes, at least 3, at least 4, or all 5 of the terpenes. According to an embodiment said therapeutic effect treats digestive problem, intestinal disorder, gastrointestinal pain, abdominal pain (colic), pelvic pain, constipation and/or diarrhea and the terpenes of said primary terpene blend are selected from the group consisting of limonene, cymene, ocimene, terpinene, caryophyllene, citronellol, sabinene, linalool, pinene, myrcene, germacrene, geraniol, nerolidol, menthol, humulene, fenchol, borneol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of limonene, sabinene, caryophyllene and combinations thereof. According to an embodiment, said therapeutic effect treats digestive problem, intestinal disorder, gastrointestinal pain, abdominal pain (colic), pelvic pain, constipation and/or diarrhea and the product further comprises piperine. According to an embodiment said therapeutic effect treats digestive problems, intestinal disorders, gastrointestinal pain, abdominal pain (colic), pelvic pain, constipation and/or diarrhea and said product comprises a herbal extract selected from the group consisting of extracts of *Angelica sinensis, Piscidia erythrina, Tanacetum parthenium, Viburnum opulus, Boswellia* spp, *Capsicum* spp, *Corydalis yanhusuo, Harpagophytum procumbens, Rosmarinus officinalis, Salix alba, Zingiber officinalis* and combinations thereof. According to an embodiment, the product includes pinene, bisabolol and/or limonene, and pinene, bisabolol and/or limonene forms less than 5% by weight of the total terpene content.

According to an embodiment said therapeutic effect treats lack of appetite and/or anorexia and said primary terpene blend comprises linalool, citronellol, geraniol, linalool and/or limonene. According to an embodiment, said primary terpene blend comprises at least 2 of these terpenes, at least 3, at least 4, or all 5 of the terpenes. According to an embodiment said therapeutic effect treats nausea and/or vomiting and said primary terpene blend comprises linalool, citronellol, caryophyllene, limonene and/or myrcene. According to an embodiment, said primary terpene blend comprises at least 2 of these terpenes, at least 3, at least 4, or all 5 of the terpenes. According to an embodiment said therapeutic effect treats lack of appetite, nausea, vomiting and/or anorexia and said the terpenes of said primary terpene blend are selected from the group consisting of linalool, citronellol, geraniol, menthol, humulene, bisabolol, borneol, fenchol, linalool, limonene, terpineol, pinene, caryophyllene, myrcene, cymene, terpinene and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of citronellol, linalool caryophyllene and combinations thereof. According to an embodiment, the product includes pinene. borneol, fenchol, terpinene and/or terpineol, and pinene, bisabolol and/or limonene forms less than 5% by weight of the total terpene content.

According to an embodiment said therapeutic effect treats joint pain, joint stiffness, arthralgia, arthritis and/or osteoarthritis and said primary terpene blend comprises myrcene, linalool, pinene, caryophyllene and/or sabinene. According to an embodiment, said primary terpene blend comprises at least 2 of these terpenes, at least 3, at least 4, or all 5 of the terpenes. According to an embodiment said therapeutic effect treats a joint pain, joint stiffness, arthralgia, arthritis and/or osteoarthritis and said the terpenes of said primary terpene blend are selected from the group consisting of myrcene, linalool, caryophyllene, eucalyptol, pinene, nerolidol, sabinene, limonene, terpinene, menth-2-en-1-ol, terpineol, geraniol, guaiol, humulene, bisabolol, borneol, fenchol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, pinene, sabinene and combinations thereof. According to an embodiment, said therapeutic effect treats joint pain, joint stiffness, arthralgia, arthritis and/or osteoarthritis and the product comprises a compound selected from the group consisting of linalyl acetate, geranyl acetate, eugenol, methylis-oeugenol, menthol, eugenyl acetate, piperine and combinations thereof. According to an embodiment said therapeutic effect treats joint pain, joint stiffness, arthralgia, arthritis and/or osteoarthritis and said product comprises a herbal extract selected from the group consisting of extracts of *Boswellia* spp, *Capsicum* spp, *Corydalis yanhusuo, Harpagophytum procumbens, Piscidia erythrina, Salix alba, Zingiber officinalis* and combinations thereof. According to an embodiment, the product optionally includes humulene, pinene, bisabolol, borneol, fenchol, guaiol, linalool, ocimene, terpineol, terpinene and/or caryophyllene, and humulene, pinene, bisabolol, borneol, fenchol, guaiol, linalool, ocimene, terpineol, terpinene and/or caryophyllene forms less than 5% by weight of the total terpene content.

According to an embodiment said therapeutic effect treats hot flashes, night sweat, palpitation, irritability and/or restlessness and said primary terpene blend comprises linalool, terpineol, limonene, citronellol and/or eucalyptol. According to an embodiment, said primary terpene blend comprises at least 2 of these terpenes, at least 3, at least 4, or all 5 of the terpenes. According to an embodiment said therapeutic effect treats hot flashes, night sweat, palpitation, irritability and/or restlessness and the terpenes of said primary terpene blend are selected from the group consisting of caryophyllene, myrcene, humulene, pinene, linalool, limonene, nerolidol, terpinene, terpineol, geraniol, carene, citronellol, eucalyptol, sabinene, myrtenol, bisabolol, borneol, fenchol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of linalool, limonene, eucalyptol and combinations thereof. According to an embodiment, said therapeutic effect treats hot flashes, night sweat, palpitation, irritability and/or restlessness and the product comprises a compound selected from the group consisting of linalyl acetate, geranyl acetate, citronellyl formate and combinations thereof. According to an embodiment said therapeutic effect treats hot flashes, night sweat, palpitation, irritability and/or restlessness and said product comprises a herbal extract selected from the group consisting of extracts of *Angelica sinensis, Anemarrhenae asphodeloides, Cimicifuga (actaea) racemosa, Dioscorea villosa, Salvia officinalis, Salvia officinalis, Rehmania glutinosa preparata* and combinations thereof. According to an embodiment, the product optionally includes pinene, bisabolol and/or terpineol, and pinene, bisabolol and/or terpineol forms less than 5% by weight of the total terpene content.

According to an embodiment said therapeutic effect treats inflammation, oxidative stress and/or paresthesia and said primary terpene blend comprises myrcene, limonene, thymol, caryophyllene and/or linalool. According to an embodiment, said primary terpene blend comprises at least 2 of these terpenes, at least 3, at least 4, or all 5 of the terpenes. According to an embodiment said therapeutic effect treats inflammation, oxidative stress and/or paresthesia and the terpenes of said primary terpene blend are selected from the group consisting of caryophyllene, pinene, myrcene, limonene, humulene, citronellol, eucalyptol, linalool, beta amyrin, cycloartenol, terpinene, terpineol, geraniol, carvacrol, thymol, cardinol, terpinene, menth-2-en-1-ol, carotol, humulene, nerolidol and combinations thereof. According to an embodiment, said primary terpene blend comprises at least 2 of these terpenes, at least 3, at least 4, or at least 5 of the terpenes. According to an embodiment, the terpenes of said primary terpene blend are selected from the group consisting of myrcene, limonene, thymol and combinations thereof. According to an embodiment, said therapeutic effect treats inflammation, oxidative stress and/or paresthesia and the product further comprises a compound selected from the group consisting of linalyl acetate, geranyl acetate, eugenol, eugenyl acetate, piperine and combinations thereof. According to an embodiment, the product optionally includes fenchol and/or borneol, and fenchol and/or borneol forms less than 5% by weight of the total terpene content.

According to an embodiment said therapeutic effect treats inflammation, oxidative stress and/or paresthesia and said primary terpene blend comprises linalool, camphene, limonene, pinene and/or borneol. According to an embodiment, said primary terpene blend comprises at least 2 of these terpenes, at least 3, at least 4, or all 5 of the terpenes. According to an embodiment said therapeutic effect treats cardiovascular disease, palpitation and tachycardia and the terpenes of said primary terpene blend are selected from the group consisting of linalool, camphene, limonene, pinene, borneol and combinations thereof. According to an embodiment, said primary terpene blend comprises at least 2 of these terpenes, at least 3, at least 4, or all 5 of the terpenes. According to an embodiment, the terpenes of said primary terpene blend are selected from the group consisting of camphene, limonene, pinene and combinations thereof. According to an embodiment said therapeutic effect treats cardiovascular disease, palpitation and tachycardia and said product comprises a herbal extract selected from the group consisting of extracts of *Cimicifuga (actaea) racemosa, Crataegus* spp, *Leonurus* spp, *Passiflora incarnata* and combinations thereof.

According to an embodiment, the enhanced therapeutic effect comprises reducing side effects associated with *cannabis* consumption. According to an embodiment the side effect comprises hypoglycemia and/or reduction of glucose level and said primary terpene blend comprises geraniol. According to an embodiment the side effect comprises fatigue, weakness, dizziness and/or deficits in balance and said primary terpene blend comprises pinene, terpinene, eucalyptol, myrcene and/or borneol. According to a related embodiment, said primary terpene blend comprises pinene, terpinene, linalool, eucalyptol, myrcene, terpineol, limonene, caryophyllene and/or borneol. According to an embodiment the side effect comprises palpitation and/or tachycardia and said primary terpene blend comprises linalool, camphene, limonene, pinene and/or borneol. According to an embodiment the side effect comprises palpitation and/or tachycardia and said primary terpene blend comprises linalool, camphene, limonene, pinene and/or borneol. According to an embodiment the side effect comprises digestive disorders including vomiting and/or diarrhea and said primary terpene blend comprises limonene, caryophyllene, sabinene, myrcene and/or linalool. According to a related embodiment, said primary terpene blend comprises linalool, citronellol, geraniol, menthol, humulene, bisabolol, borneol, fenchol, linalool, limonene, terpineol, pinene, caryophyllene, myrcene, cymene and/or terpinene. According to an embodiment the side effect comprises headache and said primary terpene blend comprises myrcene, linalool, caryophyllene, limonene and/or nerolidol. According to a related embodiment, said primary terpene blend comprises myrcene, linalool, caryophyllene, eucalyptol, limonene, nerolidol, fenchol, humulene, guaiol, borneol and/or bisabolol. According to an embodiment the side effect comprises coughing and said primary terpene blend comprises pinene, eucalyptol and/or limonene. According to an embodiment the side effect comprises impaired fertility and said primary terpene blend comprises linalool, geraniol, pinene, eucalyptol and/or limonene. According to a related embodiment, said primary terpene blend comprises linalool, terpineol, geraniol, thujone, camphor, viridiflorol, borneol, champhene, pinene, eucalyptol, caryophyllene, germacrene, pinene, carene, cirtonellol, nerol, farnesol, limonene, myrcene, terpinene, menth-2-en-1-ol, carotol, sabinene, neral and/or geranial. According to an embodiment the side effect comprises increased appetite and said primary terpene blend comprises eucalyptol, caryophyllene, limonene, humulene and/or phytol. According to an embodiment the side effect comprises impaired memory, impaired concentration and/or impaired perception and said primary terpene blend comprises eucalyptol, pinene, carene, limonene and/or terpineol. According to a related embodiment, said primary terpene blend comprises pinene, pulegone, eucalyptol, terpineol, cymene, ocimene, limonene, linalool, caryophyllene, humulene and/or carene. According to an embodiment the side effect comprises anxiety and/or psychotic-like effects and said primary terpene blend comprises limonene, linalool, eucalyptol, caryophyllene and/or myrcene. According to a related embodiment, said primary terpene blend comprises limonene, linalool, caryophyllene, eucalyptol, pinene, myrcene, terpinene, nerolidol, terpineol, geraniol, menthol, citronellol, neral, geraniol, menthol, borneol, phellandrene, bisabolol, fenchol and/or humulene.

According to an embodiment, the method for treating a patient comprises administering to said patient a product selected from the group consisting of tablets, gel capsules, medical patches, topicals, creams, varnishes, sublingual oils, sprays, edibles, beverages, suppositories including tampons and/or rectal candles, liquid nasal preparation, preparations containing micro and nano-emulsions, preparations containing micro and nano-particles, cigarettes, vaporizer liquids and combinations thereof, containing the administered composition. According to an embodiment, the product comprising tablets containing the composition. According to an embodiment, the product comprising gel capsules containing the composition. According to an embodiment, the product comprising medical patches containing the composition. According to an embodiment, the product comprising topicals containing the composition. According to an embodiment, the product comprising creams containing the composition. According to an embodiment, the product comprising varnishes containing the composition. According to an embodiment, the product comprising sublingual oils containing the composition. According to an embodiment, the product comprising edibles containing the composition. According to an embodiment, the product comprising beverages containing the product. According to an embodiment, the product comprising tampons containing the composition. A According to an embodiment, the product comprising rectal candles containing the composition. According to an embodiment, the product comprising cigarettes containing the composition. According to an embodiment, the product comprising vaporizer liquids containing the composition.

Examples 1-100

The Table presents examples of compositions as described herein.

|  | Form | Cannabinoid | Primary terpene | Cannabinoid (% by weight) | Primary terpene (% by weight) | Additive | Therapeutic effect For: |
|---|---|---|---|---|---|---|---|
| 1 | Cigarette | CBD | Caryophyllene | 3 | 1 |  | Osteoporosis |
| 2 | Cigarette | THC | Terpineol | 25 | 10 | Extract of *melissa officinalis* | Sleep disorder |
| 3 | Cigarette | CBD | Linalool | 10 | 2 |  | Anxiety |
| 4 | Cigarette | CBD | Citronellol | 15 | 3 |  | depression |
| 5 | Cigarette | THC and/or CBD | Pinene | 15 | 5 |  | Muscle tension |
| 6 | Cigarette | THC and/or CBD | Myrcene | 25 | 8 | Extract of *salix alba* | Arthritis |
| 7 | Cigarette | THC | Camphene | 20 | 2 |  | Allergy |
| 8 | Cigarette | CBD | Pinene | 15 | 5 |  | Acne |
| 9 | Cigarette | CBD | Limonene | 12 | 5 |  | Candida |
| 10 | Cigarette | THC | Linalool | 20 | 4 | Extract of *melissa officinalis* | Sleep disorder |
| 11 | Cigarette | THC and/or CBD | Nerolidol | 10 | 2 |  | Muscle tension |
| 12 | Cigarette | CBD | Eucalyptol | 12 | 2 | Extract of *bacopa monnieri* | Anxiety |
| 13 | Cigarette | CBD | Pinene | 12 | 4 |  | Fibromyalgia |
| 14 | Cigarette | THC | Eucalyptol | 15 | 3 | Extract of *melissa officinalis* | Sleep disorder |
| 15 | Cigarette | THC and/or CBD | Pinene | 18 | 4 |  | Parkinson disease |
| 16 | Grinded bud | CBD | Caryophyllene | 18 | 2 |  | Nociceptive pain |
| 17 | Oil | CBD | Caryophyllene | 25 | 10 |  | Huntington's disease |
| 18 | Oil | THC and/or CBD | Nerolidol | 20 | 5 |  | Dystonia |
| 19 | Oil | CBD | Terpineol | 18 | 3 |  | Autism |
| 20 | Oil | CBD | Linalool | 20 | 2 |  | Anxiety |
| 21 | Oil | CBD | Terpineol | 30 | 4 |  | Epilepsy |
| 22 | Oil | THC and/or CBD | Nerolidol | 12 | 1 |  | Myasthenia Gravis |
| 23 | Oil | CBD | Terpineol + Citronellol + Linalool | 18 | 2 |  | Depression |

-continued

| | Form | Cannabinoid | Primary terpene | Content (% by weight) Cannabinoid | Primary terpene | Additive | Therapeutic effect For: |
|---|---|---|---|---|---|---|---|
| 24 | Oil | THC | Citronellol | 30 | 4 | Linalyl acetate | Sleep disorder |
| 25 | Oil | THC and/or CBD | Alpha-pinene | 12 | 6 | Extract of boswellia spp | Muscle tension |
| 26 | Oil | CBD | Eucalyptol | 18 | 6 | Extract of bacopa monnieri | Anxiety |
| 27 | Oil | THC | Humulene | 20 | 4 | | ALS |
| 28 | Oil | CBD | Pinene | 15 | 4 | | Tourette syndrome |
| 29 | Oil | THC | Amyrin | 25 | 5 | | Neuropathic pain |
| 30 | Oil | CBD | Pinene | 12 | 6 | | COPD |
| 31 | Oil | CBD | Limonene | 8 | 2 | | Addiction |
| 32 | Oil | THC | Terpineol + Citronellol + Linalool | 25 | 3 | Extract of melissa officinalis | Sleep disorder |
| 33 | Tablets | CBD | Caryophyllene | 5 | 3 | | Addiction |
| 34 | Tablets | CBD | Caryophyllene | 3 | 3 | Extract of angelica sinensis | Osteoporosis |
| 35 | Tablets | CBD | Phellandrene | 5 | 3 | | Ulcerative colitis |
| 36 | Tablets | THC | Citronellol | 5 | 2 | Linalyl acetate | Sleep disorder |
| 37 | Tablets | CBD | Eucalyptol | 5 | 1 | | Anxiety |
| 38 | Tablets | CBD | Sabinene | 10 | 1 | Extract of angelica sinensis | Osteoarthritis |
| 39 | Tablets | THC | Terpineol | 5 | 5 | | Sleep disorder |
| 40 | Tablets | THC and/or CBD | Nerolidol | 10 | 5 | | Leishmaniasis |
| 41 | Tablets | THC and/or CBD | Myrcene | 5 | 3 | | Muscle tension |
| 42 | Tablets | THC | Eucalyptol | 5 | 3 | Extract of melissa officinalis | Sleep disorder |
| 43 | Tablets | CBD | Phytol | 8 | 4 | | Diabetes |
| 44 | Tablets | CBD | Limonene | 10 | 5 | | Anxiety |
| 45 | Tablets | CBD | Eucalyptol | 7 | 7 | | Stroke |
| 46 | Tablets | THC and/or CBD | Pinene | 7 | 3 | Extract of boswellia spp | Muscle tension |
| 47 | Cigarette | CBD | Eucalyptol | 10 | 5 | | Weight gain |
| 48 | Cigarette | THC and/or CBD | Myrcene | 25 | 3 | | Headache |
| 49 | Cigarette | CBD | Alpha-pinene | 12 | 3 | | Fatigue |
| 50 | Cigarette | THC and/or CBD | Nerolidol | 20 | 4 | | Osteoarthritis |
| 51 | Cigarette | THC and/or CBD | Limonene | 22 | 4 | | Digestive problems |
| 52 | Cigarette | CBD | Terpinolene | 8 | 3 | | Fatigue |
| 53 | Cigarette | CBD | Caryophyllene | 15 | 4 | | Crohn's disease |
| 54 | Cigarette | CBD | Terpinene | 18 | 5 | | Ulcerative colitis |
| 55 | Cigarette | CBD | Phytol | 10 | 5 | | Weight gain |
| 56 | Cigarette | CBD | Linalool | 15 | 2 | | Itchy skin |
| 57 | Cigarette | THC and/or CBD | Caryophyllene | 20 | 4 | | Headache |
| 58 | Cigarette | CBD | Limonene | 22 | 1 | | Weight gain |
| 59 | Cigarette | THC and/or CBD | p-Cymene, ocimene | 22 | 5 | Piperine | Digestive problems |
| 60 | Cigarette | THC and/or CBD | Isopulegol | 25 | 6 | | Crohn's disease |
| 61 | Cigarette | THC and/or CBD | Gerniol | 22 | 10 | | Diabetes |
| 62 | Cigarette | CBD | Pinene | 18 | 10 | Extract of ginkgo biloba | Memory loss |
| 63 | Cigarette | CBD | Caryophyllene oxide | 15 | 5 | | MRSA |

-continued

|  | Form | Cannabinoid | Primary terpene | Content (% by weight) Cannabinoid | Primary terpene | Additive | Therapeutic effect For: |
|---|---|---|---|---|---|---|---|
| 64 | Cigarette | THC and/or CBD | Myrcene | 12 | 4 |  | Brain injury |
| 65 | Oil | CBD | Linalool | 30 | 10 |  | Itchy skin |
| 66 | Oil | CBD | Terpinolene | 28 | 6 |  | Fatigue |
| 67 | Oil | THC and/or CBD | Caryophyllene | 15 | 4 |  | Headache |
| 68 | Oil | CBD | Eucalyptol | 30 | 2 |  | Weight gain |
| 69 | Oil | THC and/or CBD | Myrcene | 28 | 3 |  | Nociceptive pain |
| 70 | Oil | CBD | Limonene | 15 | 5 |  | Weight gain |
| 71 | Oil | THC and/or CBD | Eucalyptol | 20 | 8 |  | Dementia |
| 72 | Oil | CBD | Alpha-pinene | 15 | 8 |  | Fatigue |
| 73 | Oil | THC and/or CBD | Linalool | 18 | 1 | Extract of *corydalis yanhusuo* | Migraine |
| 74 | Oil | THC and/or CBD | Borneol | 15 | 2 |  | Neuropathic pain |
| 75 | Oil | THC and/or CBD | Limonene | 8 | 8 |  | Digestive problems |
| 76 | Oil | CBD | Phytol | 12 | 4 |  | Weight gain |
| 77 | Oil | CBD | Terpinene | 15 | 5 |  | Intermittent dizziness |
| 78 | Oil | THC and/or CBD | p-Cymene, ocimene | 8 | 5 | Piperine | Digestive problems |
| 79 | Oil | CBD | Camphene | 12 | 4 |  | Dermatophytes |
| 80 | Oil | THC | Linalool | 12 | 5 |  | Lack of appetite |
| 81 | Oil | THC and/or CBD | γ-Terpinene | 8 | 4 |  | Digestive problems |
| 82 | Oil | THC and/or CBD | Linalool | 18 | 5 |  | Skin burn |
| 83 | Tablets | CBD | Pinene | 10 | 4 |  | Difficulty in concentration |
| 84 | Tablets | THC and/or CBD | γ-Terpinene | 10 | 2 |  | Digestive problems |
| 85 | Tablets | CBD | Alpha-pinene | 5 | 2 |  | Fatigue |
| 86 | Tablets | THC and/or CBD | Limonene | 8 | 5 |  | Tachycardia |
| 87 | Tablets | THC and/or CBD | Nerolidol | 5 | 5 |  | Malaria |
| 88 | Tablets | CBD | Terpinolene | 3 | 1 |  | Fatigue |
| 89 | Tablets | THC and/or CBD | Myrcene | 8 | 3 |  | Hot flashes |
| 90 | Tablets | THC and/or CBD | Humulene | 5 | 1 |  | Diabetes |
| 91 | Tablets | CBD | Linalool | 3 | 1 |  | Itchy skin |
| 92 | Tablets | THC and/or CBD | p-Cymene, ocimene | 5 | 5 |  | Digestive problems |
| 93 | Tablets | CBD | Limonene | 3 | 1 | Extract of *laminaria* spp | Weight gain |
| 94 | Tablets | THC and/or CBD | Myrcene | 8 | 4 |  | Headache |
| 95 | Tablets | THC and/or CBD | Limonene | 5 | 2 |  | Digestive problems |
| 96 | Tablets | CBD | Phytol | 4 | 4 |  | Weight gain |
| 97 | Tablets | THC and/or CBD | Linalool | 8 | 4 | Extract of *corydalis yanhusuo* | Headache |
| 98 | Tablets | THC | Citronellol | 6 | 3 |  | Lack of appetite |
| 99 | Tablets | CBD | Eucalyptol | 6 | 2 |  | Weight gain |
| 100 | Tablets | CBD | Caryophyllene | 5 | 5 |  | Weakened immune System |
| 101 | Oil | THC | Caryophyllene | 8 | 8 |  | Motor tics |
| 102 | Oil | CBD | limonene | 12 | 8 |  | OCD |
| 103 | Tablets | CBD | Linalool | 12 | 4 |  | ADHD |
| 104 | Oil | CBD | Terpineol | 8 | 2 |  | ADD |
| 105 | Oil | THC | Nerolidol | 5 | 2 |  | CP |

[1] Oil herein refers to a composition containing an extract of a cannabis plant material.

Example 106: Treating an Elderly Man with Osteoarthritis

A man at the age of 75 diagnosed with osteoarthritis is treated by administering ground *cannabis* in a vaporizer. The ground *cannabis* contains 12% THC, 0.5% CBD and a primary terpene containing sabinene. Administrating involves 2 puffs per dose, twice a day. Each administered dose contains 15 mg of THC, 0.6 mg of CBD and 6 mg sabinene.

Example 107: Treating an Elderly Man with Alzheimer Disease

A man at the age of 82 diagnosed with Alzheimer disease is treated by administering *cannabis* oil sublingually. The oil contains 4% THC, 12% CBD and a primary terpene containing limonene. Administrating involves 4 droplets per dose, twice per day. Each administered dose contains 6 mg of THC, 19 mg of CBD and 4 mg limonene.

Example 108: Treating a Woman with Multiple Sclerosis

A woman at the age of 25 diagnosed with multiple sclerosis and presenting with symptoms of spasticity is treated by administering ground *cannabis* in a vaporizer. The ground *cannabis* contains 8% THC, 5% CBD and a primary terpene containing caryophyllene. Administrating involves 10 puffs per dose, twice a day. Each administered dose contains 50 mg of THC, 31 mg of CBD and 15 mg caryophyllene.

Example 109: Treating a Child with ADHD

A child at the age of 12 diagnosed with ADHD is treated by administering *cannabis* oil sublingually. The *cannabis* oil contains 0.2% THC, 18% CBD and a primary terpene containing eucalyptol. Administrating involves 1 droplet per dose, twice a day. Each administered dose contains 0.1 mg of THC, 8 mg of CBD and 5 mg eucalyptol.

Example 110: Treating an Elderly Woman with Dementia

A woman at the age of 70 with dementia and memory loss is treated by administering *cannabis* tablets. The tablets contain 2% THC, 6% CBD and a primary terpene containing pinene. Administrating involves 2 tablets per dose, twice a day. Each administered dose contains 3 mg of THC, 9 mg of CBD and 4 mg pinene.

Example 111: Treating a Woman with Myalgia

A woman at the age of 58 with symptoms of myalgia is treated by administering ground *cannabis* in a vaporizer. The ground *cannabis* contains 15% THC, 1% CBD and a primary terpene containing pinene. Administrating involves 3 puffs per dose, 3 times per day. Each administered dose contains 30 mg of THC, 2 mg of CBD and 12 mg pinene.

Example 112: Treating a Woman with Symptoms of Insomnia

A woman at the age of 48 with symptoms of insomnia is treated by administering *cannabis* cigarettes. The cigarette contains 16% THC, 3% CBD and a primary terpene containing terpineol. Administrating involves 5 puffs per dose, 30 minutes before bedtime. Each administered dose contains 50 mg of THC, 9 mg of CBD and 10 mg terpineol.

Example 113: Treating a Woman with Gastrointestinal Pain

A woman at the age of 33 with symptoms of gastrointestinal pain is treated by administering *cannabis* oil sublingually. The *cannabis* oil contains 5% THC, 100% CBD and a primary terpene containing myrcene. Administrating involves 1 droplet per dose, twice a day. Each administered dose contains 2 mg of THC, 4 mg of CBD and 2 mg myrcene.

Example 114: Treating a Child with Tourette Syndrome

A child at the age of 10 diagnosed with Tourette syndrome is treated by administering ground *cannabis* in a vaporizer. The ground *cannabis* contains 9% THC, 6% CBD and a primary terpene containing caryophyllene. Administrating involves 3 puffs per dose, 3 times per day. Each administered dose contains 17 mg of THC, 11 mg of CBD and 3 mg caryophyllene.

Example 115: Treating a Woman with Symptoms of Anxiety and Stress

A woman at the age of 51 with symptoms of anxiety and stress is treated by administering tablets of *cannabis* extract. Each tablet contains 0.5% THC, 16% CBD and a primary terpene containing limonene. Administrating involves 1 tablet per dose, twice a day. Each administered dose contains less than 0.4 mg of THC, 13 mg of CBD and 3 mg eucalyptol.

Example 116: Treating a Child with Epilepsy

A child at the age of 5 diagnosed with severe epilepsy is treated by administering *cannabis* oil sublingually. The *cannabis* oil contains 0.1% THC, 18% CBD and a primary terpene containing linalool. Administrating involves 3 droplets per dose, twice a day. Each administered dose contains 0.1 mg of THC, 21.5 mg of CBD and 8 mg linalool.

Example 117: Treating a Woman with OCD

A woman at the age of 28 diagnosed with OCD is treated by administering *cannabis* oil sublingually. The *cannabis* oil contains 12.5% THC, 12.5% CBD and a primary terpene containing geraniol. Administrating involves 1 droplet per dose, 3 times per day. Each administered dose contains 5 mg of THC, 5 mg of CBD and 3 mg geraniol.

Example 118: Treating a Woman with Neuropathic Pain

A woman at the age of 33 diagnosed with multiple sclerosis and presenting with neuropathic pain is treated by administering *cannabis* oil sublingually. The *cannabis* oil contains 100% THC, 2% CBD and a primary terpene containing nerolidol. Administrating involves 1 droplet per dose, twice a day. Each administered dose contains 4 mg of THC, 0.8 mg of CBD and 2 mg nerolidol.

Example 119: Treating a Woman with Crohn's Disease

A woman at the age of 30 diagnosed with Crohn's disease treated by administering tablets of *cannabis* extract. Each tablet contains 1.3% THC, 31% CBD and a primary terpene containing pinene. Administrating involves 1 tablet per dose, twice a day. Each administered dose contains 0.5 mg of THC, 12.5 mg of CBD and 2.5 mg pinene.

Example 120: Treating a Woman with Symptoms of Depression

A woman at the age of 25 with symptoms of depression is treated by administering *cannabis* cigarettes. The cigarettes contain 0.5% THC, 15% CBD and a primary terpene containing limonene. Administrating involves 5 puffs per dose, 3 times per day. Each administered dose contains 1.5 mg of THC, 45 mg of CBD and 8 mg limonene.

Example 121: Treating an Elderly Man with Parkinson Disease

A man at the age of 68 diagnosed with Parkinson disease presenting with symptoms of severe spasticity is treated by administering ground *cannabis* in a vaporizer. The ground *cannabis* contains 13.5% THC, 0.4% CBD and a primary terpene containing myrcene. Administrating involves 3 puffs per dose, twice a day. Each administered dose contains 25 mg of THC, 0.75 mg of CBD and 8 mg myrcene.

Example 122: Treating an Elderly Woman with Dystonia

A woman at the age of 72 diagnosed with dystonia is treated by administering *cannabis* oil sublingually. The *cannabis* oil contains 5.5% THC, 5.5% CBD and a primary terpene containing pinene. Administrating involves 4 droplet per dose, 3 times per day. Each administered dose contains 9 mg of THC, 9 mg of CBD and 4 mg pinene.

Example 123: Treating a Woman with Symptoms of Nausea and Vomiting

A woman at the age of 25 with symptoms of nausea and vomiting is treated by administering *cannabis* oil sublingually. The *cannabis* oil contains 2% THC, 12% CBD and a primary terpene containing citronellol. Administrating involves 3 droplets per dose, twice a day. Each administered dose contains 2.5 mg of THC, 14.5 mg of CBD and 5 mg citronellol.

Example 124: Treating a Man with Symptoms of Nervousness and Irritability

A man at the age of 49 with symptoms of nervousness and irritability is treated by administering *cannabis* oil sublingually. The oil contains 5.5% THC, 9% CBD and a primary terpene containing linalool. Administrating involves 5 droplets per dose, 3 times per day. Each administered dose contains 11 mg of THC, 18 mg of CBD and 10 mg linalool.

Example 125: Treating an Elderly Man with Diabetes

A man at the age of 71 diagnosed with diabetes is treated by administering *cannabis* oil sublingually. The oil contains 8% THC, 3% CBD and a primary terpene containing pinene. Administrating involves 4 droplets per dose, 3 times per day. Each administered dose contains 13 mg of THC, 5 mg of CBD and 4 mg pinene.

Thus, the scope of the invention shall include all modifications and variations that may fall within the scope of the attached claims. Other embodiments of the invention will be apparent to those skilled in the art from consideration of the specification and practice of the invention disclosed herein. It is intended that the specification and examples be considered as exemplary only, with a true scope and spirit of the invention being indicated by the claimed embodiments.

The invention claimed is:

1. A therapeutic product comprising a monoterpene-enriched extract obtained by extraction with an extractant, said extract comprising:
   (i) at least one cannabinoid, wherein at least 80% of said cannabinoid is in a decarboxylated form produced by heating an acid form of said cannabinoid to a temperature of at least 80° C.;
   (ii) a primary terpene, wherein said primary terpene is at least one monoterpene and forms at least 30% by weight of the total amount of terpenes in the product, and
   (iii) at least 5% by weight of a non-cannabinoid, non-terpene carrier,
      wherein said non-cannabinoid, non-terpene carrier comprises less than 5% by weight cellulose and the total terpenes to total cannabinoids weight/weight ratio in said product is about 0.05 to about 1.0,
   forming a monoterpene-enriched cannabinoid product with an enhanced therapeutic effect compared with that of a product comprising the same amount of said at least one cannabinoid and one half the amount of said at least one monoterpene,
   wherein the therapeutic product is in a form selected from the group consisting of tablets, gel capsules, sublingual oils, edibles, beverages, cigarettes and vaporizer liquids.

2. The therapeutic product of claim 1, wherein said at least one monoterpene comprises a mixture of five or less monoterpenes,
   wherein each one of said five or less monoterpenes independently comprises at least 10% of the total monoterpene content,
   forming a therapeutic product with an enhanced therapeutic effect compared with that of a product comprising one half the amount of the five or less monoterpenes.

* * * * *